US011027052B2

(12) United States Patent
Brewer et al.

(10) Patent No.: US 11,027,052 B2
(45) Date of Patent: Jun. 8, 2021

(54) SYSTEMS AND METHODS FOR PRIMING FLUID CIRCUITS OF A PLASMA PROCESSING SYSTEM

(71) Applicant: HDL Therapeutics, Inc., Vero Beach, FL (US)

(72) Inventors: Hollis Bryan Brewer, Potomac, MD (US); Michael M. Matin, Short Hills, NJ (US); Timothy Jon Perlman, Pleasanton, CA (US)

(73) Assignee: HDL Therapuetics, Inc., Vero Beach, FL (US)

( * ) Notice: Subject to any disclaimer, the term of this patent is extended or adjusted under 35 U.S.C. 154(b) by 196 days.

(21) Appl. No.: 16/198,672

(22) Filed: Nov. 21, 2018

(65) Prior Publication Data

US 2019/0351112 A1    Nov. 21, 2019

Related U.S. Application Data

(60) Provisional application No. 62/589,919, filed on Nov. 22, 2017.

(51) Int. Cl.
*A61M 1/02* (2006.01)
*A61K 31/575* (2006.01)
(Continued)

(52) U.S. Cl.
CPC ......... *A61M 1/0281* (2013.01); *A61K 31/575* (2013.01); *A61K 35/16* (2013.01);
(Continued)

(58) Field of Classification Search
CPC ... A61K 35/16; A61K 31/575; A61M 1/0209; A61M 1/0218; A61M 1/0281;
(Continued)

(56) References Cited

U.S. PATENT DOCUMENTS

| 3,639,725 A | 2/1972 | Maniscalco |
| 3,647,624 A | 3/1972 | Evenson |

(Continued)

FOREIGN PATENT DOCUMENTS

| CA | 1271708 | 7/1990 |
| CH | 617582 | 6/1980 |

(Continued)

OTHER PUBLICATIONS

Frank M. Sacks et al, "Selective delipidation of plasma HDL enhances reverse cholesterol transport in vivo", Journal of Lipid Research vol. 50, 2009, Jan. 14, 2009, 894-907.

(Continued)

*Primary Examiner* — Pranav N Patel
(74) *Attorney, Agent, or Firm* — Novel IP

(57) ABSTRACT

Methods of priming a plasma processing system are disclosed. The plasma processing system has a number of different fluid flow circuits that are defined by sources of fluid, fluid flow paths, waste containers, a mixer, a separator, valves and a pump. A first fluid circuit is flushed, where the first fluid circuit is defined by a source of a first fluid, a first valve positioned between the source of the first fluid and the first fluid flow path, a second valve positioned between the first fluid flow path and the second fluid flow path, a first pump positioned between the second fluid flow path and the third fluid flow path, and a first waste container in fluid communication with the third fluid flow path. A second fluid circuit is then flushed by closing and opening certain valves.

19 Claims, 23 Drawing Sheets

(51) Int. Cl.
  *A61K 35/16* (2015.01)
  *B01D 11/04* (2006.01)
  *B01D 15/10* (2006.01)

(52) U.S. Cl.
  CPC ....... *A61M 1/0209* (2013.01); *B01D 11/0446* (2013.01); *B01D 11/0492* (2013.01); *B01D 15/10* (2013.01)

(58) Field of Classification Search
  CPC .............. A61M 1/3486; A61M 1/3616; A61M 1/3643; A61M 1/38; A61M 2202/0458; A61M 2202/046; A61P 9/10; B01D 11/0446; B01D 11/0492; B01D 15/10
  See application file for complete search history.

(56) References Cited

U.S. PATENT DOCUMENTS

| | | |
|---|---|---|
| 3,744,474 A | 7/1973 | Shaw |
| 3,958,939 A | 5/1976 | Jones |
| 3,983,008 A | 9/1976 | Shinozaki |
| 3,989,466 A | 11/1976 | Pan |
| 4,025,423 A | 5/1977 | Stonner |
| 4,066,011 A | 1/1978 | Ballentine |
| 4,103,685 A | 8/1978 | Lupien |
| 4,124,509 A | 11/1978 | Iijima |
| 4,173,215 A | 11/1979 | Bureau |
| 4,234,317 A | 11/1980 | Lucas |
| 4,235,602 A | 11/1980 | Meyer |
| 4,258,010 A | 3/1981 | Rozsa |
| 4,311,586 A | 1/1982 | Baldwin |
| 4,350,156 A | 9/1982 | Malchesky |
| 4,391,711 A | 7/1983 | Jackson |
| 4,399,217 A | 8/1983 | Holmquist |
| 4,402,940 A | 9/1983 | Nose |
| 4,430,557 A | 2/1984 | Eichelberger |
| 4,435,289 A | 3/1984 | Breslau |
| 4,463,988 A | 8/1984 | Bouck |
| 4,481,189 A | 11/1984 | Prince |
| 4,522,809 A | 6/1985 | Adamowicz |
| 4,540,401 A | 9/1985 | Marten |
| 4,540,573 A | 9/1985 | Neurath |
| 4,591,505 A | 5/1986 | Prince |
| 4,613,501 A | 9/1986 | Horowitz |
| 4,615,886 A | 10/1986 | Purcell |
| 4,643,718 A | 2/1987 | Marten |
| 4,645,512 A | 2/1987 | Johns |
| 4,647,280 A | 3/1987 | Maaskant |
| 4,648,974 A | 3/1987 | Rosskopf |
| 4,668,398 A | 5/1987 | Silvis |
| 4,671,909 A | 6/1987 | Torobin |
| 4,676,905 A | 6/1987 | Nagao |
| 4,677,057 A | 6/1987 | Curtiss |
| 4,680,320 A | 7/1987 | Uku |
| 4,696,670 A | 9/1987 | Ohnishi |
| 4,700,685 A | 10/1987 | Miller |
| 4,701,334 A | 10/1987 | Durth |
| 4,775,483 A | 10/1988 | Mookerjea |
| 4,832,034 A | 5/1989 | Pizziconi |
| 4,835,368 A | 5/1989 | Fortmann |
| 4,836,928 A | 6/1989 | Aoyagi |
| 4,879,037 A | 11/1989 | Utzinger |
| 4,895,558 A | 1/1990 | Cham |
| 4,908,354 A | 3/1990 | Seidel |
| 4,909,940 A | 3/1990 | Horowitz |
| 4,909,942 A | 3/1990 | Sato |
| 4,920,948 A | 5/1990 | Koether |
| 4,923,439 A | 5/1990 | Seidel |
| 4,935,204 A | 6/1990 | Seidel |
| 4,966,709 A | 10/1990 | Nose |
| 4,970,144 A | 11/1990 | Fareed |
| 5,026,479 A | 6/1991 | Bikson |
| 5,055,396 A | 10/1991 | Curtiss |
| 5,080,796 A | 1/1992 | Nose |
| 5,089,602 A | 2/1992 | Isliker |
| 5,112,956 A | 5/1992 | Tang |
| 5,116,307 A | 5/1992 | Collins |
| 5,126,240 A | 6/1992 | Curtiss |
| 5,128,318 A | 7/1992 | Levine |
| 5,152,743 A | 10/1992 | Gorsuch |
| 5,187,010 A | 2/1993 | Parham |
| 5,203,778 A | 4/1993 | Boehringer |
| 5,209,941 A | 5/1993 | Wuest |
| 5,211,850 A | 5/1993 | Shettigar |
| 5,236,644 A | 8/1993 | Parham |
| 5,256,767 A | 10/1993 | Salk |
| 5,258,149 A | 11/1993 | Parham |
| 5,279,540 A | 1/1994 | Davidson |
| 5,301,694 A | 4/1994 | Raymond |
| 5,354,262 A | 10/1994 | Boehringer |
| 5,391,143 A | 2/1995 | Kensey |
| 5,393,429 A | 2/1995 | Nakayama |
| 5,401,415 A | 3/1995 | Rauh |
| 5,401,466 A | 3/1995 | Foltz |
| 5,418,061 A | 5/1995 | Parham |
| 5,419,759 A | 5/1995 | Naficy |
| 5,424,068 A | 6/1995 | Filip |
| 5,476,715 A | 12/1995 | Otto |
| 5,484,239 A | 1/1996 | Chapman |
| 5,484,396 A | 1/1996 | Naficy |
| 5,496,637 A | 3/1996 | Parham |
| 5,523,096 A | 6/1996 | Okarma |
| 5,529,933 A | 6/1996 | Young |
| 5,634,893 A | 6/1997 | Rishton |
| 5,637,224 A | 6/1997 | Sirkar |
| 5,652,339 A | 7/1997 | Lerch |
| 5,679,260 A | 10/1997 | Boos |
| 5,698,432 A | 12/1997 | Oxford |
| 5,707,673 A | 1/1998 | Prevost |
| 5,719,194 A | 2/1998 | Mann |
| 5,744,038 A | 4/1998 | Cham |
| 5,744,039 A | 4/1998 | Itoh |
| 5,753,227 A | 5/1998 | Strahilevitz |
| 5,853,725 A | 12/1998 | Salk |
| 5,855,782 A | 1/1999 | Falkenhagen |
| 5,858,238 A | 1/1999 | McRea |
| 5,877,005 A | 3/1999 | Castor |
| 5,885,578 A | 3/1999 | Salk |
| 5,895,650 A | 4/1999 | Salk |
| 5,911,698 A | 6/1999 | Cham |
| 5,916,806 A | 6/1999 | Salk |
| 5,919,369 A | 7/1999 | Ash |
| 5,928,930 A | 7/1999 | Salk |
| 5,948,441 A | 9/1999 | Lenk |
| 5,951,509 A | 9/1999 | Morris |
| 5,962,322 A | 10/1999 | Kozarsky |
| 5,980,478 A | 11/1999 | Gorsuch |
| 6,004,925 A | 12/1999 | Dasseux |
| 6,017,543 A | 1/2000 | Salk |
| 6,022,333 A | 2/2000 | Kensey |
| 6,037,323 A | 3/2000 | Dasseux |
| 6,037,458 A | 3/2000 | Hirai |
| 6,039,946 A | 3/2000 | Strahilevitz |
| 6,046,166 A | 4/2000 | Dasseux |
| 6,080,778 A | 6/2000 | Yankner |
| 6,127,370 A | 10/2000 | Smith |
| 6,136,321 A | 10/2000 | Barrett |
| 6,139,746 A | 10/2000 | Kopf |
| 6,156,727 A | 12/2000 | Garber |
| 6,171,373 B1 | 1/2001 | Park |
| 6,193,891 B1 | 2/2001 | Kent |
| 6,264,623 B1 | 7/2001 | Strahilevitz |
| 6,309,550 B1 | 10/2001 | Iversen |
| 6,337,368 B1 | 1/2002 | Kobayashi |
| 6,342,262 B1 | 1/2002 | Wuest |
| RE37,584 E | 3/2002 | Cham |
| 6,440,387 B1 | 8/2002 | Yankner |
| 6,472,421 B1 | 10/2002 | Wolozin |
| 6,605,588 B1 | 8/2003 | Lees |
| 6,706,008 B2 | 3/2004 | Vishnoi |
| RE39,498 E | 2/2007 | Cham |
| 7,361,739 B2 | 4/2008 | Bellotti |
| 7,375,191 B2 | 5/2008 | Bellotti |
| 7,393,826 B2 | 7/2008 | Bellotti |

(56) References Cited

U.S. PATENT DOCUMENTS

| | | | |
|---|---|---|---|
| 8,030,281 | B2 | 10/2011 | Bellotti |
| 8,048,015 | B2 | 11/2011 | Bellotti |
| 8,268,787 | B2 | 9/2012 | Bellotti |
| 8,637,460 | B2 | 1/2014 | Bellotti |
| 2001/0028895 | A1 | 10/2001 | Bisgaier |
| 2002/0055529 | A1 | 5/2002 | Bisgaier et al. |
| 2002/0081263 | A1 | 6/2002 | Yankner |
| 2002/0107173 | A1 | 8/2002 | Friedhoff |
| 2002/0128581 | A1 | 9/2002 | Vishnoi |
| 2002/0183379 | A1 | 12/2002 | Yankner |
| 2002/0188012 | A1 | 12/2002 | Bisgaier et al. |
| 2003/0018013 | A1 | 1/2003 | Dasseux et al. |
| 2003/0104350 | A1 | 6/2003 | Bomberger |
| 2003/0127390 | A1 | 7/2003 | Davis |
| 2003/0150809 | A1 | 8/2003 | Bomberger |
| 2004/0106556 | A1 | 6/2004 | Zhu |
| 2004/0170649 | A1 | 9/2004 | Cham |
| 2005/0082271 | A1 | 4/2005 | Kuhne |
| 2005/0158041 | A1 | 7/2005 | Hoehne |
| 2006/0060181 | A1 | 3/2006 | Sasaki |
| 2006/0207440 | A1 | 9/2006 | Matsuo |
| 2007/0272675 | A1 | 11/2007 | Kuhne |
| 2008/0214438 | A1 | 9/2008 | Bellotti |
| 2008/0227726 | A1 | 9/2008 | Bellotti |
| 2008/0230465 | A1 | 9/2008 | Bellotti |
| 2008/0234621 | A1 | 9/2008 | Bellotti |
| 2009/0101576 | A1* | 4/2009 | Rohde ............... A61M 1/3643 210/646 |
| 2011/0318423 | A1 | 12/2011 | Bellotti |
| 2013/0052167 | A1 | 2/2013 | Bellotti |
| 2014/0107029 | A1 | 4/2014 | Bellotti |
| 2016/0324925 | A1 | 11/2016 | Bellotti |
| 2017/0174747 | A1 | 6/2017 | Bellotti |
| 2017/0304513 | A1 | 10/2017 | Min |

FOREIGN PATENT DOCUMENTS

| | | |
|---|---|---|
| CN | 1189378 | 8/1998 |
| DE | 2944138 | 6/1981 |
| DE | 3118072 | 11/1982 |
| DE | 3213390 | 10/1983 |
| DE | 3310263 | 9/1984 |
| DE | 19626955 | 1/1998 |
| DE | 19732240 | 4/1999 |
| EP | 36283 | 9/1981 |
| EP | 267471 | 5/1988 |
| EP | 436703 | 7/1991 |
| EP | 1016832 | 7/2000 |
| EP | 1641421 | 4/2006 |
| EP | 1669676 | 6/2006 |
| EP | 2368565 | 9/2011 |
| FR | 2571971 | 4/1986 |
| JP | 127104 | 10/1980 |
| JP | 277303 | 10/1993 |
| RU | 1116396 | 9/1984 |
| RU | 1204224 | 1/1986 |
| RU | 1752187 | 7/1992 |
| WO | 1988009345 | 12/1988 |
| WO | 1991001674 | 2/1991 |
| WO | 1995003840 | 2/1995 |
| WO | 1998009345 | 3/1998 |
| WO | 1999038498 | 8/1999 |
| WO | 2001045718 | 6/2001 |
| WO | 2001056579 | 8/2001 |
| WO | 2002000266 | 1/2002 |
| WO | 2002010768 | 2/2002 |
| WO | 2002030863 | 4/2002 |
| WO | 2002062824 | 8/2002 |
| WO | 2003000372 | 1/2003 |
| WO | 2003000373 | 1/2003 |
| WO | 2007144572 | 12/2007 |

OTHER PUBLICATIONS

International Search Report for PCT/US18/62339, dated Mar. 5, 2019.
U.S. Appl. No. 12/042,924 , "Final Office Action".
U.S. Appl. No. 13/222,287 , "Notice of Allowance", dated May 16, 2012, 36 pages.
U.S. Appl. No. 13/222,287 , "Office Action", dated Feb. 13, 2012, 7 pages.
U.S. Appl. No. 13/222,287 , Office Action Response, dated Apr. 24, 2012, 6 pages.
U.S. Appl. No. 13/601,131 , "Final Office Action", dated Jun. 5, 2013, 11 pages.
U.S. Appl. No. 13/601,131 , "Non-Final Office Action".
U.S. Appl. No. 13/601,131 , "Notice of Allowance", dated Jul. 3, 2013, 10 pages.
U.S. Appl. No. 13/601,131 , "Notice of Allowance", dated Sep. 16, 2013, 8 pages.
U.S. Appl. No. 14/133,997 , "Non-Final Office Action", dated Jan. 21, 2016, 8 pages.
U.S. Appl. No. 15/214,683 , "Non-Final Office Action", dated Sep. 9, 2016, 8 pages.
Agnese et al., "Evaluation of Four Reagents for Dilipidation of Serum", Clin Biochem, vol. 18, No. 2, 1983, pp. 98-100.
Albouz et al., "Extraction of Plasma Lipids Preserving Antigenic Properties of Proteins and Allowing Quantiation of Gangliosides by Neuraminic Acid Determination", Annales de Biologie Clinique, vol. 37(5), 1979, pp. 287-290.
Andre et al., "Characterization of Low- and Very-Low-Density Hepatitis C Virus RNA-Containing Particles", Journal of Virology, vol. 76, No. 14, Jul. 2002, pp. 6919-6928.
Asztalos et al., "Distribution of Apo A-I-Containing HDL Subpopulations in Patients with Coronary Heart Disease", Arteriosclerosis, Thrombosis, and Vascular Biology, vol. 20, Dec. 2000, pp. 2670-2676.
Asztalos et al., "Presence and Formation of Free Apolipoprotein A-I-Like Particles in Human Plasma", Arteriosclerosis, Thrombosis, and Vascular Biology, vol. 15, Sep. 1995, pp. 1419-1423.
Asztalos et al., "Role of Free Apolipoprotein A-I in Cholesterol Efflux", Arteriosclerosis, Thrombosis, and Vascular Biology, vol. 17, Sep. 1997, pp. 1630-1636.
Badimon et al., "High Density Lipoprotein Plasma Fractions Inhibit Aortic Fatty Streaks in Cholesterol-Fed Rabbits", Laboratory Investigation, 1989, 60, 455-461.
Badimon et al., "Regression of Atherosclerotic Lesions by High Density Lipoprotein Plasma Fraction in the Cholesterol-Fed Rabbit", J. Clinical Investigation, 1990, 85, 1234-1241.
Barrans et al., "Hepatic Lipase Induces the formation of pre-beta 1 high densitiy lipoprotein (HDL) from tricylglycerol-righ HDL2. A Study comparing liver perfusion to in vitro Incubation with lipases", Journal of Biological Chemistry, vol. 269, No. 15, Apr. 15, 1994, pp. 11572-11577.
Barrans et al., "Pre-Beta HDL: Structure and Metabolism", Biochimica et Biophysica Acta, vol. 1300, No. 2, Apr. 19, 1996, pp. 73-85.
Barrans et al., "Hepatic Lipase Induces the Formation of Pre-beta 1 High Density Lipoprotein (HDL) from Triacylglycerol Arich HDL2, A study comparing liver perfusion to in vitro incubation with lipases", Journal of Biological Chemistry, vol. 269, No. 15, Apr. 15, 1994, pp. 11578-11583.
Barres et al., "Cholesterol—Making or Breaking the Synapse", Science, vol. 294, No. 5545, Nov. 9, 2001, pp. 1296-1297.
Blanche et al., "Characterization of Complexes of Egg Yolk Phosphatidylcholine and Apolipoprotein A-II Prepared in Absence and Presence of Sodium Cholate", Biochimica et Biophysica Acta, 1988, v. 958, pp. 143-152.
Bloom et al., "Quantitation of Lipid Profiles from Isolated Serum Lipoproteins using Small Volumes of Human Serum", Clin. Biochem, vol. 14 (Abstract only), Jun. 1981, pp. 119-125.
Burns et al., "Use of In Vivo Models to Study the Role of Cholesterol in the Etiology of Alzheimer's Disease", Neurochem Res. Jul. 2003;28(7):979-86., Jul. 2003, 979-86.
Calero et al., "Functional and Structural properties of lipid-associated apolipoprotein J (clusterin)", Biochemical Journal, vol. 344, Issue 2, Dec. 1, 1999, pp. 375-383.

(56) References Cited

OTHER PUBLICATIONS

Cham et al., "Changes in Electrophoretic Mobilities of alpha- and beta-Lipoproteins as a Result of Plasma Delipidation", Clinical Chemistry, 1976, v. 22, 305-309.
Cham et al., "Heterogeneity of Lipoprotein Beta", Biochemical and Biophysical Research Communications, 1981, v. 103, 196-206.
Cham et al., "Importance of Apolipoproteins in Lipid Metabolism", Chem. Biol. Interactions, vol. 20, 1978, pp. 263-277.
Cham et al., "In Vitro Partial Relipidation of Apolipoproteins in Plasma", J. Biol. Chem, 1976, v. 251, 6367-6371 (Abstract only).
Cham et al., "Lipid Apheresis in an Animal Model Causes Acute Reduction in Plasma Lipid Concentrations and Mobilisation of Lipid from Liver and Aorta", Pharmacol (Life Sci. Adv.), 1994, v. 13, 25-32.
Cham et al., "Lipid Apheresis in an Animal Model Causes In Vivo Changes in Lipoprotein Electrophoretic Patterns", J. Clin. Apheresis, 1996, v. 11, 61-70.
Cham, "Nature of the Interaction Between Low-Density Lipoproteins and Polyanions and Metal Ions, as Exemplified by Heparin and Ca2", Clinical Chemistry, 1976, v. 22, pp. 1812-1816.
Cham et al., "Phospholipids in EDTA—Treated Plasma and Serum", Clinical Chemistry, 1993, 39, 2347-2348.
Cham et al., "Rapid Regression of Atherosclerosis by Cholesterol Alpheresis—A Newly Developed Technique", 59th Congress European Atherosclerosis Society, Nice, France, May 1992, 17-21 (Abstract only).
Cham et al., "Rapid, Sensitive Method for the Separation of Free Cholesterol from Ester Cholesterol", Clinica Chimica Acta, 1973, v. 49, 109-113.
Cham et al., "A solvent system for delipidation of plasma or serum without protein precipitation", Journal of Lipid Research, 1976, vol. 17, pp. 176-181.
Cham et al., "Lipid Apheresis: An In Vivo Application of Plasma Delipidation with Organic Solvents Resulting in Acute Transient Reduction of Circulating Plasma Lipids in Animals", Journal of Clinical Apheresis, 1995, pp. 61-69.
Clay et al., "Formation of Apolipoprotein-Specific High-density Lipoprotein particles from Lipid-Free Apolipoproteins A-1 and A-11", Biochem. J., Feb. 1, 1999, 337, 445-451.
Collet et al., "Differential Effects of Lecithin and Cholesterol on the Immunoreactivity and Confirmation of Apolipoprotein A-I in High Density Lipoproteins", Journal of Biological Chemistry, May 15, 1991, v. 266(14), 9145-9152.
Cooper, "Dietary Lipids in the Aetiology of Alzheimer's Disease: Implications for Therapy", Drugs Aging, 2003, v. 20(6), 399-418 (Abstract only).
Cruzado et al., "Characterization and Quantitation of the Apoproteins of High-Density Lipoprotein by Capillary Electrophoresis", Analytical Biochemistry, vol. 243(1), Dec. 1996, pp. 100-109.
Dass et al., "Apolipoprotein A-1, Phospholipid Vesicles, and Cyclodextrins as Potential Anti-Atherosclerotic Drugs: Delivery, Pharmacokinetics, and Efficacy", Drug Delivery, vol. 7, 2000, pp. 161-182.
Deva et al., "Establishment of an in-use testing method for evaluating disinfection of surgical instruments using the duck hepatitis B model", J. Hosp. Infect. vol. 22, No. 2, 1996, 119-30.
Durbin et al., "The Effect of Apolipoprotein A-II on the Structure and Function of Apolipoprotein A-I in a Homogeneous Reconstituted High Density Lipoprotein Particle", The Journal of Biological Chemistry v. 272(50), pp. 31333-31339.
Durbin et al., "Lipid-free Apolipoproteins A-I and A-II promote remodeling of reconstituted high density lipoproteins and alter their reactivity with lecithin: cholesterol acyltransferase", Journal of Lipid Research, vol. 40, No. 12, 1999, pp. 2293-2302.
Dwivedy, "Increase of Reverse Cholesterol Transport by Cholesterol Apheresis Regression of Atherosclerosis", 18th Australian Atherosclerosis Society Conference, Surfers Paradise, 1992, p. 21.
Eisenhauer et al., "Selective Removal of Low Density Lipoproteins (LDL) by Precipitation at Low pH: First Clinical Application of the HELP System", Klin Wochenschr (KWH), 1987, 65, 161-168.

European Application No. 04718501.2, "Office Action", dated Feb. 5, 2014, 7 pages.
European Application No. 04718501.2, "Response to Office Action in Related European Application No. 04 718 501.2", dated May 28, 2014, 8 pages.
European Application No. 10185381.0, "Extended European Search Report", dated Aug. 12, 2011, 8 pages.
European Application No. 10 185 381.0, "Response to Office Action", dated Aug. 7, 2013, 7 pages.
European Application No. 10185381.0, "Office Action", dated Sep 10, 2014, 3 pages.
European Application No. 10185381.0, "Office Action", dated Feb. 7, 2014, 5 pages.
European Application No. 10185381.0, "Response to Office Action in Related European Application No. 10 185 381.0", dated May 28, 2014, 6 pages.
Fang et al., "In Vivo Rapid Mobilization of Adipose Tissue by Lipid Apheresis—A Newly Developed Technique", 18th Australian Atherosclerosis Society Conference, Gold Coast, Australia, 1992.
Feinstone et al., "Inactivation of Hepatitis B Virus and Non-A, Non-B Hepatitis by Chloroform", Infection and Immunity, vol. 41, No. 2, Aug. 1983, 816-21.
Gasparini et al., "Peripheral Markers in testing pathophysiological hypotheses and diagnosing Alzheimer's disease", Faseb. J., 1998, 12, 17-34.
Gauthier et al., "Alzheimer's Disease: Current Knowledge, Management and Research", Canadian Medical Association Journal, vol. 157(8), Oct. 1997, pp. 1047-1052.
Golde et al., "Cholesterol Modulation as an Emerging Strategy for the Treatment of Alzheimer's Disease", Drug Discovery Today, Oct. 15, 2001, 6(20), 1049-1055 (Abstract only).
Greicius et al., "Presenile Dementia Syndromes: An update on Taxonomy and diagnosis", J. Neurol. Neurosurg. Psychiatry, 2002, 72, 691-700.
Haas et al., "Apoliprolein E forms stable complexes with recombinant Aizheimer's disease B-amyloid precursor protein", Biochemical Journal, Jan. 1, 1997, vol. 325, 169-175.
Hatch et al., "Practical Methods for Plasma Lipoprotein Analysis", Advances in Lipid Research, vol. 6, 1968, pp. 61-68.
Horowitz et al., "Viral Safety of Solvent/detergent-treated Blood Products", Blood Coagulation and Fibrinolysis, vol. 5, Suppl. 3, Dec. 1994, pp. S21-S28.
Innerarity et al., "Enhanced Binding by Cultured Human Fibroblasts of Apo-E Containing Lipoproteins as Compared with Low Density Lipoproteins", Biochemistry, vol. 17(8), Apr. 1978, pp. 1449-1447.
Ito et al., "Cholesterol-Sphingomyelin Interaction in Membrane and Apolipoprotein-mediated Cellular Cholesterol Efflux", J. of Lipid Research, Jun. 2000, vol. 41, pp. 894-904.
Jackson et al., "Isolation and Characterization of the Major Apolipoprotein from Chicken High Density Lipoproteins", Biochimica et Biophysica Acta, 1976, v. 420, 342-349.
Klimov et al., "Extraction of Lipids from Blood Plasma and Subsequent Introduction of Autologous Delipidized Plasma into the Body as a Possible Means to Treat Atherosclerosis", Russian Journal Kardiologia vol. 18, No. 6, 1978, 23-9.
Koizumi et al., "Behaviour of Human Apolipoprotein A-1: Phospho-Lipid and apoHDL: Phospholipid Complexes in Vitro and After Injection Into Rabbits", Journal of Lipid Research, vol. 29, 1988, pp. 1405-1415.
Kostner et al., "Beyond LDL-Cholesterol: New Treatments Raising HDL-Cholesterol or Enhancing Reverse Cholesterol Transport", Journal fur Kariologie, vol. 7-8, Sep. 2002, pp. 328-331.
Kostner et al., "Increase of APO Al Concentration in Hypercholesteraemic Chickens after Treatment with a Newly Developed Extracorpreal Lipid Elimination", 11th International Symposium on Drugs Affecting Lipid Metabolism, May 1992.
Kostner et al., "Lecithin-cholesterol acyltransferase activity in Normocholesterolaemic and Hypercholesterolaemic Roosters: Modulation by Lipid Apheresis", European Journal of Clinical Investigation, vol. 27(3), May 1997, pp. 212-218.
Koudinov et al., "Alzheimer's amyloid beta interaction with normal human plasma high density lipoprotein: association with apolipoprotein and lipids", Clin Chim Acta. 270(2), Feb. 23, 1998, 75-84.

(56) References Cited

OTHER PUBLICATIONS

Koudinov et al., "Alzheimer's soluble amyloid beta protein is secreted by HepG2 cells as an apolipoprotein", Cell Biol Int. May 1997; 21(5), May 1997, 265-71.
Koudinov et al., "Biochemical characterization of Alzheimer's soluble amyloid beta protein in human cerebrospinal fluid: association with high density lipoproteins", Biochem Biophys Res Commun. 223(3), Jun. 25, 1996, 592-7.
Koudinov et al., "Cholesterol's Role in Synapse Formation", Science. Mar. 22, 2002;295(5563), Mar. 22, 2002, 2213.
Koudinova et al., "Amyloid Beta, Neural Lipids, Cholesterol and Alzheimer's Disease", Neurobiology of Lipids, vol. 1, 2002, 27.
Kunitake et al., "Interconversion between Apolipoprotein A-I-containing Lipoproteins of Pre-beta and Alpha Electrophoretic Mobilities", J. Lipid Res., Dec. 1992, vol. 33(12), 1807-1816.
Ladu et al., "Association of Human, Rat, and Rabbit Apolipoprotein E with B-amyloid", Journal of Neuroscience Research, 1997, v. 49 (1),9-18.
Lipid Sciences, "Lipid Technology", http:llwww.lipidsciences.com/technology.html, Aug. 25, 2001, 1-4.
Lupien et al., "A New Approach to the Management of Familial Hypercholesterolaemia: Removal of Plasma-Cholesterol Based on the Principle of Affinity Chromatography", Lancet, vol. 1(7972), Jun. 1976, pp. 1261-1265.
Matz et al., "Reaction of Human Lecithin Cholesterol Acyltransferase with Synthetic Micellar Complexes of Apolipoprotein A-1, Phosphatidylcholine, and Cholesterol", The Journal of Biological Chemistry, vol. 257, Apr. 1982, pp. 4541-4546.
Mauch et al., "CNS Synaptogenesis Promoted by Glia-Derived Cholesterol", Science, Nov. 9, 2001, v. 294, 1354-1357.
Moya et al., "A Cell Culture System for Screening Human Serum for Ability to Promote Cellular Cholesterold Efflux", Arteriosclerosis and Thrombosis, vol. 14, issue 7, Jul. 1994, pp. 1056-1065.
Nakawatase et al., "Alzheimer's Disease and Related Dementias", Cecil's Text Book of Medicine, 2000, 21st Edition, 1, W.B. Saunders Company, 2042-2045.
Ngu , "Chronic Infections from the Perspective of Evolution: a Hypothesis", Medical Hypothesis, 1994, vol. 42, pp. 81-88.
Ngu , "Human Cancers and Viruses: A Hypothesis for Immune Destruction of Tumours Caused by Certain Enveloped Viruses Using Modified Viral Antigens", Medical Hypotheses, 1992, vol. 39, pp. 17-21.
Ngu , "The viral envelope in the evolution of HIV: a hypothetical approach to inducing an effective immune response to the virus", Medical Hypotheses, 1997, vol. 48, pp. 517-521.
Nissen et al., "Effect of Recombinant ApoA-1 Milano on Coronary Atherosclerosis in Patients with Acute Coronary syndromes", Journal of American Medical Association, 2003, v. 290, pp. 2292-2300.
Okazaki , "Improved High-Performance Liquid Chromatographic Method for the Determination of Apolipoproteins in Serum High-Density Lipoproteins", Journal of Chromatography B: Biomedical Sciences and Applications, vol. 430, Aug. 1988, pp. 135-142.
Osborne et al., "Delipidation of Plasma Lipoproteins", Methods in Enzymology, 1986, v. 128, pp. 213-222.
Parker et al., "Plasma high density lipoprotein is increased in man when low density lipoprotein (LDL) is lowered by LDL-pheresis", Proc. Natl. Acad. Sci. USA, Feb. 1986, vol. 82, pp. 771-781.
Paterno et al., "Reconstituted High-Density Lipoprotein Exhibits Neuroprotection in Two Rat Models of Stroke", Cerebrovasc Dis., Epub Dec. 29, 2003, 17, 2-2, 204-11(Abstract only).
Refolo et al., "Cholesterol Metabolism: A Potential Target for Alzheimer's Disease Therapy", Neuroscience Abstracts, vol. 27, issue 2, 2001, pp. 1518, (Abstract only).
Robern et al., "The Application of Sodium Deoxycholate and Sephacryl-200 for the Delipidation and Separation of High Density Lipoproteins", Experientia, 1982, 38, 437-439.
Ryan et al., "An improved Extraction Procedure for the Determination of Triglycerides and Cholesterol in Plasma or Serum", Clinical Chemistry, vol. 13, No. 9, Sep. 1967, pp. 769-772.
Rye et al., "Changes in the Size of Reconstituted High Density Liporoteins during Incubation with Cholesteryl Ester transfer protein: The Role of Apolipoproteins", Journal of Lipid Research, vol. 33, Feb. 1992, pp. 214-224.
Scanu et al., "Solubility in Aqueous Solutions of Ethanol of the Small Molecular Weight Peptides of the Serum Very Low Density and High Density Lipoproteins: Relevance to the Recovery Problem During Delipidation of Serum Lipoproteins", Anallytical Biochemistry, 1971, 44, 576-588.
Segrest et al., "A Detailed Molecular Belt Model for Apolipoprotein A-I in Discoidal High Density Lipoprotein", Journal of Biological Chemistry, Nov. 5, 1999, 274(45), 31755-31758.
Simons et al., "Cholesterol and Alzheimer's disease: Is there a link", Neurology, 2001, 57, 1089-1093.
Slater et al., "A Comparison of Delipidated Sera Used in Studies of Sterol Synthesis by Human Mononuclear Leukocytes", J. of Lipid Research, 1979, v. 20, 413-416.
Slater et al., "The Effect of Delipidated High Density Lipoprotein on Human Leukocyte Sterol Synthesis", Atherosclerosis, 1980, 35, 41-49.
Sviridov et al., "Dynamics of Reverse Cholesterol Transport: Protection against Atherosclerosis", Atherosclerosis, vol. 161, No. 2, Apr. 2002, pp. 245-254.
Tadey et al., "Chromatographic Techniques for the Isolation and Purification of Lipoproteins", Journal of Chromatography B, 1995, v. 672, pp. 237, 253.
Thompson et al., "Plasma Exchange in the Management of Homozygous Familial Hypercholesterolaemia", Lancet (LOS), 1975, 1, 1208-1211.
Tricerri et al., "Interaction of Apolipoprotein A-1 in Three Different Conformations with Palmitoyl Oleoyl Phosphatidylcholine Vesicles", Journal of Lipid Research, 2002, v. 43, pp. 187-197.
Walker et al., "Escape from Immune System", Nature, 2000, v. 407, pp. 313-134.
Williams et al., "Low Density Lipoprotein Receptor-independent Hepatic Uptake of a Synthetic, Cholesterol-Scavenging Lipoprotein: Implications for the Treatment of Receptor-Deficient Atherosclerosis", Proc. Natl. Acad. Scci. USA, 1988, 85:242-246.
Williams et al., "Uptake of Endogenous Cholesterol by a Synthetic Lipoprotein", Biochim. Biophys. Act., Feb. 12, 1986, v. 875(2), 183-194.
Wong et al., "Retention of Gangliosides in Serum Delipidated by Diisopropyl ether-1-butanol Extraction", Journal of Lipid Research, vol. 24(5), May 1983, pp. 666-669.
Wormser , "Lipids", PSC3110—Fall Semester 2002.
Yokoyama et al., "Selective Removal of Low Density Lipoprotein by Plasmapheresis in Familial Hypercholesterolemia", Arteriosclerosis, Thrombosis, and Vascular Biology, vol. 5, Nov. 1985, pp. 613-622.
Yoshidome et al., "Serum Amyloid A and P Protein Levels are Lowered by Dextran Sulfate Cellulose Low-Density Lipoprotein Apheresis", Artificial Organs, vol. 22, Issue 2, Feb. 1998, pp. 144-148.
Zetia, http://www/zetia.com/ezetimbeizetia/hcp/product_highlights/index.jsp, Zetia (ezetimibe), Jul. 18, 2003, pp. 1-2.
Zetia , "Zetia: Compliments Statin with a Unique Mechanism", http://www.zetia.com/ezetimibeizetia.hcp/mechanism_of actiontindex. jsp, Jul. 18, 2003, pp. 1-2.
Zhang et al., "Characterization of Phospholipids in a Pre-Alpha HDL: Selective Phospholipid Efflux with Apolipoprotein Al,-" Journal of Lipid Research, vol. 39, No. 8, Aug. 1998, pp. 1601-1607.
AHA Statistical Update, "Heart Disease and Stroke Statistics—2016 Update", Dec. 16, 2015.
Casserly et al, "Convergence of atherosclerosis and Alzheimer's disease: inflammation, cholesterol, and misfolded proteins", The Lancet, vol. 363, Apr. 3, 2004.
Radin, N. 1996 Neuromethods (vol. 7) Lipids and Related Compunds Protocol. pp. 1-61.

* cited by examiner

| | Plasma Type | Plasma Volumes | Solvent Type | %n-butanol or Solvent Ratio | Solvent to Plasma Ratio | Method of Mixing | Mixing Time | Method of Separation | Separation Time | Centrifugal Force | Results |
|---|---|---|---|---|---|---|---|---|---|---|---|
| Embodiment 1 | Human | 10mL | n-Butanol/DiPE | 0%-40% | 2:1 | Rocker Table | 5 Minutes | Gravity/Centrifuge | 5min/2min | 563 X G | % Lipids Remaining vs. % butanol |
| Embodiment 2 | Bovine | 2.5-10mL | n-Butanol/DiPE | 25% | 0.25-10 | Rocker Table | 5 Minutes | Gravity/Centrifuge | 5min/2min | 563 X G | % Lipids Remaining in Plasma vs. Solvent Ratio |
| Embodiment 3 | Human | 10mL | n-Butanol/DiPE | 25% | 2:1 | Rocker Table/Vortex | 0-300 Seconds | Gravity/Centrifuge | 5min/2min | 563 X G | % Lipids Remaining in Plasma vs. Mixing Time |
| Embodiment 4 | Human | 10mL | n-Butanol/DiPE | 25% | 2:1 | Rocker Table | 5 minutes | Gravity/Centrifuge | 5 min/2 min | 0-200 X G | % Lipid vs. Centrifuge Force |

FIG. 4

| Solvent Mix | Solvent Ratio | Plasma: Solvent Ratio | Mix Method | Time | Sep. Method |
|---|---|---|---|---|---|
| S:N | 95:5 | | | 1min. | CF |
| | | 1:2 | Rotation | 1min. | GS |
| | | 2:1 | Rotation | 1min. | GS |
| | | | | 2min. | CF |
| | | 1:1 | Rotation | 1min. | CF |
| | | | Vortex | 15sec. | CF |
| | | | Vortex | 15sec. | CF |
| D:N | 95:5 | 1:1 | Rotation | 1min. | CF |
| | | 1:2 | Vortex | 15sec. | CF |
| | | 2:1 | Vortex | 15sec. | CF |
| I | 100 | 1:1 | Vortex | 1min. | CF |
| I:N | 95:5 | 1:1 | Rotation | 1min. | CF |
| | | | Vortex | 15sec. | CF |
| | | 1:2 | Vortex | 15sec. | CF |
| | | 2:1 | Vortex | 15sec. | CF |
| N | 100 | 50:1 | Rotation | 2min. | CF |
| | | 100:1 | Rotation | 2min. | CF |
| S | 100 | 2:1 | Vortex | 1min. | CF |
| D:N | 99:1 | 1:1 | Rotation | 1min. | CF |
| D:N | 99:1 | 1:1 | Rotation | 1min. | GS |
| D:N | 97.5:2.5 | 1:1 | Rotation | 1min. | CF |
| | | 1:2 | Vortex | 15sec. | CF |
| | | 2:1 | Vortex | 15sec. | CF |
| D:N | 97.5:2.5 | 1:1 | Rotation | 1min. | GS |
| | | 1:2 | Vortex | 15sec. | GS |
| | | 2:1 | Vortex | 15sec. | GS |

FIG. 5

| Plasma | Solvents | Ratio | P:S | Volume | S Volume | Mix Method | Time | Separation | time (min) | Solvent Removal |
|---|---|---|---|---|---|---|---|---|---|---|
| normal | S:N | 95:5 | 1:2 | 25 | 50 | Vortex | 15sec | CF | 2 | Charcoal |
| lipemic IV | S:N | 95:5 | 1:2 | 25 | 50 | Vortex | 15sec | CF | 2 | Charcoal |
| normal | D | 100 | 1:1 | 25 | 25 | Vortex | 15sec | GS | 10 | Charcoal |
| lipemic IV | D | 100 | 1:1 | 25 | 25 | Vortex | 15sec | GS | 10 | Charcoal |

FIG. 6

SYSTEMS AND METHODS FOR PRIMING FLUID CIRCUITS OF A PLASMA PROCESSING SYSTEM

CROSS-REFERENCE

The present application relies on U.S. Provisional Patent Application No. 62/589,919, entitled "Systems and Methods for Causing Regression of Arterial Plaque" and filed on Nov. 22, 2017, for priority.

FIELD

The present invention generally relates to systems, apparatus and methods for removing lipids from HDL particles while leaving LDL particles substantially intact, via the extracorporeal treatment of blood plasma using either a single solvent or multiple solvents, in order to regress vulnerable arterial plaques, which is implicated in many disease states. More specifically, the presently disclosed inventions address the priming of the plasma processing system and the management of waste, particularly solvent waste, generated by the described treatment processes.

BACKGROUND

Familial Hypercholesterolemia (FH) is an inherited genetic autosomal dominant disease characterized by markedly elevated low density lipoprotein (LDL), tendon xanthomas, and premature coronary heart disease, caused by mutations of "FH genes," which include the LDL-receptor (LDLR), apolipoprotein B-100 (APOB) or proprotein convertase subtilisin/kexin type 9 (PCSK9). FH produces a clinically recognizable pattern that consists of severe hypercholesterolemia due to the accumulation of LDL in the plasma, cholesterol deposition in tendons and skin, as well as a high risk of atherosclerosis manifesting almost exclusively as coronary artery disease (CAD). In FH patients, this genetic mutation makes the liver unable to effectively metabolize (or remove) excess plasma LDL, resulting in increased LDL levels.

If an individual has inherited a defective FH gene from one parent, the form of FH is called Heterozygous FH. Heterozygous FH is a common genetic disorder, inherited in an autosomal dominant pattern, occurring in approximately 1:500 people in most countries. If the individual has inherited a defective FH gene from both parents, the form of FH is called Homozygous FH. Homozygous FH is very rare, occurring in about 1 in 160,000 to one million people worldwide, and results in LDL levels >700 mg/dl, 10 fold higher than the ideal 70 mg/dl level desired for patients with CVD. Due to the high LDL levels, patients with Homozygous FH have aggressive atherosclerosis (narrowing and blocking of blood vessels) and early heart attacks. This process starts before birth and progresses rapidly. It can affect the coronary arteries, carotid arteries, aorta, and aortic valve.

Heterozygous FH (HeFH) is normally treated with statins, bile acid sequestrants, or other lipid lowering agents that lower cholesterol levels, and/or by offering genetic counseling. Homozygous FH (HoFH) often does not respond adequately to medical therapy and may require other treatments, including LDL apheresis (removal of LDL in a method similar to dialysis), ileal bypass surgery to dramatically lower their LDL levels, and occasionally liver transplantation. A few medications have recently been approved for use by HoFH subjects. However, these medications lower LDL only, and modestly contribute to slowing, but not stopping, further progression of atherosclerosis. Additionally, these medications are known to have significant side-effects.

Cholesterol is synthesized by the liver or obtained from dietary sources. LDL is responsible for transferring cholesterol from the liver to tissues at different sites in the body. However, if LDL collects on the arterial walls, it undergoes oxidation caused by oxygen free radicals liberated from the body's chemical processes and interacts deleteriously with the blood vessels. The modified LDL causes white blood cells in the immune system to gather at the arterial walls, forming a fatty substance called plaque and injuring cellular layers that line blood vessels. The modified oxidized LDL also reduces the level of nitric oxide, which is responsible for relaxing the blood vessels and thereby allowing the blood to flow freely. As this process continues, the arterial walls slowly constrict, resulting in hardening of the arteries and thereby reducing blood flow. The gradual build-up of plaque can result in blockage of a coronary vessel and ultimately in a heart attack. The plaque build up can also occur in peripheral vessels such as the legs and this condition is known as peripheral arterial disease.

Obstructions can also appear in blood vessels that supply blood to the brain, which can result in ischemic strokes. The underlying condition for this type of obstruction is the development of fatty deposits lining the vessel walls. It is known that at least 2.7% of men and women over the age of 18 in the United States have a history of stroke. Prevalence of stroke is also known to be higher with increasing age. With the increase in the aging population, the prevalence of stroke survivors is projected to increase, especially among elderly women. A considerable portion of all strokes (at least 87%) are ischemic in nature.

Further, it has been shown that hypercholesterolemia and inflammation are two dominant mechanisms implicated in the development of atherosclerosis. There is significant overlap between vascular risk factors for both Alzheimer's disease and atherosclerosis. Inflammation has been implicated in Alzheimer's disease pathogenesis and it is suggested that abnormalities in cholesterol homeostasis may have a role as well. In addition, many of the contributory factors in atherogenesis also contribute to Alzheimer's disease. Specifically, in cell cultures, increased and decreased cholesterol levels promote and inhibit the formation of beta amyloid (Aβ) from Amyloid Precursor Protein (APP), respectively. Thus, the use of treatments with proven effects on the process of atherosclerosis may be one method for treating the progression of the Alzheimer's disease.

Another common cardiovascular disease that occurs due to development of atherosclerosis (hardening and narrowing of the arteries) within the elastic lining inside a coronary artery, is Coronary Artery Disease (CAD), also known as Ischemic Heart Disease (IHD). On the basis of a statistical data collected from 2009 to 2012, an estimated 15.5 million Americans ≥20 years of age have CAD. The total CAD prevalence in the United States is 6.2% of adults ≥20 years of age.

An acute decrease in blood flow in the coronary arteries may result in part of the heart muscle unable to function properly. This condition is known as Acute Coronary Syndrome (ACS). A conservative estimate for the number of hospital discharges with ACS in 2010 is 625,000.

In contrast to LDL, high plasma HDL levels are desirable because they play a major role in "reverse cholesterol transport", where the excess cholesterol is transferred from tissue sites to the liver where it is eliminated. Optimal total cholesterol levels are 200 mg/dl or below with a LDL cholesterol level of 160 mg/dl or below and a HDL-cholesterol level of 45 mg/dl for men and 50 mg/dl for women. Lower LDL levels are recommended for individuals with a history of elevated cholesterol, atherosclerosis or coronary artery disease. High levels of LDL increase the lipid content in coronary arteries resulting in formation of lipid filled plaques that are vulnerable to rupture. On the other hand, HDL has been shown to decrease the lipid content in the lipid filled plaques, reducing the probability of rupture. In the last several years, clinical trials of low density lipoprotein (LDL)—lowering drugs have definitively established that reductions in LDL are associated with a 30-45% decrease in clinical cardiovascular disease (CVD) events. CVD events include events occurring in diseases such as HoFH, HeFH, and peripheral arterial disease. Despite lowered LDL, however, many patients continue to have cardiac events. Low levels of HDL are often present in high risk subjects with CVD, and epidemiological studies have identified HDL as an independent risk factor that modulates CVD risk. In addition to epidemiologic studies, other evidence suggests that raising HDL would reduce the risk of CVD. There has been increasing interest in changing plasma HDL levels by dietary, pharmacological or genetic manipulations as a potential strategy for the treatment of CVD including HoFH, HeFH, Ischemic stroke, CAD, ACS, and peripheral arterial disease and for treating the progression of Alzheimer's Disease.

The protein component of LDL, known as apolipoprotein-B (ApoB), and its products, comprise atherogenic elements. Elevated plasma LDL levels and reduced HDL levels are recognized as primary causes of coronary disease. ApoB is in highest concentration in LDL particles and is not present in HDL particles. Apolipoprotein A-I (ApoA-I) and apolipoprotein A-II (ApoA-II) are found in HDL. Other apolipoproteins, such as ApoC and its subtypes (C-I, C-II and C-III), ApoD, and ApoE are also found in HDL. ApoC and ApoE are also observed in LDL particles.

Numerous major classes of HDL particles including HDL2b, HDL2a, HDL3a, HDL3b and HDL3 have been reported. Various forms of HDL particles have been described on the basis of electrophoretic mobility on agarose as two major populations, a major fraction with α-HDL mobility and a minor fraction with migration similar to VLDL. This latter fraction has been called pre-β HDL and these particles are the most efficient HDL particle subclass for inducing cellular cholesterol efflux.

The HDL lipoprotein particles are comprised of ApoA-I, phospholipids and cholesterol. The pre-β HDL particles are considered to be the first acceptors of cellular free cholesterol and are essential in eventually transferring free and esterified cholesterol to α-HDL. Pre-β HDL particles may transfer cholesterol to α-HDL or be converted to α-HDL. The alpha HDL transfers cholesterol to the liver, where excess cholesterol can be removed from the body.

HDL levels are inversely correlated with atherosclerosis and coronary artery disease. Once cholesterol-carrying α-HDL reaches the liver, the α-HDL particles divest of the cholesterol and transfer the free cholesterol to the liver. The α-HDL particles (divested of cholesterol) are subsequently converted to pre-β HDL particles and exit the liver, which then serve to pick up additional cholesterol within the body and are converted back to α-HDL, thus repeating the cycle. Accordingly, what is needed is a method to decrease or remove cholesterol from these various HDL particles, especially the α-HDL particles, so that they are available to remove additional cholesterol from cells.

Hyperlipidemia (or abnormally high concentration of lipids in the blood) may be treated by changing a patient's diet. However, diet as a primary mode of therapy requires a major effort on the part of patients, physicians, nutritionists, dietitians, and other health care professionals and thus undesirably taxes the resources of health professionals. Another negative aspect of this therapy is that its success does not rest exclusively on diet. Rather, success of dietary therapy depends upon a combination of social, psychological, economic, and behavioral factors. Thus, therapy based only on correcting flaws within a patient's diet, is not always successful.

In instances when dietary modification has been unsuccessful, drug therapy has been used as adjunctive therapy. Such therapy has included use of commercially available hypolipidemic drugs administered alone or in combination with other therapies as a supplement to dietary control. These drugs, called statins, include lovastatin, pravastatin, simvastatin, fluvastatin, atorvastatin, and cerivastatin. Statins are particularly effective for lowering LDL levels and are also effective in the reduction of triglycerides, apparently in direct proportion to their LDL-lowering effects. Statins raise HDL levels, but to a lesser extent than other anti-cholesterol drugs. Statins also increase nitric oxide, which, as described above, is reduced in the presence of oxidized LDL.

Bile acid resins, another drug therapy, work by binding with bile acid, a substance made by the liver using cholesterol as one of the primary manufacturing components. Because the drugs bind with bile acids in the digestive tract, they are then excreted with the feces rather than being absorbed into the body. The liver, as a result, must take more cholesterol from the circulation to continue constructing bile acids, resulting in an overall decrease in LDL levels.

Nicotinic acid, or niacin, also known as vitamin B3, is effective in reducing triglyceride levels and raising HDL levels higher than any other anti-cholesterol drug. Nicotinic acid also lowers LDL-cholesterol.

Fibric acid derivatives, or fibrates, are used to lower triglyceride levels and increase HDL when other drugs ordinarily used for these purposes, such as niacin, are not effective.

Probucol lowers LDL-cholesterol levels, however, it also lowers HDL levels. It is generally used for certain genetic disorders that cause high cholesterol levels, or in cases where other cholesterol-lowering drugs are ineffective or cannot be used.

PCSK9s lower LDL-cholesterol levels via increasing the cellular level of LDL receptors that reside in the liver.

Hypolipidemic drugs have had varying degrees of success in reducing blood lipid; however, none of the hypolipidemic drugs successfully treats all types of hyperlipidemia. While some hypolipidemic drugs have been fairly successful, the medical community has found little conclusive evidence that hypolipidemic drugs cause regression of atherosclerosis. In addition, all hypolipidemic drugs have undesirable side effects. As a result of the lack of success of dietary control, drug therapy and other therapies, atherosclerosis remains a major cause of death in many parts of the world.

New therapies have been used to reduce the amount of lipid in patients for whom drug and diet therapies were not sufficiently effective. For example, extracorporeal procedures like plasmapheresis and LDL-apheresis have been employed and are shown to be effective in lowering LDL.

Plasmapheresis therapy or plasma exchange therapy, involves replacing a patient's plasma with donor plasma or more usually a plasma protein fraction. Plasmapheresis is a process whereby the blood plasma is removed from blood cells by a cell separator. The separator works either by spinning the blood at high speed to separate the cells from the fluid or by passing the blood through a membrane with pores so small that only the fluid component of the blood can pass through. The cells are returned to the person undergoing treatment, while the plasma is discarded and replaced with other fluids.

This treatment has resulted in complications due to the introduction of foreign proteins and transmission of infectious diseases. Further, plasmapheresis has the disadvantage of non-selective removal of all serum lipoproteins, such as VLDL, LDL, and HDL. Moreover, plasmapheresis can result in several side effects including allergic reactions in the form of fever, chills, and rash and possibly even anaphylaxis.

As described above, it is not desirable to remove HDL, which is secreted from both the liver and the intestine as nascent, disk-shaped particles that contain cholesterol and phospholipids. HDL is believed to play a role in reverse cholesterol transport, which is the process by which excess cholesterol is removed from tissues and transported to the liver for reuse or disposal in the bile.

In contrast to plasmapheresis, the LDL-apheresis procedure selectively removes ApoB containing cholesterol, such as LDL, while retaining HDL. Several methods for LDL-apheresis have been developed. These techniques include absorption of LDL in heparin-agarose beads, the use of immobilized LDL-antibodies, cascade filtration absorption to immobilize dextran sulfate, and LDL precipitation at low pH in the presence of heparin. Each method described above is effective in removing LDL. This treatment process has disadvantages, however, including the failure to positively affect HDL or to cause a metabolic shift that can enhance atherosclerosis and other cardiovascular diseases. LDL apheresis, as its name suggests, merely treats LDL in patients with severe hyperlipidemia.

Yet another method of achieving a reduction in plasma cholesterol in homozygous familial hypercholesterolemia, heterozygous familial hypercholesterolemia and patients with acquired hyperlipidemia is an extracorporeal lipid elimination process, referred to as cholesterol apheresis. In cholesterol apheresis, blood is withdrawn from a patient, the plasma is separated from the blood, and the plasma is mixed with a solvent mixture. The solvent mixture extracts lipids from the plasma. Thereafter, the delipidated plasma is recombined with the patient's blood cells and returned to the patient. Using this procedure, however, results in a modification of the LDL particles, such that the modified LDL particles could result in increased intensity of the heart disease. At the same time, this process also resulted in further delipidation of the HDL particles.

U.S. Pat. Nos. 7,361,739; 7,375,191; 7,393,826; 8,030,281; 8,048,015; 8,268,787; and 8,637,460, assigned to the Applicant of the present specification, and herein incorporated by reference in their entirety, all describe "systems, apparatus and methods for creating derivatives of at least one form of HDL without substantially affecting LDL. These derivatives of HDL are particles with reduced lipid content, particularly reduced cholesterol content. These particles have the capacity to bind cholesterol and are administered to a patient to enhance cellular cholesterol efflux and reduce cholesterol levels in cells, tissues, organs, and blood vessels".

U.S. Pat. No. 7,375,191, assigned to the Applicant of the present specification, and herein incorporated by reference in its entirety, describes "[a] composition comprising substantially unmodified low density lipoprotein particles and a particle derivative of high density lipoprotein particles comprising lipids, apolipoprotein A-1 and at least one of apolipoprotein C-III, apolipoprotein D or apolipoprotein E, wherein the lipids include phospholipids, wherein the composition is formed by an extracorporeal process comprising exposing a biological fluid comprising low density lipoprotein particles and high density lipoprotein particles to a lipid removing agent, wherein the substantially unmodified low density lipoprotein particles are substantially unmodified as compared to the low density lipoprotein particles in the biological fluid prior to exposure of the biological fluid to the lipid removing agent, and wherein the particle derivative of the high density lipoprotein particles has a lower content of at least one of the phospholipids or cholesterol than the high density lipoprotein particles in the biological fluid prior to exposure of the biological fluid to the lipid removing agent."

U.S. Pat. No. 7,361,739, assigned to the Applicant of the present specification, and herein incorporated by reference in its entirety, describes "[a] composition comprising a particle derivative of an HDL particle and a substantially unaffected LDL particle, the particle derivative comprising a lipid bilayer comprising phospholipids and a protein shell comprising apolipoprotein A-1 and apolipoprotein A-2, and at least one of apolipoprotein C-III, apolipoprotein D or apolipoprotein E, wherein the particle derivative has a lower content of at least one of phospholipids or cholesterol than the HDL particle, and wherein a content of at least one of phospholipids or cholesterol in the substantially unaffected LDL particle is substantially similar to a content of at least one of phospholipids or cholesterol, respectively, in an LDL particle; and wherein the composition is obtained extracorporeally."

U.S. Pat. No. 7,393,826, assigned to the Applicant of the present specification, and herein incorporated by reference in its entirety, describes "[a] selectively delipidated biological fluid comprising a particle derivative of an HDL particle and a substantially unmodified LDL particle as compared to an LDL particle, wherein the selectively delipidated biological fluid is formed by an extracorporeal selective delipidation process comprising the step of exposing a biological fluid comprising the HDL particle and the LDL particle to a lipid removing agent, wherein the particle derivative of the HDL particle comprises a lipid bilayer comprising phospholipids and a protein shell comprising apolipoprotein A-1, apolipoprotein A-2, and at least one of apolipoprotein C-III, apolipoprotein D or apolipoprotein E, and wherein a cholesterol content of the HDL particle derivative is lower than a cholesterol content of the HDL particle."

U.S. Pat. No. 8,030,281, assigned to the Applicant of the present specification, and herein incorporated by reference in its entirety, describes "[a] method for making a particle derivative of at least one form of high density lipoprotein wherein the particle derivative comprises a protein shell and lipid comprising the steps of: a. connecting a patient to a device for withdrawing blood; b. withdrawing blood containing blood cells from the patient; c. separating the blood cells from the blood to yield a blood fraction containing high density lipoprotein and low density lipoprotein; d. separating the low density lipoprotein from the blood fraction; e. mixing the blood fraction with a solvent which removes lipid associated with the high density lipoprotein to yield a mixture of lipid, the solvent, and the particle derivative; and, f. separating the particle derivative, wherein the particle derivative comprises apolipoprotein A1 and phospholipid, from the lipid and the solvent."

U.S. Pat. No. 8,048,015, assigned to the Applicant of the present specification, and herein incorporated by reference in its entirety, describes "[a] method of modifying a protein distribution in a fluid, wherein the protein distribution has a first state, the first state having alpha high density lipoproteins and pre-beta high density lipoproteins, comprising the steps of: exposing the fluid to a lipid removing agent wherein the exposure modifies the protein distribution from the first state into a second state, the second state having an increased concentration of pre-beta high density lipoproteins relative to the first state; and, removing the lipid removing agent from the fluid, wherein the lipid removing agent comprises sevoflurane."

U.S. Pat. No. 8,268,787, assigned to the Applicant of the present specification, and herein incorporated by reference in its entirety, describes "[a] method for enhancing cellular cholesterol efflux in a patient, comprising administering to the patient a composition comprising a particle derivative of at least one form of high density lipoprotein, wherein the particle derivative comprises a protein shell and lipid and is obtained by a process comprising the steps of: a. connecting a patient to a device for withdrawing blood; b. withdrawing blood containing blood cells from the patient; c. separating the blood cells from the blood to yield a blood fraction containing high density lipoprotein and low density lipoprotein; d. separating the low density lipoprotein from the blood fraction; e. mixing the blood fraction with a solvent which removes lipid associated with the high density lipoprotein to yield a mixture of lipid, the solvent, and the particle derivative; and, f. separating the particle derivative from the lipid and the solvent, wherein the particle derivative comprises apolipoprotein A1 and phospholipid, and wherein the particle derivative has a reduced lipid content as compared to the high density lipoprotein particle that does not have the solvent treatment."

U.S. Pat. No. 8,637,460, assigned to the Applicant of the present specification, and herein incorporated by reference in its entirety, describes "[a] method of modifying a protein distribution in a fluid, wherein the protein distribution has a first state, the first state having alpha high density lipoproteins and pre-beta high density lipoproteins, comprising the steps of: exposing the fluid to a lipid removing agent wherein the exposure modifies the protein distribution from the first state into a second state, the second state having an increased concentration of pre-beta high density lipoproteins relative to the first state; and, removing the lipid removing agent from the fluid, wherein the lipid removing agent comprises a combination of sevoflurane with at least one of n-butanol, hexanol, ethanol, isoflurane, diisopropyl ether or trifluoroethane."

Further, U.S. patent application Ser. Nos. 16/003,926 and 15/876,808 assigned to the Applicant of the present specification, are also herein incorporated by reference in their entirety.

Vigorous multi-stage solvent exposure and extraction can have several drawbacks. It may be difficult to remove a sufficient amount of solvents from the delipidated plasma in order for the delipidated plasma to be safely returned to a patient. What is also needed is a system and a method to process the plasma and solvent mixture and consequently derive delipidated plasma that can be provided to a patient, in chronic diseases.

What are also needed are systems and methods that provide a simple and improved priming and waste management process. More specifically, what is needed is a system and method that is capable of processing both solvent waste and prime waste separately so that the waste streams can be treated and disposed of appropriately.

SUMMARY

The following embodiments and aspects thereof are described and illustrated in conjunction with systems, tools and methods, which are meant to be exemplary and illustrative, not limiting in scope.

The present specification discloses a method of priming a plasma processing system comprising at least a first fluid flow path, a second fluid flow path, third fluid flow path, and a fourth fluid flow path, comprising: flushing a first fluid circuit, wherein the first fluid circuit is defined by a source of a first fluid, a first valve positioned between the source of the first fluid and the first fluid flow path, a second valve positioned between the first fluid flow path and the second fluid flow path, a first pump positioned between the second fluid flow path and the third fluid flow path, and a first waste container in fluid communication with the third fluid flow path; closing the second valve, thereby preventing a flow of fluid to the second fluid flow path, third fluid flow path, and first waste container; closing the first valve, thereby preventing a flow of the first fluid to the first fluid flow path from the source of the first fluid; opening a third valve, wherein the third valve is positioned between the first fluid flow path and the fourth fluid flow path; opening a fourth valve, wherein the fourth valve is positioned between a source of a second fluid and the first fluid flow path; and opening the second valve, thereby enabling a flow of fluid to the second fluid flow path, third fluid flow path, and first waste container.

Optionally, the first fluid is saline.

Optionally, the second fluid is saline.

Optionally, the first fluid circuit is not in fluid communication with a source of plasma, a source of solvent, or an output plasma container.

Optionally, the plasma processing system further comprises a connector tube positioned along the second fluid flow path. Optionally, the method further comprises, after opening the second valve, clamping the second fluid flow path and removing the connector tube. Optionally, the method further comprises, after removing the connector tube, inserting a solvent extraction device in place of the removed connector tube. Optionally, the solvent extraction device is a charcoal column.

Optionally, plasma processing system further comprises a fifth valve positioned between the third fluid flow path and the first waste container.

Optionally, the fourth fluid flow path is in fluid communication with a separator.

The present specification also discloses a method of priming a plasma processing system comprising at least a first fluid flow path, a second fluid flow path, third fluid flow path, and a fourth fluid flow path, comprising: flushing a first fluid circuit, wherein the first fluid circuit is defined by a source of a first fluid, a first valve positioned between the source of the first fluid and the first fluid flow path, a second valve positioned between the first fluid flow path and the second fluid flow path, a first pump positioned between the second fluid flow path and the third fluid flow path, and a first waste container in fluid communication with the third fluid flow path; and flushing a second fluid circuit, wherein the second fluid circuit is defined by a source of a second fluid, a third valve, wherein the third valve is positioned between the first fluid flow path and the fourth fluid flow path, and a fourth valve, wherein the fourth valve is positioned between a source of a second fluid and the first fluid flow path, by closing the second valve, thereby preventing a flow of fluid to the second fluid flow path, third fluid flow path, and first waste container, closing the first valve, thereby preventing a flow of the first fluid to the first fluid flow path from the source of the first fluid, opening the third valve, and opening the fourth valve.

Optionally, the first fluid is saline and the second fluid is saline.

Optionally, the first fluid circuit is not in fluid communication with a source of plasma, a source of solvent, or an output plasma container.

Optionally, the plasma processing system further comprises a connector tube positioned along the second fluid flow path.

Optionally, the method further comprises, after closing the second valve, waiting a period of time and then opening the second valve, thereby enabling a flow of fluid to the second fluid flow path, third fluid flow path, and first waste container.

Optionally, the method further comprises, after opening the second valve, clamping the second fluid flow path and removing the connector tube. Optionally, the method further comprises, after removing the connector tube, inserting a solvent extraction device in place of the removed connector tube. Optionally, the solvent extraction device is a charcoal column.

Optionally, the plasma processing system further comprises a fifth valve positioned between the third fluid flow path and the first waste container.

Optionally, the fourth fluid flow path is in fluid communication with a separator.

The present specification also discloses a method for treating plasma using an apparatus to treat the plasma with a solvent, the method comprising: configuring the apparatus to separate a solvent waste and a prime waste; priming the apparatus with a priming fluid, the priming resulting in priming waste, wherein the priming waste is collected in a container configured to collect prime waste; installing a solvent extraction device within the apparatus; priming the apparatus with the solvent extraction device, the priming resulting in priming waste, wherein the priming waste is collected in the container configured to collect prime waste; introducing the plasma and the solvent in to a mixing device; mixing the plasma and the solvent; separating the plasma and the solvent, wherein the solvent is removed from the plasma into a container configured to collect solvent waste; and extracting remaining solvent from the plasma by transporting the separated plasma through the solvent extraction device.

Optionally, the solvent is at least one or more of a combination of n-butanol, ethyl acetate, dichloromethane, chloroform, isoflurane, sevoflurane (1,1, 1,3, 3,3-hexafluoro-2-(fluoromethoxy) propane-d3), perfluorocyclohexanes, trifluoroethane, and cyclofluorohexanol.

Optionally, the solvent is a lipid removing agent which removes lipids to yield a mixture of lipid, the lipid removing agent, modified high density lipoprotein, and the low density lipoprotein, wherein the modified high density lipoprotein is a delipidated high density lipoprotein.

Optionally, separating the plasma and the solvent comprises separating the modified high density lipoprotein and the low density lipoprotein from the lipid and the lipid removing agent.

Optionally, the step of separating the plasma and the solvent comprises using gravity.

Optionally, configuring the apparatus to separate a solvent waste and a prime waste comprises configuring a first waste container to collect solvent waste and a second waste container, separate from the first waste container, to collect prime waste.

Optionally, priming the apparatus with a priming fluid further comprises attaching a prime connector tube in the apparatus, wherein the prime connector tube is replaced by the solvent extraction device.

The present specification also discloses a method of using an apparatus to modify protein distribution in a fluid, wherein the method comprises: priming the apparatus with a priming fluid, the priming resulting in priming waste, wherein the priming waste is collected in a second waste container configured to collect prime waste; installing a solvent extraction device within the apparatus; priming the apparatus with the solvent extraction device, the priming resulting in priming waste, wherein the priming waste is collected in the second container; inputting a plasma in to a first fluid container; opening a first valve to direct flow from the first fluid container to a mixing device; inputting a solvent in to a second fluid container; opening a second valve to direct flow from the second fluid container to the mixing device; mixing the plasma and the solvent in the mixer for a first predetermined period of time; after the first predetermined period of time, opening a third valve to direct the plasma and the solvent mixture to a funnel-shaped bag separator; separating the plasma and the solvent in the separator for a second predetermined period of time; after the second predetermined period of time, opening a fourth valve to direct flow of separated solvent from the separator in to a first waste container configured to collect solvent waste; opening a fifth valve to direct flow of separated plasma from the separator in to the solvent extraction device; closing a sixth valve to inhibit flow of separated plasma from the solvent extraction device in to the second waste container; and opening a seventh valve to direct flow of separated plasma from the solvent extraction device in to a third fluid container configured to collect separated plasma.

Optionally, the opening the third valve to direct the plasma and the solvent mixture to the funnel-shaped bag separator results in gravity-directed flow of the plasma and the solvent mixture.

Optionally, the method further comprises pumping the priming fluid to direct flow of the priming fluid towards the second container, and pumping the separated plasma to direct flow of the separated plasma in to the solvent extraction device and the third fluid container.

Optionally, opening the fourth valve to direct flow of separated solvent from the separator comprises directing the flow through a cone-shaped bottom of the separator.

Optionally, the solvent extraction device is a charcoal column.

The present specification also discloses a method for mixing a plasma and a solvent in a mixing device, to modify protein distribution in the plasma, the method comprising: introducing a first volume of the plasma in to the mixing device, wherein said mixing device comprises at least one of a mixing bag, a mixer and a platform positioned above the mixer for said mixing bag to be placed upon; introducing a second volume of the solvent in to the mixing device; and mixing the first volume of the plasma and the second volume of the solvent in the mixing device, wherein the mixing device has a set of features; and varying at least one of the first volume, the second volume, the plasma, the solvent, the mixing device, and the set of features of the mixing device, to vary the extent of modification of protein distribution in the plasma.

Optionally, varying the mixing device comprises using a mixer that is one of an orbital mixer, a vortex mixer, a rotating table mixer, and a coiled tube mixer.

Optionally, varying the mixing device comprises varying an amount of energy applied to the mixer.

Optionally, varying the mixing device comprises varying a shape of the mixing bag.

Optionally, varying the mixing device comprises varying an angle at which the platform is positioned.

Optionally, varying the mixing device comprises varying a speed of operation of the mixer.

Optionally, a duration of the mixing is varied.

Optionally, the varying of the first volume and of the second volume comprises varying a ratio of the first volume to the second volume.

Optionally, varying the plasma comprises selecting one of a human plasma, a bovine plasma, a normal plasma, and a lipemic IV plasma.

Optionally, a ration of the constituents of the solvent is varied.

Optionally, a ration of the plasma to solvent is varied.

The aforementioned and other embodiments of the present specification shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 4 is a table showing the effect on the reduction of lipids resulting from variation in different chemical and mechanical parameters involved in implementing various embodiments in accordance with the present specification;

FIG. 5 is a table listing another exemplary set of variables that affect the delipidation process and outcome;

FIG. 6 is a table providing another exemplary set of variables that may be used for normal plasma and lipemic IV plasma using different solvents and different methods of separation;

DETAILED DESCRIPTION

Figure 1:
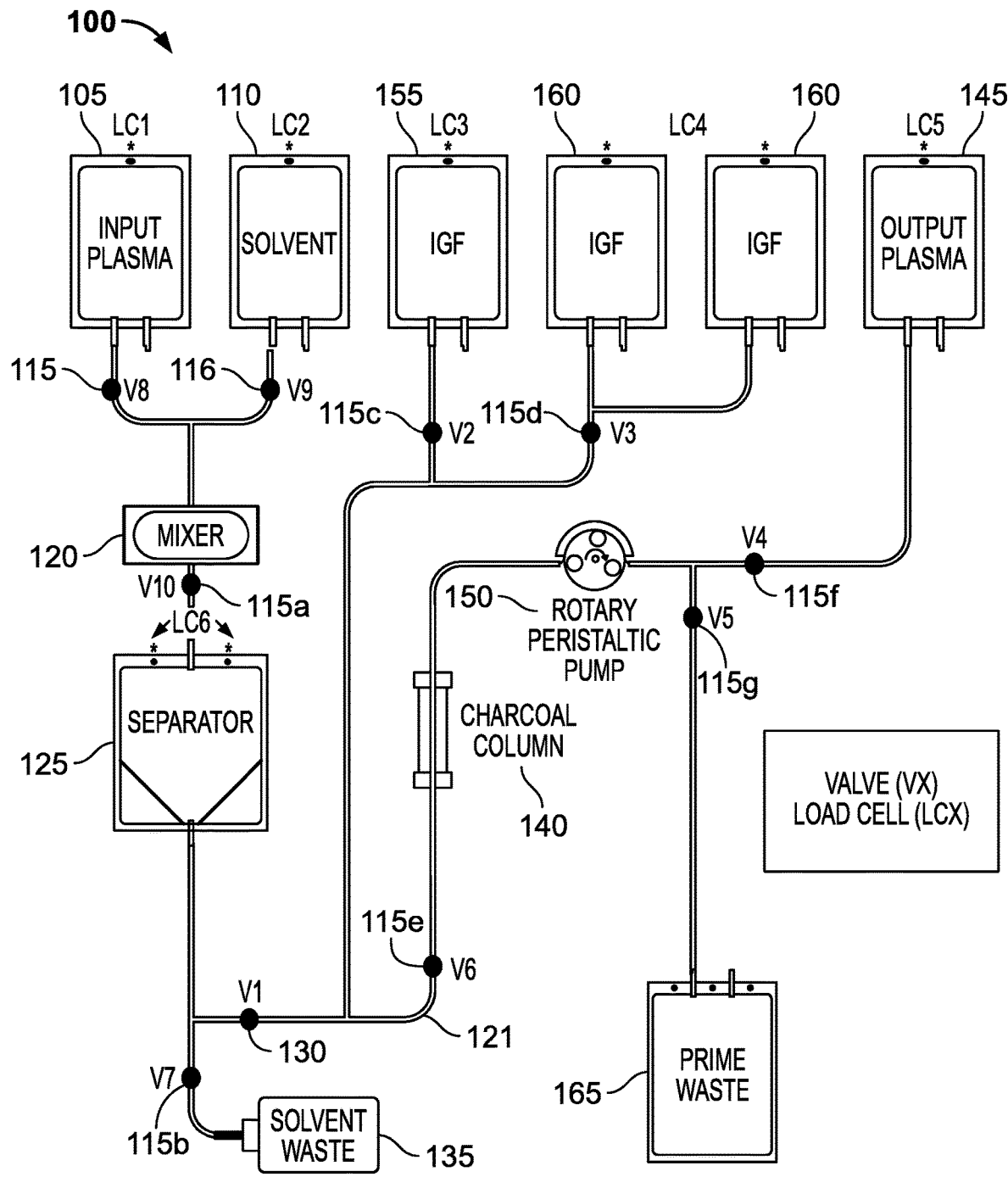
FIG. 1 is a schematic representation of a prior art system comprising a plurality of components used in accordance with some embodiments of the present specification to achieve the processes disclosed herein.

In some embodiments, the present specification is directed towards systems, apparatuses and methods for removing lipid from α-High Density Lipoprotein (α-HDL) particles derived primarily from plasma of the patient thereby creating modified HDL particles (also referred to as delipidated HDL) with reduced lipid content, particularly reduced cholesterol content. Embodiments of the present specification create these modified HDL particles with reduced lipid content without substantially modifying LDL particles. Embodiments of the present specification modify original α-HDL particles (present in delipidated plasma) to yield modified HDL particles that have an increased concentration of pre-β HDL relative to the original HDL. The modified HDL, with a concentrated solution of pre-β HDL is administered to the patient to enhance cellular cholesterol efflux and treat cardiovascular diseases and/or other lipid-associated diseases.

The treatment processes of the present specification renders the methods and systems of the present specification more effective in treating cardiovascular diseases including Homozygous Familial Hypercholesterolemia (HoFH), Heterozygous Familial Hypercholesterolemia (HeFH), Ischemic stroke, Coronary Artery Disease (CAD), Acute Coronary Syndrome (ACS), peripheral arterial disease (PAD), Renal Arterial Stenosis (RAS), and for treating the progression of Alzheimer's Disease.

Embodiments of the present specification provide systems and methods to achieve the above objectives. Systems and methods are provided where plasma and solvent(s) are introduced into a specially designed mixing bag in precise quantities and volumetric ratios. The solvent and plasma are then mixed in an orbital fashion for a prescribed period, resulting in delipidation. The mixture is then drained into a separator bag. Each batch is mixed and drained into the separator bag until the input plasma is fully processed. When the separator bag reaches capacity, excess solvent is drained to a solvent waste bag.

The timed suspension in the separator bag separates the plasma and solvent into distinct fractions so the solvent can be drained into the solvent waste bag. Some solvent, however, remains dissolved in the plasma. This residual solvent is substantially removed by passing the plasma through a specially-designed charcoal column. The output plasma contains selectively delipidated HDL with substantially unchanged or undelipidated LDL.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

The term "fluid" may be defined as fluids from animals or humans that contain lipids or lipid containing particles, fluids from culturing tissues and cells that contain lipids and fluids mixed with lipid-containing cells. For purposes of this invention, decreasing the amount of lipids in fluids includes decreasing lipids in plasma and particles contained in plasma, including but not limited to HDL particles. Fluids include, but are not limited to: biological fluids; such as blood, plasma, serum, lymphatic fluid, cerebrospinal fluid, peritoneal fluid, pleural fluid, pericardial fluid, various fluids of the reproductive system including, but not limited to, semen, ejaculatory fluids, follicular fluid and amniotic fluid; cell culture reagents such as normal sera, fetal calf serum or serum derived from any animal or human; and immunological reagents, such as various preparations of antibodies and cytokines from culturing tissues and cells, fluids mixed with lipid-containing cells, and fluids containing lipid-containing organisms, such as a saline solution containing lipid-containing organisms. A preferred fluid treated with the methods of the present invention is plasma. Arrows on the tubing segments in the figures represent fluid flow or the movement of fluid while the absence of arrows represents no fluid flow or movement. Patterns within the tubing segments in the figures represent fluid within the tubing while the absence of patterns represents no fluid within that segment of tubing.

The term "lipid" may be defined as any one or more of a group of fats or fat-like substances occurring in humans or animals. The fats or fat-like substances are characterized by their insolubility in water and solubility in organic solvents. The term "lipid" is known to those of ordinary skill in the art and includes, but is not limited to, complex lipid, simple lipid, triglycerides, fatty acids, glycerophospholipids (phospholipids), true fats such as esters of fatty acids, glycerol, cerebrosides, waxes, and sterols such as cholesterol and ergosterol.

The term "extraction solvent" may be defined as one or more solvents used for extracting lipids from a fluid or from particles within the fluid. This solvent enters the fluid and remains in the fluid until removed by other subsystems. Suitable extraction solvents include solvents that extract or dissolve lipid, including but not limited to phenols, hydrocarbons, amines, ethers, esters, alcohols, halohydrocarbons, halocarbons, and combinations thereof. Examples of suitable extraction solvents are ethers, esters, alcohols, halohydrocarbons, or halocarbons which include, but are not limited to di-isopropyl ether (DIPE), which is also referred to as isopropyl ether, diethyl ether (DEE), which is also referred to as ethyl ether, lower order alcohols such as butanol, especially n-butanol, ethyl acetate, dichloromethane, chloroform, isoflurane, sevoflurane (1,1, 1,3, 3,3-hexafluoro-2-(fluoromethoxy) propane-d3), perfluorocyclohexanes, trifluoroethane, cyclofluorohexanol, and combinations thereof.

The term "patient" refers to animals and humans, which may be either a fluid source to be treated with the methods of the present invention or a recipient of derivatives of HDL particles and or plasma with reduced lipid content.

The term "HDL particles" encompasses several types of particles defined based on a variety of methods such as those that measure charge, density, size and immuno-affinity, including but not limited to electrophoretic mobility, ultracentrifugation, immunoreactivity and other methods known to one of ordinary skill in the art. Such HDL particles include but are not limited to the following: α-HDL, pre-β HDL (including pre--1 HDL, pre-β2 HDL and pre-β3HDL), HDL2 (including HDL2a and HDL2b), HDL3, VHDL, LpA-I, LpA-II, LpA-I/LpA-II (for a review see Barrans et al., Biochemica Biophysica Acta 1300; 73-85,1996).

Accordingly, practice of the methods of the present invention creates modified HDL particles. These modified derivatives of HDL particles may be modified in numerous ways including but not limited to changes in one or more of the following metabolic and/or physico-chemical properties (for a review see Barrans et al., Biochemica Biophysica Acta 1300; 73-85,1996); molecular mass (kDa); charge; diameter; shape; density; hydration density; flotation characteristics; content of cholesterol; content of free cholesterol; content of esterified cholesterol; molar ratio of free cholesterol to phospholipids; immuno-affinity; content, activity or helicity of one or more of the following enzymes or proteins: Apo-AI, Apo-AII, ApoD, ApoE, ApoJ, ApoA-IV, cholesterol ester transfer protein (CETP), lecithin; cholesterol acyltransferase (LCAT); capacity and/or rate for cholesterol binding, capacity and/or rate for cholesterol transport.

The terms "modified high density lipoprotein" and "delipidated high density lipoprotein" may be used interchangeably and refer to reduced lipid blood products, and in particular, high density lipoproteins having a reduced lipid content, that may be contained within the resultant plasma once a delipidation process has been performed. Similarly, the term "treated plasma" refers to the resultant plasma once a delipidation process has been performed.

FIG. 1 illustrates an exemplary prior art system and its components used to achieve the methods of the present specification. The figure depicts an exemplary basic component flow diagram defining elements of the HDL modification system 100. Embodiments of the components of system 100 are utilized after obtaining a blood fraction from a patient or another individual (donor). The plasma, separated from the blood is brought in a sterile bag to system 100 for further processing. The plasma may be separated from blood using a known plasmapheresis device. The plasma may be collected from the patient into a sterile bag using standard apheresis techniques. The plasma is then brought in the form of a fluid input to system 100 for further processing. In embodiments, system 100 is not connected to the patient at any time and is a discrete, stand-along system for delipidating plasma. The patient's plasma is processed by system 100 and brought back to the patient's location to be reinfused back into the patient. In alternate embodiments, the system may be a continuous flow system that is connected to the patient in which both plasmapheresis and delipidation are performed in an excorporeal, parallel system and the delipidated plasma product is returned to the patient.

A fluid input 105 (containing blood plasma) is provided and connected via tubing to a mixing device 120. A solvent input 110 is provided and also connected via tubing to mixing device 120. In embodiments, valves 115, 116 are used to control the flow of fluid from fluid input 105 and solvent from solvent input 110 respectively. It should be appreciated that the fluid input 105 contains any fluid that includes HDL particles, including plasma having LDL particles or devoid of LDL particles, as discussed above. It should further be appreciated that solvent input 110 can include a single solvent, a mixture of solvents, or a plurality of different solvents that are mixed at the point of solvent input 110. While depicted as a single solvent container, solvent input 110 can comprise a plurality of separate solvent containers. Embodiments of types of solvents that may be used are discussed subsequently.

Mixer 120 mixes fluid from fluid input 105 and solvent from solvent input 110 to yield a fluid-solvent mixture. In some embodiments, mixer 120 is capable of using a shaker bag mixing method with the input fluid and input solvent in a plurality of batches, such as 1, 2, 3 or more batches. In alternative embodiments, other known methods of mixing are utilized. Once formed, the fluid-solvent mixture is directed, through tubing and controlled by at least one valve 115a, to a separator 125. In an embodiment, separator 125 is capable of performing bulk solvent separation through gravity separation in a funnel-shaped bag.

In separator 125, the fluid-solvent mixture separates into a first layer and second layer. The first layer comprises a mixture of solvent and lipid that has been removed from the HDL particles. Typically, the solvent is heavier than the plasma and therefore the solvent settles at the bottom of separator 125, and the delipidated plasma is at the top. In embodiments, the density/specific gravity of solvent is approximately 1.5 times greater than that of the plasma fluid. In embodiments, separator 125 is conical or V-shaped. Once the solvent settles at the bottom, it can be easily drained from separator 125 while the plasma fluid containing HDL particles is retained. The first layer is transported through a valve 115b to a first waste container 135. The second layer comprises a mixture of residual solvent, modified HDL particles, and other elements of the input fluid. One of ordinary skill in the art would appreciate that the composition of the first layer and the second layer would differ based upon the nature of the input fluid. Once the first and second layers separate in separator 125, the second layer is transported through tubing to a solvent extraction device 140. In an embodiment, a pressure sensor (not shown) and valve 130 is positioned in the flow stream to control the flow of the second layer to solvent extraction device 140.

The opening and closing of valves 115, 116 to enable the flow of fluid from input containers 105, 110 may be timed using mass balance calculations derived from weight determinations of the fluid inputs 105, 110, and separator 125. For example, valve 115b between separator 125 and first waste container 135 and valve 130 between separator 125 and solvent extraction device 140 open after the input masses (fluid and solvent) substantially balances with the mass in separator 125 and a sufficient period of time has elapsed to permit separation between the first and second layers. Depending on what solvent is used, and therefore which layer settles to the bottom of separator 125, either valve 115b between separator 125 and first waste container 135 is opened or valve 130 between separator 125 and solvent extraction device 140 is opened. One of ordinary skill in the art would appreciate that the timing of the opening is dependent upon how much fluid is in the first and second layers and would further appreciate that it is preferred to keep valve 115b between separator 125 and first waste container 135 open just long enough to remove all of the first layer and some of the second layer, thereby ensuring that as much solvent as possible has been removed from the fluid being sent to solvent extraction device 140.

In embodiments, an infusion grade fluid ("IGF") may be employed via one or more inputs 160 which are in fluid communication with the fluid path 121 leading from separator 125 to solvent extraction device 140 for priming. In an embodiment, saline is employed as the infusion grade priming fluid in at least one of inputs 160. In an embodiment, 0.9% sodium chloride (saline) is employed. In other embodiments, glucose may be employed as the infusion grade priming fluid in any one of inputs 160.

A plurality of valves 115c and 115d are also incorporated in the flow stream from glucose input 155 and saline input 160 respectively, to the tubing providing the flow path 121 from separator 125 to solvent extraction device 140. Infusion grade fluid such as saline and/or glucose is incorporated into embodiments of the present specification in order to prime solvent extraction device 140 prior to operation of the system. In embodiments, saline is used to prime most of the fluid communication lines and solvent extraction device 140. If priming is not required, the infusion grade fluid inputs are not employed. Where such priming is not required, the glucose and saline inputs are not required. In an embodiment, priming is not required in the lines between a second waste container 165 and output container 145. Also, one of ordinary skill in the art would appreciate that the glucose and saline inputs can be replaced with other primers if required by the solvent extraction device 140.

In some embodiments, solvent extraction device 140 is a charcoal column designed to remove the specific solvent used in solvent input 110. Exemplary solvent extraction device 140 includes but is not limited to an Asahi Hemosorber™ charcoal column or the Baxter/Gambro Adsorba™ 300C charcoal column or any other charcoal column that is employed in blood hemoglobin perfusion procedures. In embodiments, it should be noted that if the charcoal column is pre-primed with glucose, it will limit the amount of glucose removed from plasma because the free glucose in the priming agent will bind to glucose sites in the charcoal column, limiting its ability to absorb more glucose. A pump 150 is used to move the second layer from separator 125, through solvent extraction device 140, and to output container 145, through a U-shaped configuration. In embodiments, pump 150 is a rotary peristaltic pump, such as a Masterflex Model 77201-62.

The first layer is directed to waste container 135 that is in fluid communication with separator 125 through tubing and at least one valve 115b. Additionally, other waste, if generated, can be directed from the fluid path connecting solvent extraction device 140 and output container 145 to second waste container 165. Optionally, in an embodiment, a valve 115f is included in the path from the solvent extraction device 140 to the output container 145. Optionally, in an embodiment, a valve 115g is included in the path from the solvent extraction device 140 to the second waste container 165.

In an embodiment of the present specification, gravity is used, wherever practical, to move fluid through each of the plurality of components. For example, gravity is used to drain input plasma 105 and input solvent 110 into mixer 120. Where mixer 120 comprises a shaker bag and separator 125 comprises a funnel bag, fluid is moved from the shaker bag to the funnel bag and, subsequently, to first waste container 135, if appropriate, using gravity.

Suitable materials for use in any of the apparatus components, including bags and tubing, as described herein include materials that are biocompatible, approved for medical applications that involve contact with internal body fluids, and in compliance with U.S. PVI or ISO 10993 standards. Further, the materials do not substantially degrade from, for instance, exposure to the solvents used in the present invention, during at least a single use. The materials are sterilisable by radiation, steam or ethylene oxide (EtO) sterilization. Such suitable materials are capable of being formed into objects using conventional processes, such as, but not limited to, extrusion, injection molding and others. Materials meeting these requirements include, but are not limited to, nylon, polypropylene, polycarbonate, acrylic, polysulfone, polyvinylidene fluoride (PVDF), fluoroelastomers such as VITON, available from DuPont Dow Elastomers L.L.C., thermoplastic elastomers such as SANTOPRENE, available from Monsanto, polyurethane, polyvinyl chloride (PVC), polytetrafluoroethylene (PTFE), polyphenylene ether (PFE), perfluoroalkoxy copolymer (PFA), which is available as TEFLON PFA from E.I. du Pont de Nemours and Company, and combinations thereof.

Valves 115, 115a, 115b, 115c, 115d, 115e, 115f, 115g, 116 and any other valve used in each embodiment may be composed of, but are not limited to, pinch, globe, ball, gate or other conventional valves. In some embodiments, the valves are occlusion valves such as Acro Associates' Model 955 valve. However, the present specification is not limited to a valve having a particular style. Further, the components of each system described in accordance with embodiments of the present specification may be physically coupled together or coupled together using conduits that may be composed of flexible or rigid pipe, tubing or other such devices known to those of ordinary skill in the art.

In an additional embodiment, not shown in FIG. 1, the output fluid in output container 145 is subjected to a solvent detection system, or lipid removing agent detection system, to determine if any solvent, or other undesirable component, is in the output fluid. In embodiments, a solvent sensor is only employed in a continuous flow system. In one embodiment, the output fluid is subjected to sensors that are capable of determining the concentrations of solvents introduced in the solvent input, such as n-butanol or di-isopropyl ether. In embodiments, the sensors are capable of providing such concentration information on a real-time basis and without having to physically transport a sample of the output fluid, or air in the headspace, to a remote device. The resultant separated modified HDL particles are then introduced to the bloodstream of the patient.

In one embodiment, molecularly imprinted polymer technology is used to enable surface acoustic wave sensors. A surface acoustic wave sensor receives an input, through some interaction of its surface with the surrounding environment, and yields an electrical response, generated by the piezoelectric properties of the sensor substrate. To enable the interaction, molecularly imprinted polymer technology is used. Molecularly imprinted polymers are plastics programmed to recognize target molecules, like pharmaceuticals, toxins or environmental pollutants, in complex biological samples. The molecular imprinting technology is enabled by the polymerization of one or more functional monomers with an excess of a crosslinking monomer in presence of a target template molecule exhibiting a structure similar to the target molecule that is to be recognized, i.e. the target solvent.

The use of molecularly imprinted polymer technology to enable surface acoustic wave sensors can be made more specific to the concentrations of targeted solvents and are capable of differentiating such targeted solvents from other possible interferents. As a result, the presence of acceptable interferents that may have similar structures and/or properties to the targeted solvents would not prevent the sensor from accurately reporting existing respective solvent concentrations.

Alternatively, if the input solvent comprises certain solvents, such as n-butanol, electrochemical oxidation could be used to measure the solvent concentration. Electrochemical measurements have several advantages. They are simple, sensitive, fast, and have a wide dynamic range. The instrumentation is simple and not affected by humidity. In one embodiment, the target solvent, such as n-butanol, is oxidized on a platinum electrode using cyclic voltammetry. This technique is based on varying the applied potential at a working electrode in both the forward and reverse directions, at a predefined scan rate, while monitoring the current. One full cycle, a partial cycle, or a series of cycles can be performed. While platinum is the preferred electrode material, other electrodes, such as gold, silver, iridium, or graphite, could be used. Although, cyclic voltammetric techniques are used, other pulse techniques such as differential pulse voltammetry or square wave voltammetry may increase the speed and sensitivity of measurements.

Embodiments of the present specification expressly cover any and all forms of automatically sampling and measuring, detecting, and analyzing an output fluid, or the headspace above the output fluid. For example, such automated detection can be achieved by integrating a mini-gas chromatography (GC) measuring device that automatically samples air in the output container, transmits it to a GC device optimized for the specific solvents used in the delipidation process, and, using known GC techniques, analyzes the sample for the presence of the solvents.

Figure 2:
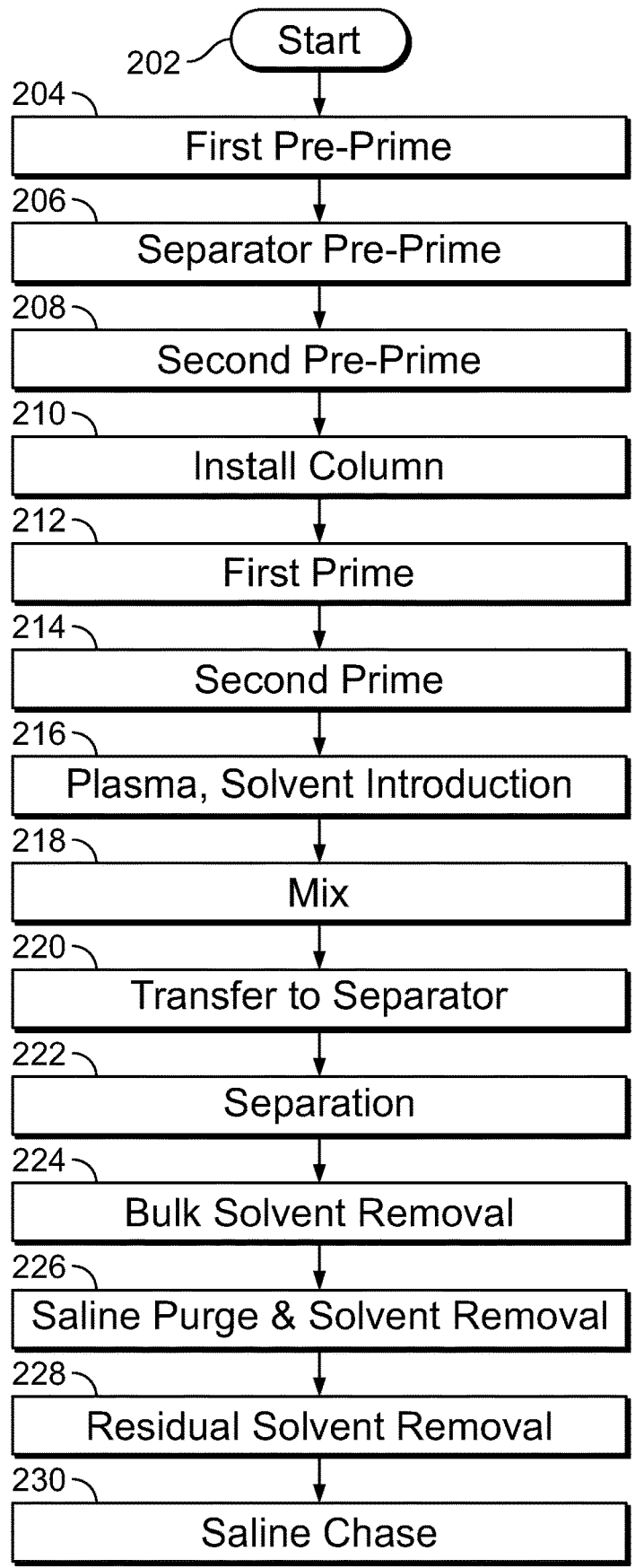
FIG. 2 is a flow chart illustrating an exemplary process for treating cardiovascular diseases using the system of FIG. 1, in accordance with some embodiments of the present specification.

The method of operation of system components 100 of FIG. 1 will now be described in detail below. FIG. 2 is a flow chart illustrating an exemplary process for separating modified HDL, in accordance with some embodiments of the present specification. The method described in context of FIG. 2 may be implemented using system components 100 described in context of FIG. 1. At 202, a plasma delipidation process is started once the bags and tubing sets are connected in place, as described in FIG. 1. At 204, a first priming fluid pre-primes various fluid lines. In embodiments, fluid lines include the tubing sets and any other channels for transporting the fluids between the system's components.

In some embodiments, the present specification includes a computing device with an input/output controller, at least one communications interface and system memory. The system memory includes at least one random access memory (RAM) and at least one read-only memory (ROM). These elements are in communication with a central processing unit (CPU) to enable operation of the computing device. In various embodiments, the computing device may be a conventional standalone computer or alternatively, the functions of the computing device may be distributed across multiple computer systems and architectures. In some embodiments, execution of sequences of programmatic instructions enables or causes the processor to perform various functions and processes. In alternate embodiments, hard-wired circuitry may be used in place of, or in combination with, software instructions for implementation of the processes of systems and methods described in this specification. Thus, the systems and methods described are not limited to any specific combination of hardware and software.

In some configurations, the embodiments described in the present specification include a controller having at least a processor or processing circuitry and a system memory that is in data communication with at least one of the basic components of the system of the present specification to control or automate operation of the system, including, but not limited to:

One or more fluid inputs;

One or more mixing devices that may be used to mix fluid from a fluid input and solvent from a solvent input;

One or more valves that may be used to control the flow of a fluid, a solvent or a fluid-solvent mixture;

One or more valves that may be used to control the flow of fluid from a fluid input and to control the flow of solvent from a solvent input;

One or more valves that may be used to control the flow of a fluid-solvent mixture through tubing and to a separator;

One or more separators for performing bulk solvent separation and valves associated therewith;

One or more pressure sensors and/or valves positioned in the flow stream to control the flow of the second layer to the solvent extraction device;

One or more glucose inputs and valves associated therewith;

One or more saline inputs and valves associated therewith;

One or more solvent extraction devices; and/or

One or more pumps, which may be a peristaltic, roller, or rotary pump.

Figure 3A:
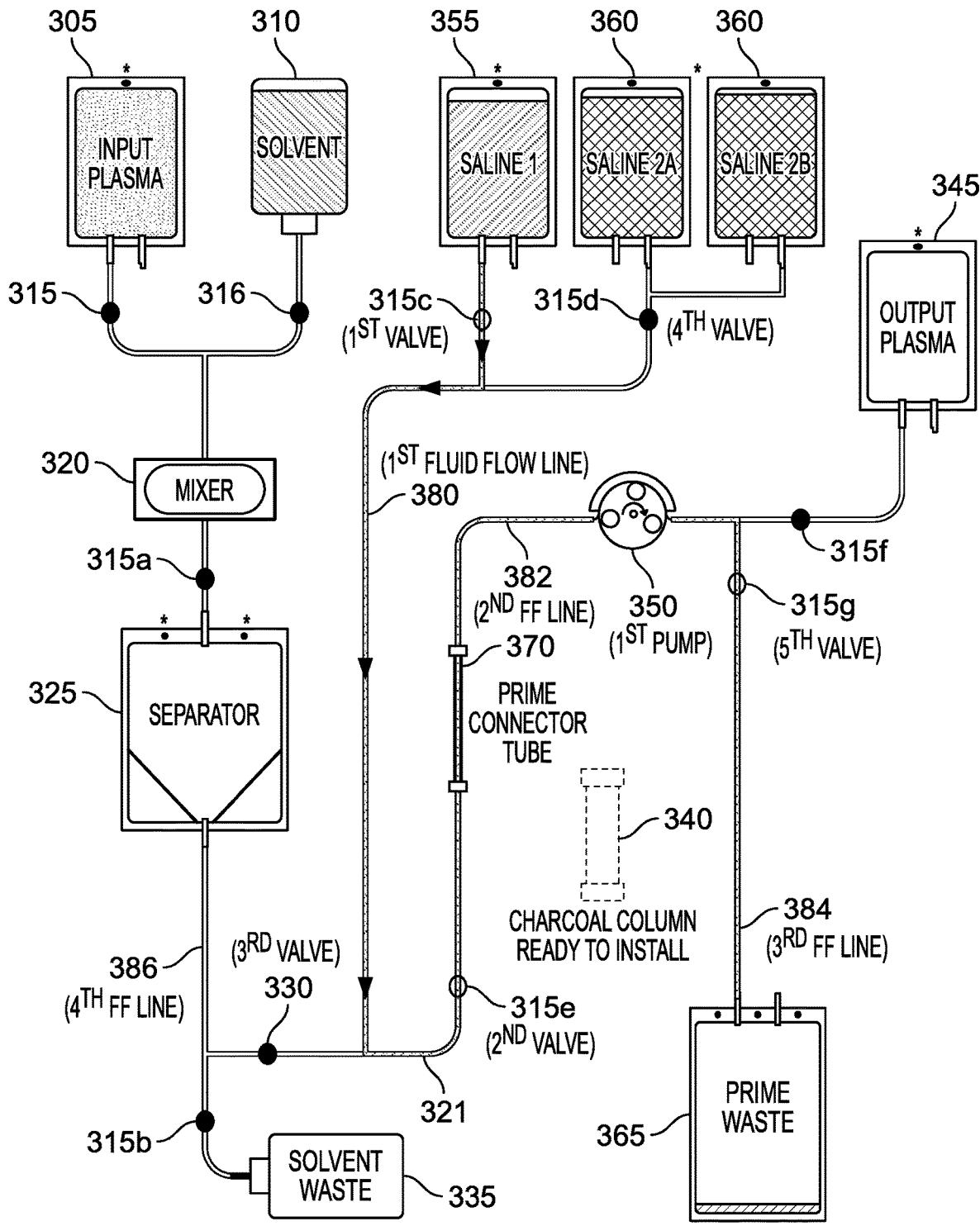
FIG. 3A is a schematic representation of the system illustrating the implementation of the process described in FIG. 2, in accordance with some embodiments of the present specification.

FIG. 3A illustrates a bag 355 containing the priming fluid. In some embodiments, the priming fluid for the first priming is saline. Saline prepares the system by flushing the fluid flow-path (lines) between bag 355 and a second waste container 365. The fluid flow path flushed at this step includes a Fluid Flow Path 1 (FFP1) comprising line 380 between bag 355 and a line 321 where line 321 is the fluid flow path between the separator and a prime connector tube 370, a line 382 between prime connector tube 370 and the pump 350, and a line 384 extending between the pump and second waste container 365. FFP1 is not is communication with inputs 305, 310, 360, mixer 320, first waste container 335, and output container 345. In embodiments, the pump 350 functions to draw the priming fluid towards the prime waste or second waste container 365. In embodiments, second waste container 365 is configured to collect the prime waste.

In embodiments, at the preliminary priming stage, a solvent extraction device is separate from the system. The solvent extraction device may be a charcoal column that is subsequently added to the system and used to extract a solvent from plasma that contains modified HDL particles. The solvent extraction device is substituted with prime connector tube 370 between the fluid lines 321 and 382, between bag 355 and second waste container 365. Pre-priming the fluid lines ensures that air is substantially removed from the fluid lines. Later when the solvent extraction device is connected, the absence of air safeguards the function of the solvent extraction device. In embodiments, the solvent extraction device is a charcoal column comprising coated beads of charcoal. The substantial or material presence of air interferes with the efficiency and surface area of the charcoal column. In embodiments, once the pump is closed, it does not allow for backflow of fluids. At this stage, valves 315c, 315e, and 315g, along FFP1 are open to facilitate passage and direct the flow of priming fluid from bag 355 to second waste container 365 containing the prime waste. Other valves (315, 316, 315a, 315b, 315d, 315f, and 330) remain closed to prevent passage of the saline to other parts of the lines, and therefore FFP1 is not in fluid communication with inputs 305, 310, 360, mixer 320, first waste container 335, and output container 345.

Figure 3B:
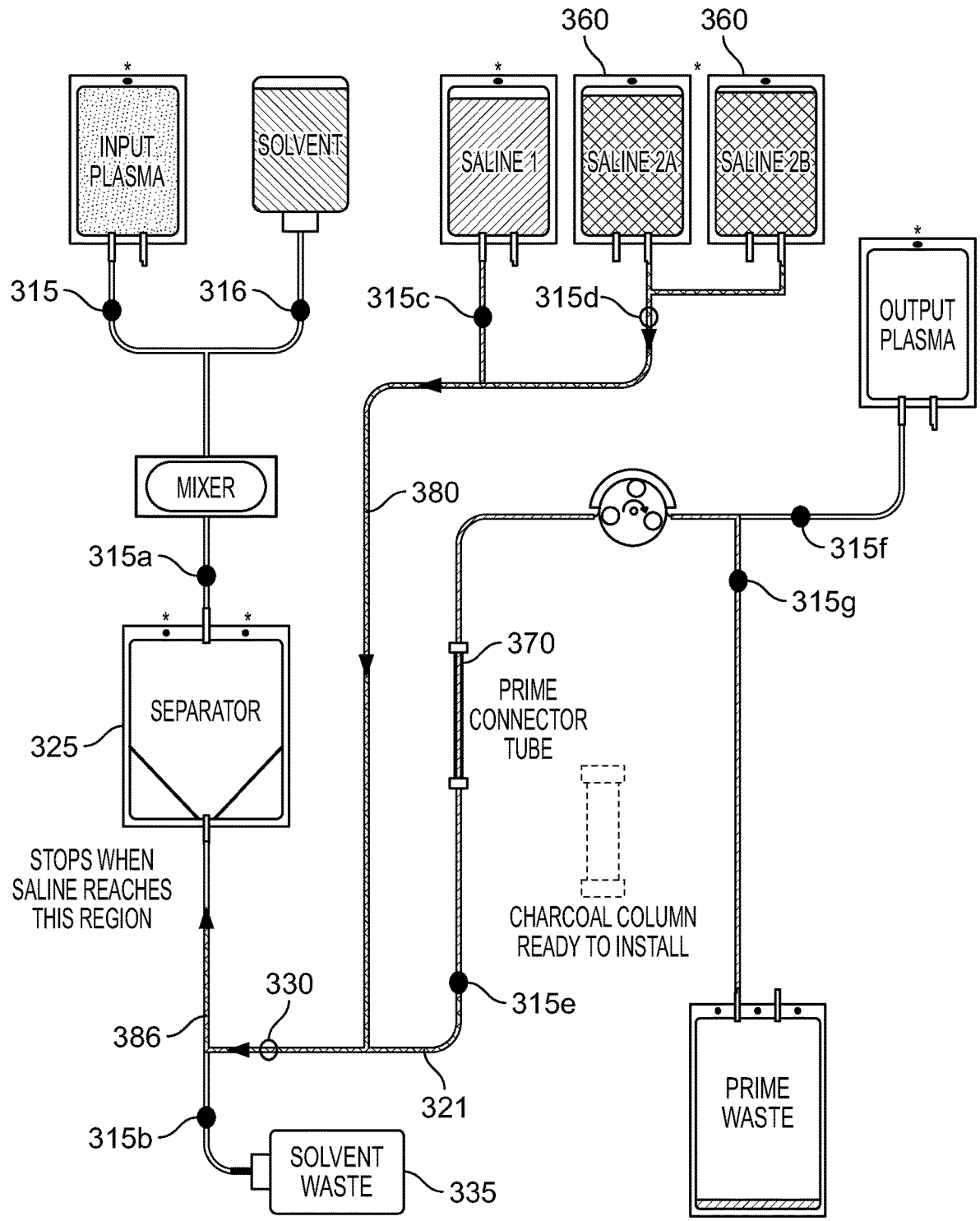
FIG. 3B is a schematic representation of the system illustrating the implementation of the process described in FIG. 2, in accordance with some embodiments of the present specification.

Following step 204, valves 315d and 330 are opened to facilitate passage of priming fluid from bags 360 to separator 325, while the other valves (315, 316, 315a, 315b, 315c, 315e, 315f, and 315g) remain closed. At 206, a priming fluid pre-primes various fluid lines towards a separator 325. FIG. 3B illustrates at least two bags 360 containing the priming fluid. In embodiments, the priming fluid for priming the lines to separator 325 is saline. The saline prepares the system by flushing the lines between bags 360 and separator 325. The fluid flow paths flushed at this step may include line 380 between bags 360 and line 321, and line 386 extending from separator 325 to line 321. Therefore, a second fluid flow path (FFP2) may be defined as the path including line 380 between bags 360 and line 321, and line 386 extending from separator 325 to line 321. FFP2 does not include fluid paths to inputs 305, 310, and 355, mixer 320, prime connector tube 370, pump 350, first waste container 335, second waste container 365, and output container 345. The solvent extraction device is still separate from the system.

Figure 3C:
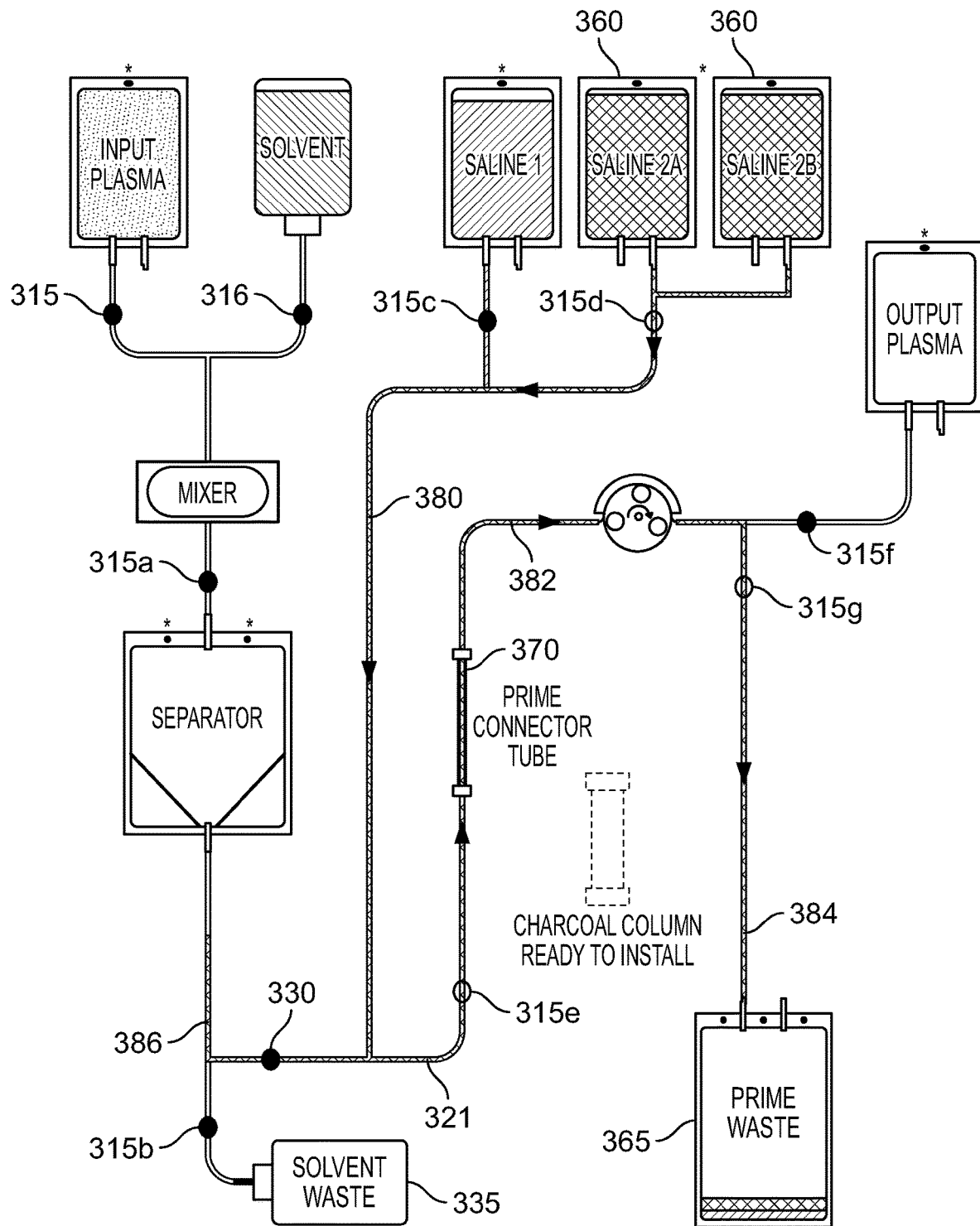
FIG. 3C is a schematic representation of the system illustrating the implementation of the process described in FIG. 2, in accordance with some embodiments of the present specification.

Following step 206, valve 315d remains open, valves 315e and 315g are additionally opened, while all other valves (315, 316, 315a, 315b, 315c, 315f, and 330) remain in order to facilitate fluid flow along a third fluid flow path (FFP3). FFP3 may be defined as the path of fluid from bags 360, through prime connector tube 370, to second waste container 365. FFP3 is not in fluid communication with inputs 305, 310, and 355, mixer 320 separator 325, first waste container 335, and output container 345. At 208, a second pre-priming operation is performed in the various fluid lines of the system through FFP3. Referring to FIG. 3C, at this stage, priming fluid from bags 360 are transported through valves 315d and 315e, through prime connector tube 370, and through valve 315g, toward second waste container 365, while all other valves remain closed. Step 208 is concluded with presence of priming fluids in the main lines of the system, which include line 380, line 321, line 386, line 382, and line 384.

Figure 3D:
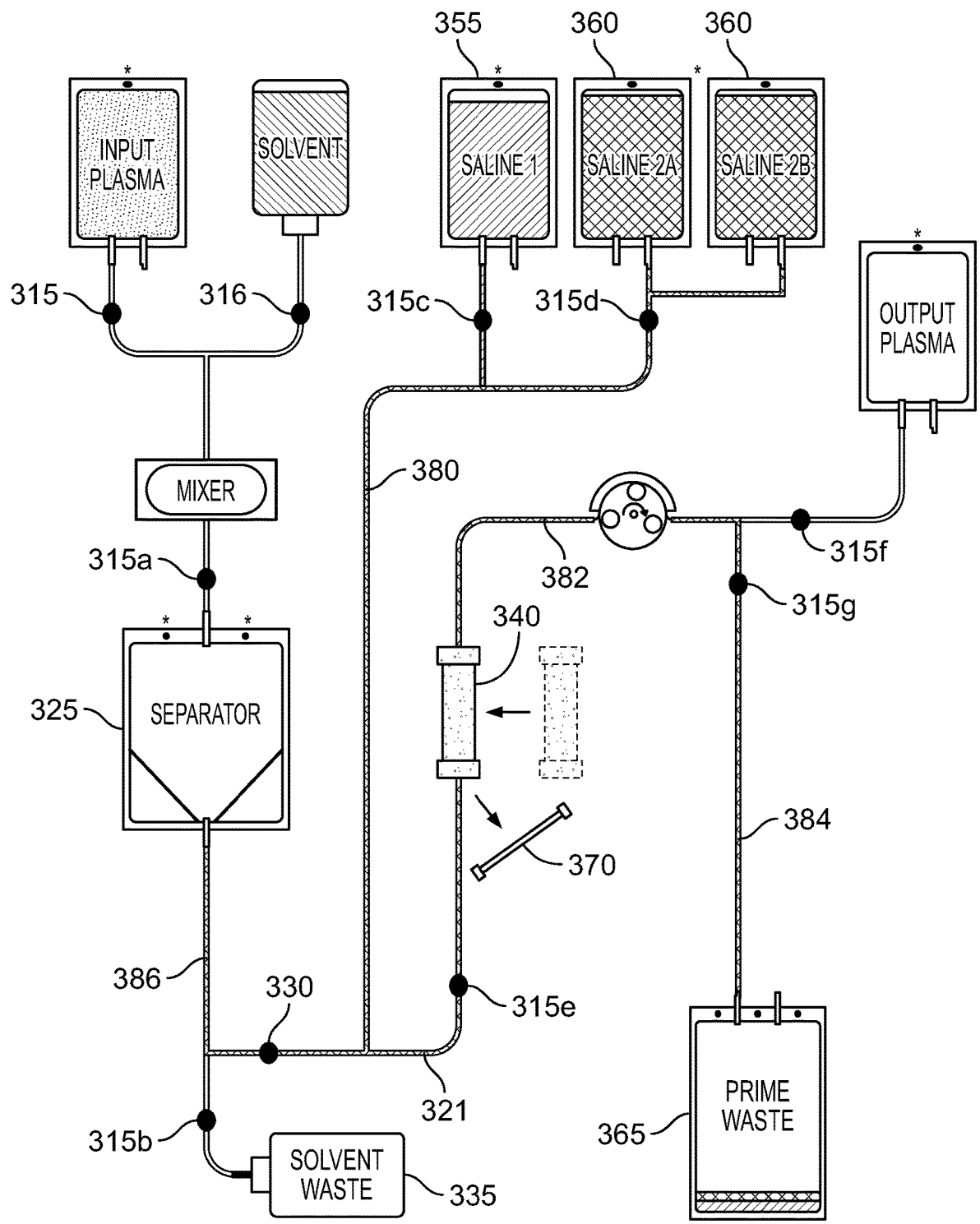
FIG. 3D is a schematic representation of the system illustrating the implementation of the process described in FIG. 2, in accordance with some embodiments of the present specification.

Following step 208, the priming fluid transported through the fluid lines is drained into second waste container 365, which is configured to collect prime waste. All the valves (315, 316, 315a, 315b, 315c, 315d, 315f, 315e, 315g, 330) are then closed. Therefore there is no path for flow of fluids. The prime connector tube 370 is clamped and removed from the fluid line. At 210, a solvent extraction device is installed into the system by replacing the prime connector tube 370. Referring to FIG. 3D, a solvent extraction device 340 is installed at the location within the fluid line, between lines 321 and 382, where prime connector tube 370 was originally placed. Fluid lines (lines 321, 380, 382, 384, and 386) between bags 355 and 360, separator 325, and second waste container 365 are pre-primed, that is, they are primed before installing solvent extraction device 340.

Figure 3E:
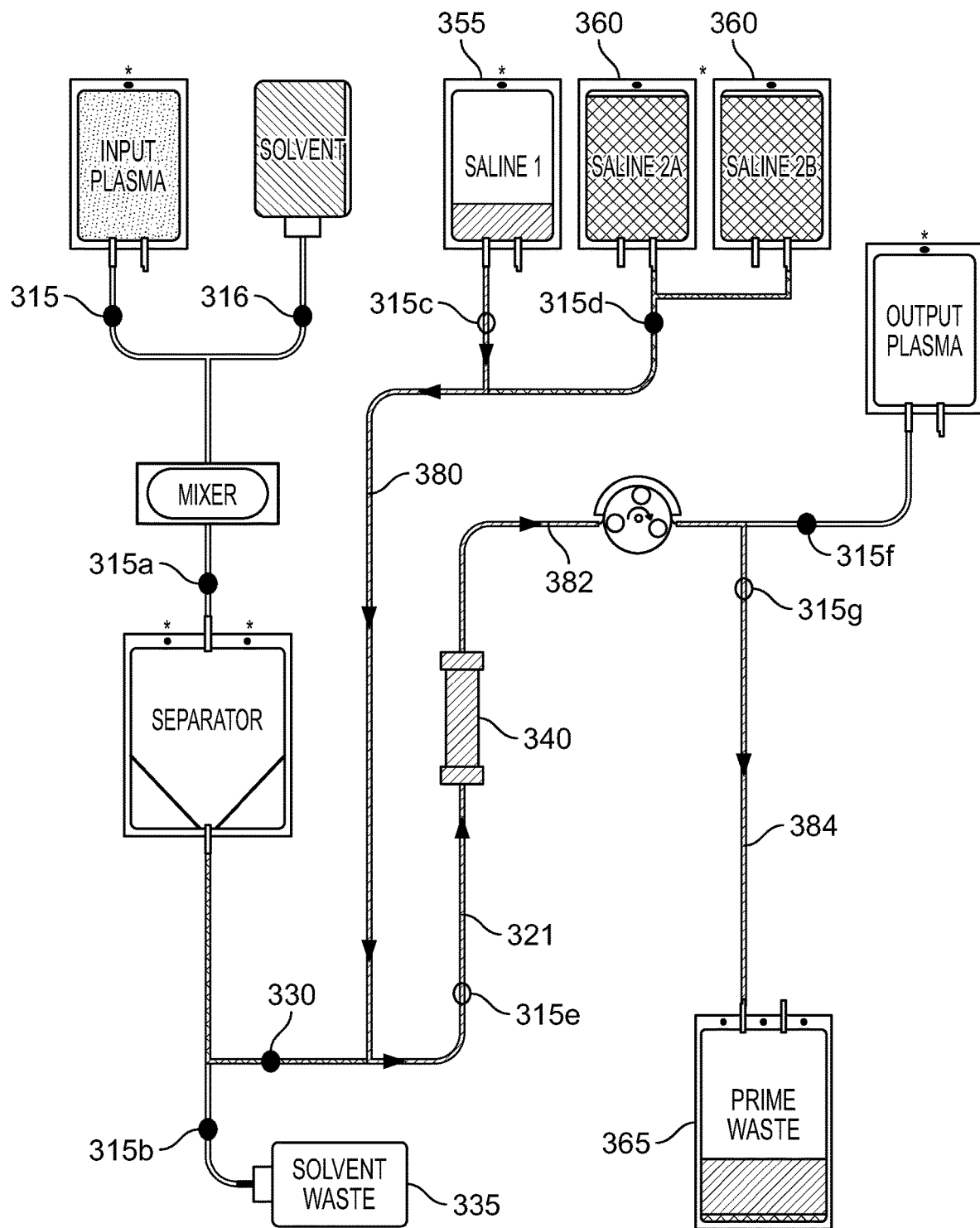
FIG. 3E is a schematic representation of the system illustrating the implementation of the process described in FIG. 2, in accordance with some embodiments of the present specification.

Following step 210, valves 315c, 315e, and 315g are opened while all other valves (315, 316, 315a, 315b, 330, 315d, 315f) remain closed, which defines a fourth fluid flow path (FFP4) extending from input 355, through solvent extraction device 340, to second waste container 365. FFP4 is not in fluid communication with inputs 305, 310, 360, mixer 320, separator 325, first waste container 335, and output container 345. At 212, a first priming is performed of the various fluid lines. Referring to FIG. 3E, priming fluid from bag 355 is depleted and transported through FFP4 comprising valves 315c and 315e, through solvent extraction device 340, valve 315g, and into second waste container 365. The fluid flow paths that are primed at this step include lines 380, 321, 382, and 384.

Figure 3F:
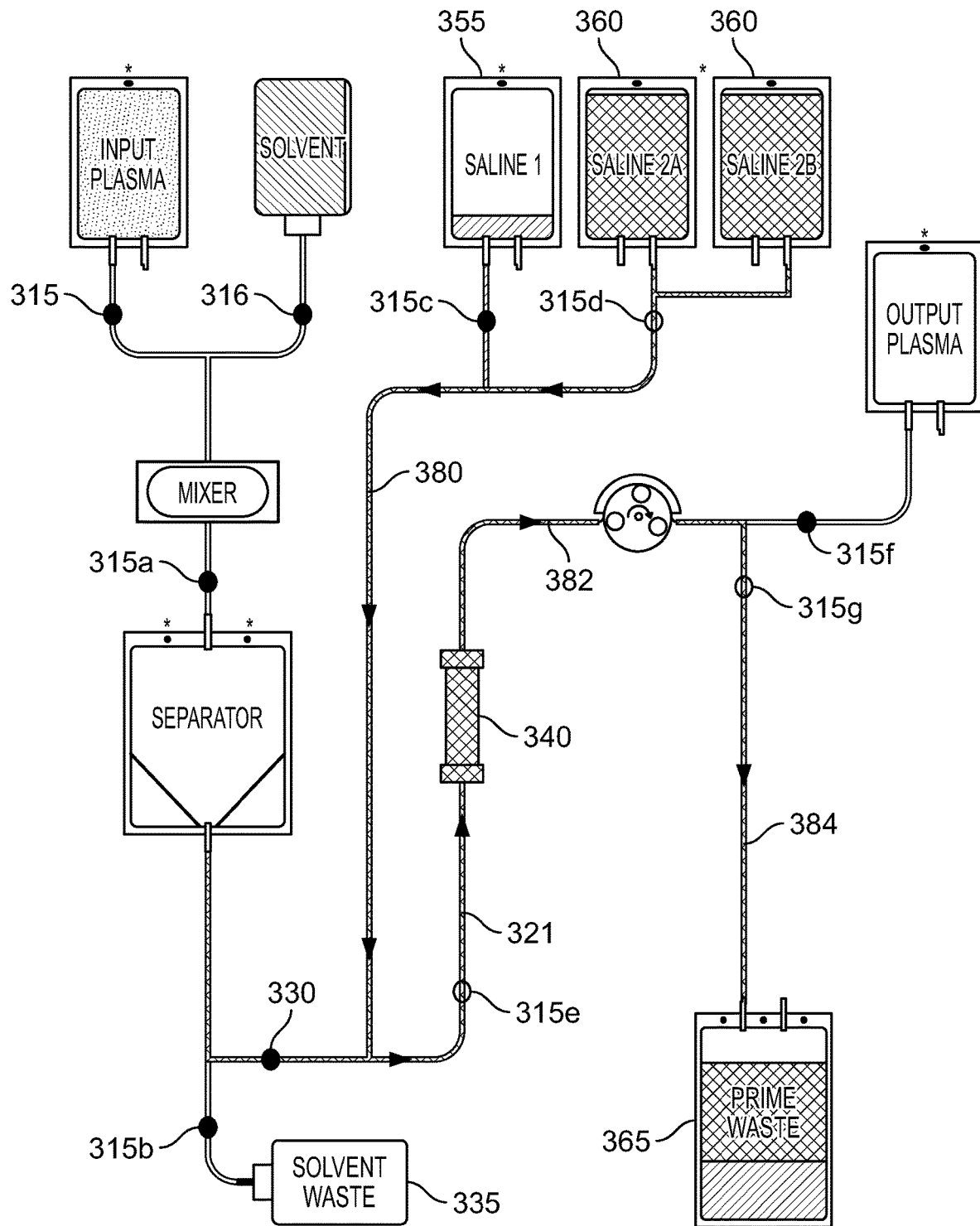
FIG. 3F is a schematic representation of the system illustrating the implementation of the process described in FIG. 2, in accordance with some embodiments of the present specification.

Following step 212, valve 315d is opened, valves 315e and 315g remain open, while all other valves (315, 316, 315a, 315b, 315c, 330, 315f) remain closed, which defines a fifth fluid flow path (FFP5) extending from inputs 360, through solvent extraction device 340, to second waste container 365. FFP5 is not in fluid communication with inputs 305, 310, 355, mixer 320, separator 325, first waste container 335, and output container 345. At 214, a second priming is performed of the various fluid lines through FFP5. Referring to FIG. 3F, priming fluid from bags 360 is transported through valves 315d, 315e, through solvent extraction device 340, valve 315g, and into second waste container 365. The fluid flow paths that are primed at this step include lines 321, 380, 382, and 384.

At the conclusion of steps 212 and 214, all main fluid lines including lines 321, 380, 382, and 384, separator 325 and solvent extraction device 340 are primed. In embodiments, fluid lines extending from bottom of separator 325 to second waste container 365, configured to contain prime waste, is filled with priming fluid. Priming also results in removal of small particulates from solvent extraction device 340.

Following step 214, valve 315 is opened and all other valves (316, 315a, 315b, 315c, 315d, 315e, 315f, 315g, and 330) are closed, defining a sixth fluid flow path (FFP6) from input 305 to mixer 320. FFP6 is not in fluid communication with bag, 310, separator 325, first waste container 335, inputs 310, 355, 360, solvent extraction device 340, pump 350, second waste container 365, and output container 345. At 216, the plasma fluid and the solvent are introduced one after the other, into a mixing device of the system. In embodiments, a blood fraction of the patient is obtained, which in a still further embodiment is plasma. The process of blood fractionation is typically achieved by filtration, centrifuging the blood, aspiration, or any other method known to persons skilled in the art. Blood fractionation separates the plasma from the blood. In an embodiment, blood fractionation is performed remotely. In one embodiment, blood is withdrawn from a patient in a volume sufficient to produce about 12 ml/kg of plasma based on body weight. During the fractionation process, the blood can optionally be combined with an anticoagulant, such as sodium citrate, and centrifuged at forces approximately equal to 2,000 times gravity. The blood is separated into plasma and red blood cells using methods commonly known to one of skill in the art, such as plasmapheresis. In an embodiment, the red blood cells are then aspirated from the plasma. In one embodiment, the process of blood fractionation is performed by withdrawing blood from the patient with the cardiovascular and/or related disease, and who is being treated by the physician. In an alternative embodiment, the process of blood fractionation is performed by withdrawing blood from a person other than the patient with the cardiovascular and/or related disease who is treated by the physician. Therefore, the plasma obtained as a result of the blood fractionation process may be either autologous or non-autologous.

Subsequent to fractionation, the red blood cells are either stored in an appropriate storage solution or, preferably, returned to the patient during plasmapheresis. Physiological saline, 5% albumin, or other suitable fluid may also optionally be administered to the patient to replenish volume. If the blood was obtained from an individual other than the patient, the cells are returned to that individual, who can also be referred to as the donor.

Plasma obtained from blood is usually a straw-colored liquid that comprises the extracellular matrix of blood cells. Plasma is typically 95% water, and contains dissolved proteins, which constitute about 6-8% of plasma. The plasma also contains glucose, clotting factors, electrolytes, hormones, carbon dioxide, and oxygen. The plasma has a density of approximately 1006 kg/m3, or 1.006 g/ml.

In some alternate embodiments, Low Density Lipoprotein (LDL) is also separated from the plasma. Separated LDL is usually discarded. In alternative embodiments, LDL is retained in the plasma. In accordance with embodiments of the present specification, blood fraction or plasma obtained includes plasma with High Density Lipoprotein (HDL), and may or may not include other protein particles. In embodiments, autologous or non-autologous plasma collected from the patient or donor, respectively, is subsequently treated via an approved plasmapheresis device. The plasma may be transported using a continuous or batch process.

Figure 3G:
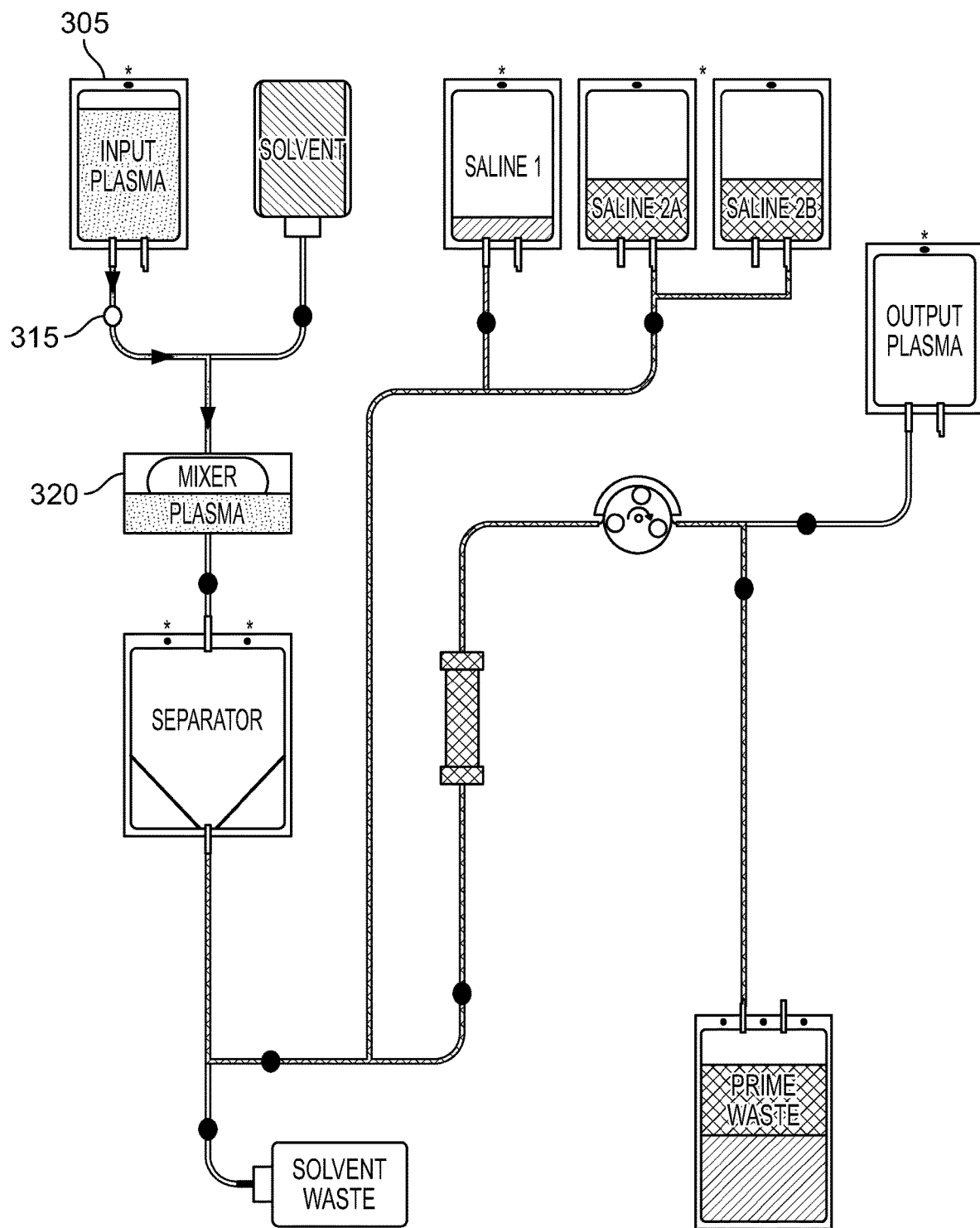
FIG. 3G is a schematic representation of the system illustrating the implementation of the process described in FIG. 2, in accordance with some embodiments of the present specification.

Referring to FIG. 3G, a plasma input bag 305 contains the plasma that will be treated by the various embodiments of the present specification. The plasma is transported from bag 305, along FFP6, through a valve 315, into a mixing device 320.

Figure 3H:
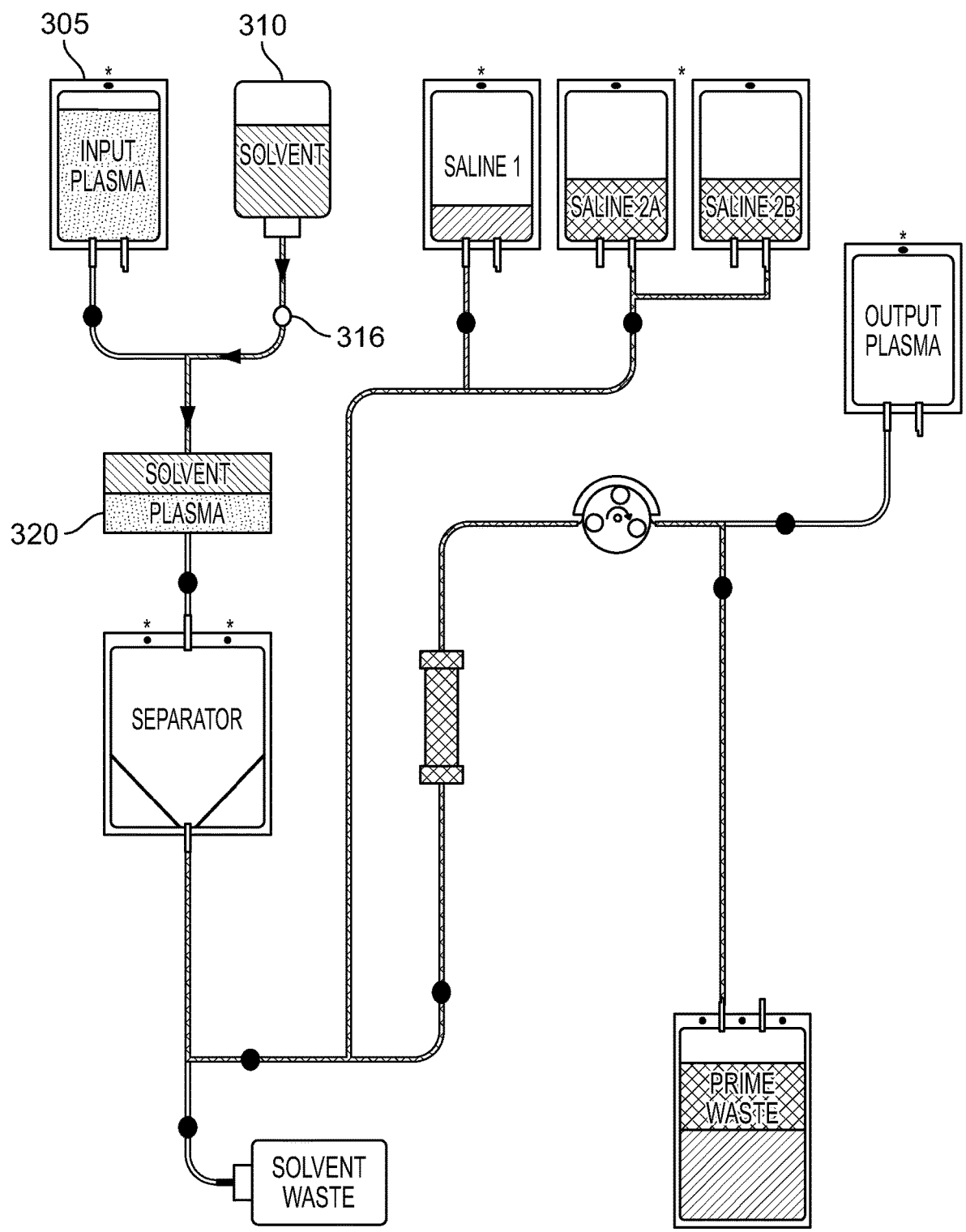
FIG. 3H is a schematic representation of the system illustrating the implementation of the process described in FIG. 2, in accordance with some embodiments of the present specification.

Following transportation of plasma from bag 305 to mixing device 320, valve 315 is closed and valve 316 is opened, while all the other valves (315a, 315b, 315c, 315d, 315e, 315f, 315g, 330) remain closed, thus defining a seventh fluid flow path (FFP7) from bag 310 to mixing device 320. FFP7 is not in fluid communication with bag 305, separator 325, first waste container 335, inputs 310, 355, 360, solvent extraction device 340, pump 350, second waste container 365, and output container 345. Referring to FIG. 3H, a solvent input bag 310 contains the solvent. The solvent is transported along FFP7, from bag 310, through a valve 316, into mixing device 320. The solvent is used for extracting lipids from the plasma fluid or from particles within the plasma fluid. Suitable extraction solvents include solvents that extract or dissolve lipid, including but not limited to phenols, hydrocarbons, amines, ethers, esters, alcohols, halohydrocarbons, halocarbons, and combinations thereof. Examples of suitable extraction solvents are ethers, esters, alcohols, halohydrocarbons, or halocarbons which include, but are not limited to di-isopropyl ether (DIPE), which is also referred to as isopropyl ether, diethyl ether (DEE), which is also referred to as ethyl ether, lower order alcohols such as butanol, especially n-butanol, ethyl acetate, dichloromethane, chloroform, isoflurane, sevoflurane (1,1,1,3, 3,3-hexafluoro-2-(fluoromethoxy) propane-d3), perfluorocyclohexanes, trifluoroethane, cyclofluorohexanol, and combinations thereof. In an embodiment, a mix of Sevoflurane and n-butanol is used as the solvent. In an embodiment a volume ratio of Sevoflurane and n-butanol used is 95:5. In various embodiments, the plasma and the solvent are transported in any order. While transporting the plasma and the solvent to mixing device 320, the valves corresponding to bags containing the plasma (valve 315) and the solvent (valve 316) are respectively open. All other valves (315a, 315b, 315c, 315d, 315e, 315f, 315g, and 330) remain closed.

Following step 216, once the plasma and the solvent are in mixing device 320, all the valves (316, 316, 315a, 315b, 315c, 315d, 315e, 315f, 315g, 330) are closed. At 218, the plasma and the solvent, which are present together within the mixing apparatus are processed by a mixing operation. In an embodiment, the solvents used include either or both of organic solvents sevoflurane and n-butanol. In embodiments, the solvent is optimally designed such that only the HDL particles are treated to reduce their lipid levels and LDL levels are not affected.

The mixing process includes factoring in variables such as the solvent employed, mixing method, time, and temperature. Choice of a mixing method may also affect some system requirements, such as but not limited to functional requirements, packaging requirements, cost, and environmental requirements. Additional variables that may be considered in system design are as follows:

1. Priming. Whether the system can handle priming so that it can be primed and ready for a process.
2. Continuous or Interrupted Flow. Whether the system has to be continuous in nature (continuously separates plasma and inputs replacement fluid in parallel) or can handle discrete amounts of liquid (batch flow).
3. Closed Loop Control. Whether the system has to be monitored or can be validated by process.
4. Variable Flow. Whether the system can handle various ranges of flow.
5. Hold-up Volume. This is the amount of fluid or blood that remains in the circuit after the process is complete, as it is desirable to have as little blood or fluid outside of the patient at any given time and so that the plasma that will be returned to the patient is not overdiluted.
6. Mixing Control. Whether the system allows for controlling the level, speed or extent of mixing.
7. Plasma Range. Whether the system can handle different types of plasma, including normal plasma, high LDL plasma, high triglyceride plasma, and other types of plasma.
8. Packaging Requirements. Whether a hospital or blood bank could accommodate the footprint of the system and its associated components, including disposables and hardware.
9. Environmental Requirements. Whether the system could be deployed in a variety of settings with respect to operating noise/vibration and hardware durability (for example, whether it can be deployed in bloodbanks or hospitals).
10. Cost. Whether the system can be manufactured in a cost-effective manner (for example, no high cost, high precision connectors).

Different mixing methods provided different results in terms of remaining cholesterol, remaining phospholipids, remaining Apo-B, and remaining Apo-A, within the delipidated plasma obtained after the mixing. The mixing methods employed in the present specification take into account a plurality of variables that, when combined, achieve an ideal mixing environment for optimal selective delipidation. By way of background, several mixing methods, as are well-known to those of ordinary skill in the art were initially employed with little to no success. These methods included continuous vortex mixing, mixing using a static mixer, mixing using a silly straw mixer, and mixing using a rotating cylinder.

Continuous vortex type of mixing involves using a vortexer to mix smaller quantities of liquid. When a test tube or other container is pressed into the rubber cup of the vortexer, the motion is transferred to the liquid inside, creating a fluid vortex or whirlpool in an off-center rotation. Because the speeds achieved are close to 2500 rpm, the end result could be "overdelipidation", or complete delipidation of both HDL and LDL. As discussed above, it is not desirable to delipidate LDL.

A static mixer is a plate-type mixer or a mixer comprising mixing elements contained within an elongated housing that effectuates movement of a tube containing a mixture or mixture of fluids, where the movement is typically sideways from one side to another. It is typically employed for continuous mixing. This method of mixing does not work as it 1) involves direct connection to the patient for serial apheresis and delipidation and also results in "overdelipidation", or complete delipidation of both HDL and LDL. As discussed above, it is not desirable to delipidate LDL The "silly straw" method of mixing was designed as a coiled tube (a tubing set wrapped around a stick) through which a fluid mixture flows continuously creating a Taylor vortex. A continuous flow of plasma and solvent in a 2:1 solvent to plasma ratio was used. This method proved to be entirely ineffective. One theory is that in order to effectively selectively delipidate, the plasma and solvent mixture needs to be in full contact at a specified ratio, for a specified amount of time and that an instantaneous flow-through process could not achieve this equilibrium.

Mixing using a rotating cylinder involves a tube containing the mixture that rotates around its axis (similar to the movement of a record on a turntable) to mix the fluids within the tube. In using this process, the fluid tumbles from the top to the bottom of the test tube. While the method was not optimal for selective delipidation as described in the present specification, a novel mixing bag of specific geometry and size was designed and implemented.

The system of the present specification, and in particular, the mixing sub-system is designed so that it can be primed and ready for a process. In addition, the system of the current specification can handle fluid processing in batches without the need for continuous flow. The system of the present specification advantageously does not require closed loop control. Once the parameters (flow rate, volume) are established, the system is gravity based and operates accordingly. Optionally, a charcoal column is employed to further ensure that all solvent is removed. The system of the present specification can also accommodate various ranges of fluid flow. Because the system of the present specification is a stand-alone system (meaning that apheresis is not integrated), the issue of hold-up volume becomes a non-issue. The system of the present specification also allows for controlling the level of mixing by determining the speed of the mixer and using a mixing bag with an appropriate volume and geometry. Further, the system of the present specification is designed to be able to handle a wide and infinite range of plasma that can be treated by the system, including, but not limited to normal plasma, high LDL plasma, high triglyceride plasma, and other types of plasma. The system of the present specification has low to minimal footprint, is readily and easily deployable in a variety of environments with minimal noise impact. In addition, the system of the present specification can be manufactured in a cost-effective manner.

Figure 3I:
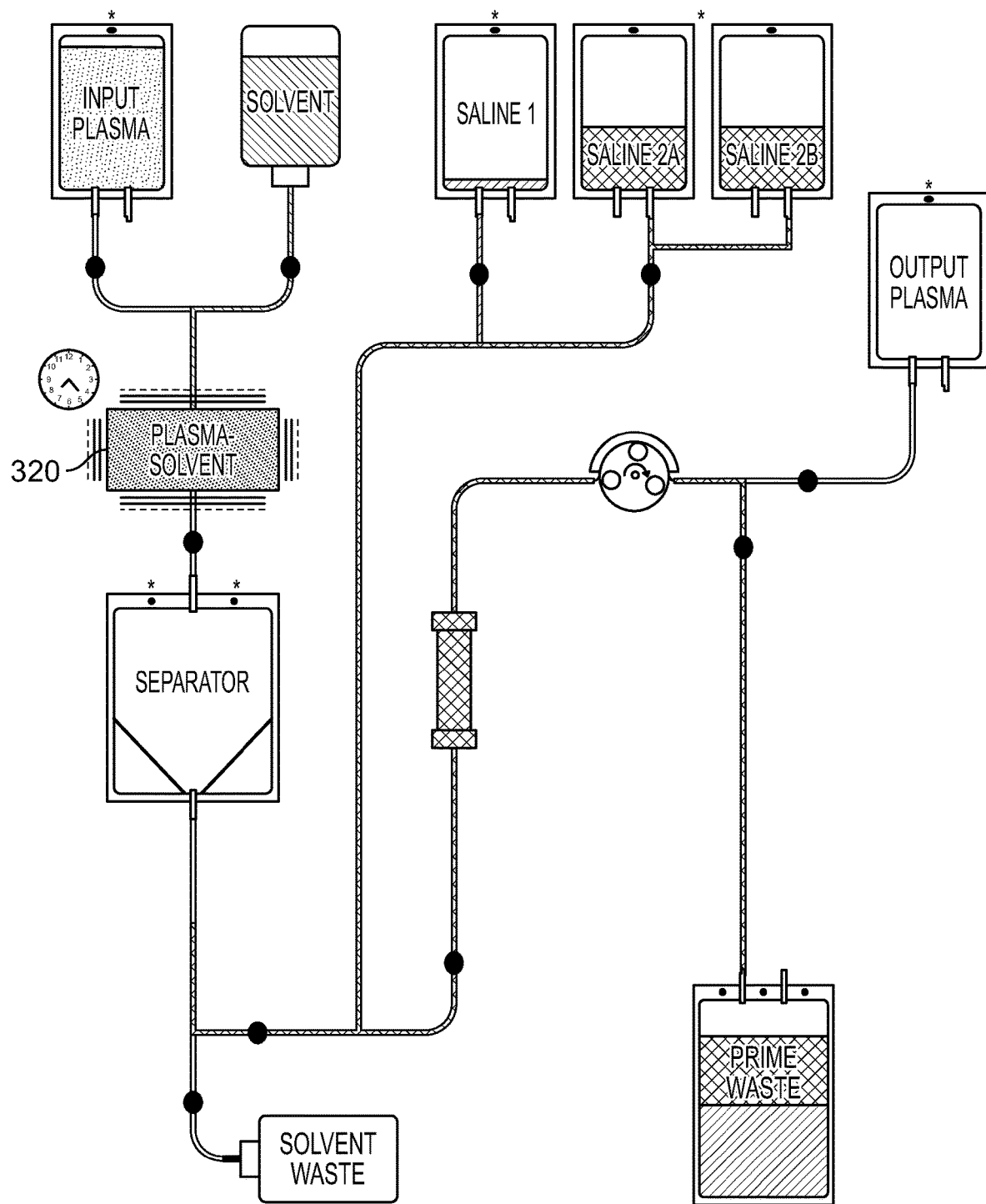
FIG. 3I is a schematic representation of the system illustrating the implementation of the process described in FIG. 2, in accordance with some embodiments of the present specification.

Referring to FIG. 3I, mixing device 320 may be a bag used for mixing the plasma and the solvent. In embodiments, mixing device 320 includes both an orbital mixer and a mixing bag, and is placed at an angle within the system. In one embodiment, the mixing bag is placed horizontally over the orbital mixing device, because this position may receive the most optimal orbital mixing action for the fluid contained in the bag, as most of the fluid would gravitate towards the bottom. The bag and its corners can be used to impart energy. The mixing bag, using an angled platform as described below may be placed at a slight angle to enable draining of the fluids. The angle may range from 0 degrees (completely vertical) to 90 degrees (completely horizontal). In one embodiment, the platform upon which the mixing bag rests is placed at an angle of 18.2 degrees. In one embodiment, mixing device 320 is of a circular shape. In another embodiment, mixing device 320 is of a rectangular shape.

Figure 7:
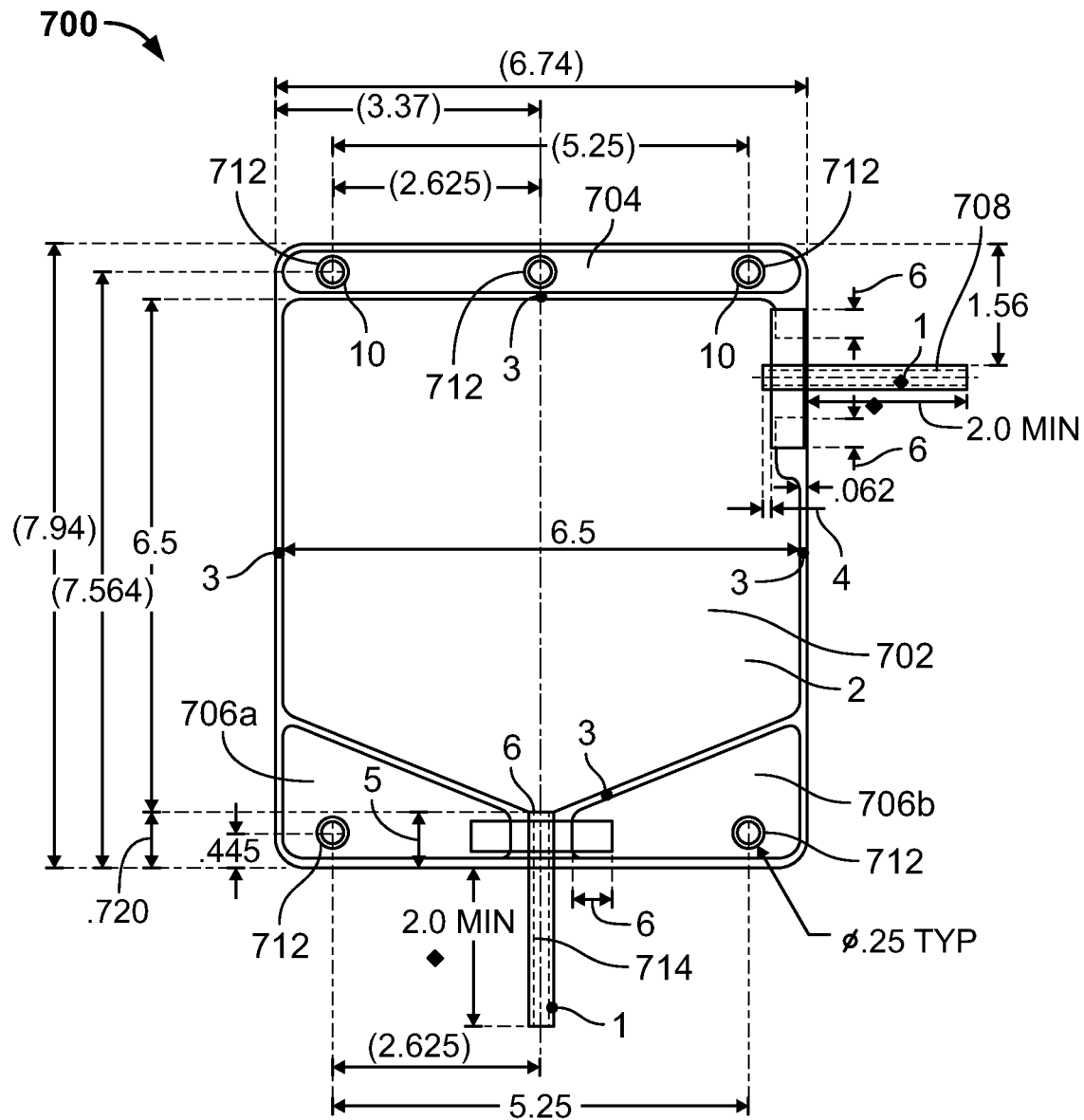
FIG. 7 illustrates an exemplary mixing device, in accordance with embodiments described in context of FIG. 3I.

FIG. 7 illustrates an exemplary mixing device (bag) 700, in accordance with embodiments described in context of FIG. 3I. Bag 700 is of a rectangular shape, comprising a section 702 where plasma and solvent fluid may be received through an input pipe 708. Section 702 has at least five edges and is at the center of bag 700. Section 702 is surrounded by sealed sections of bag 700. One of the edges of bag 700 includes a rectangular sealed section 704. Two mutually inclined edges, opposite to the edge along section 702, include triangular sealed sections 706a and 706b. Each sealed section 704, 706a, and 706b, includes at least one hanger hole, such as holes 712. Section 702 includes an output pipe 714 positioned between triangular sealed section 706a and 706b, to enable letting out of the mixture.

Figure 8A:
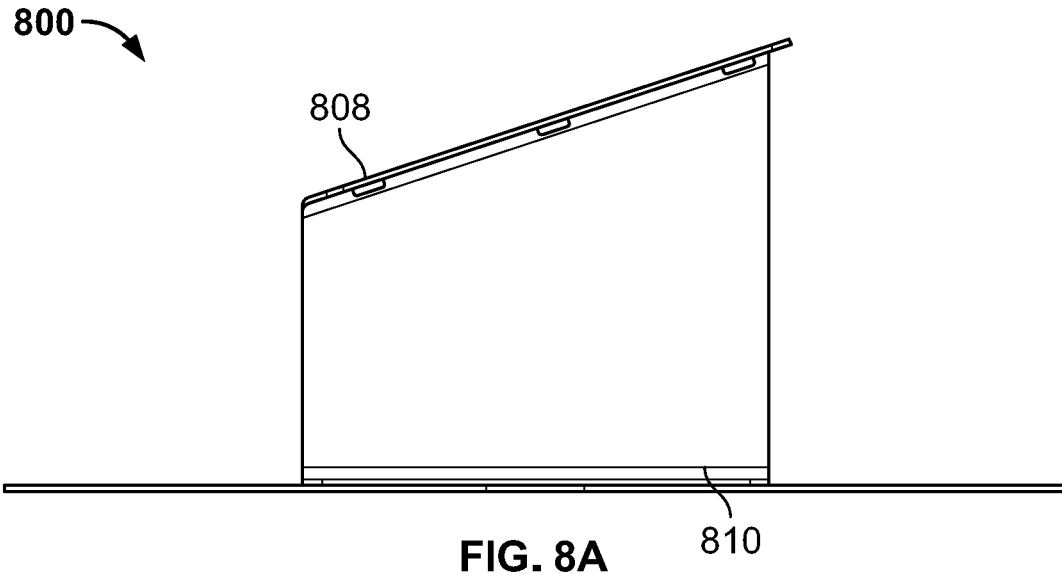
FIG. 8A illustrates a side view of shaker angle brackets that are used to a position mixing device within a system, in accordance with some embodiments of the present specification.
Figure 8B:
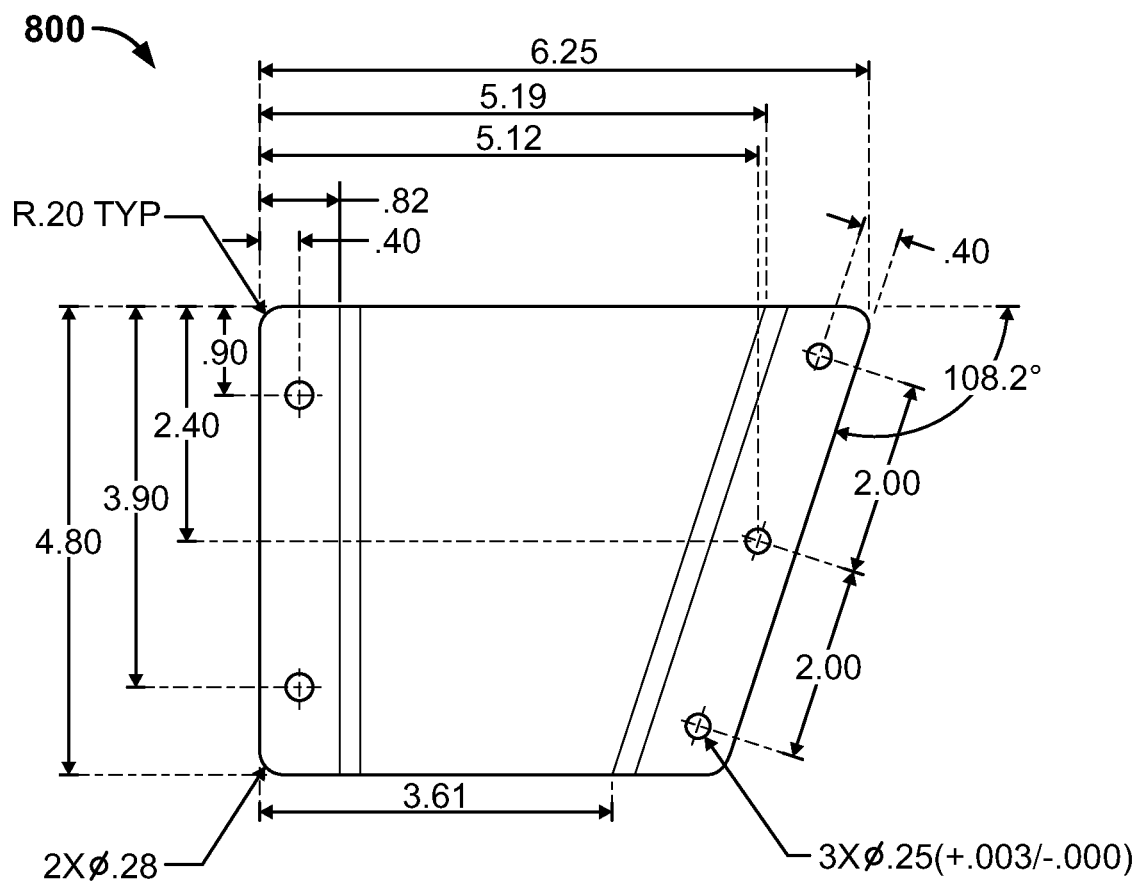
FIG. 8B illustrates another side view of shaker angle brackets that are used to position a mixing device within a system, in accordance with some embodiments of the present specification.
Figure 8C:
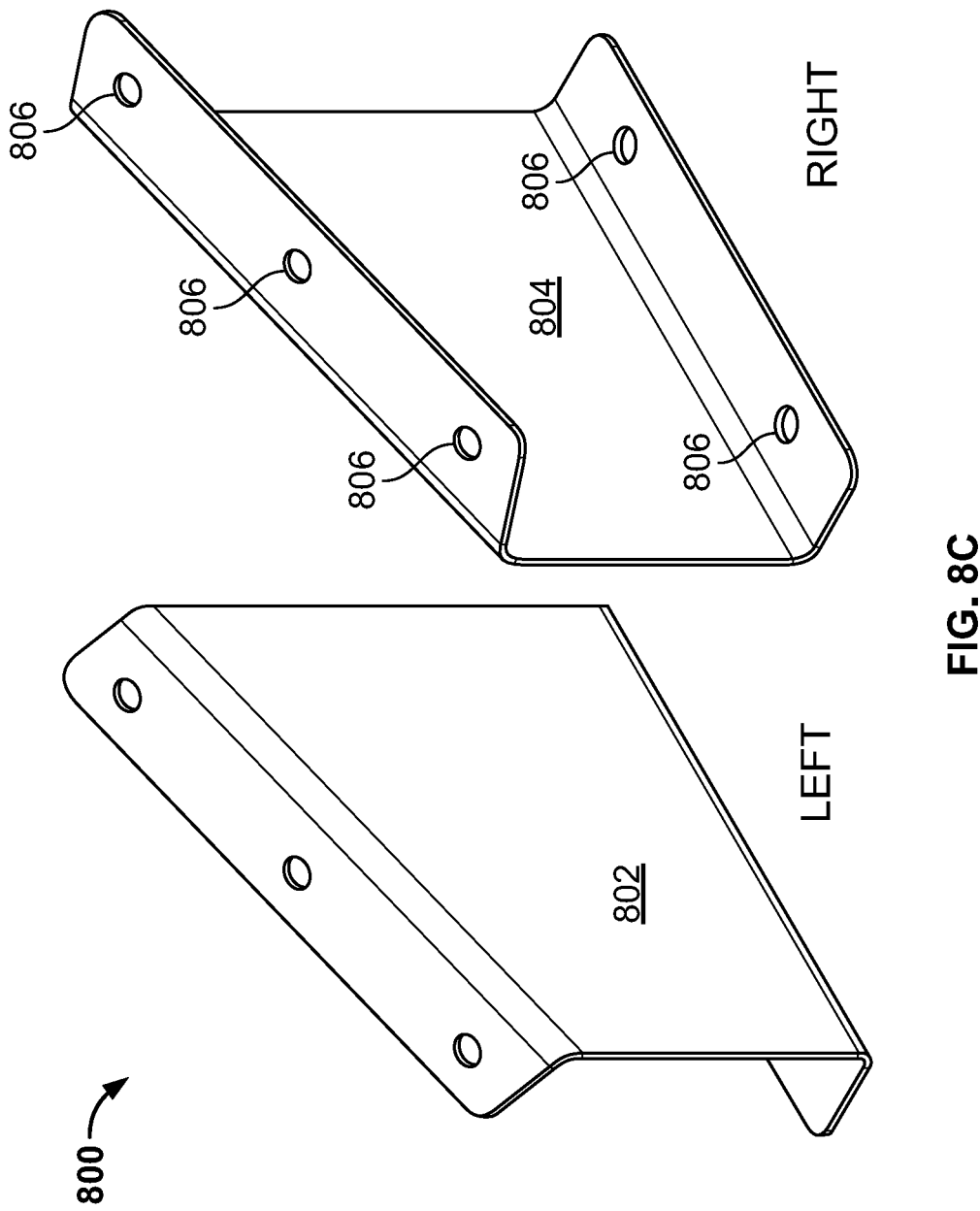
FIG. 8C illustrates a perspective view of shaker angle brackets that are used to position a mixing device within a system, in accordance with some embodiments of the present specification.

FIG. 8A illustrates a side view of shaker angle brackets 800 that are used to position mixing device 320 within the system, in accordance with some embodiments of the present specification. FIG. 8B illustrates a another side view of shaker angle brackets 800 that are used to position mixing device 320 within the system, in accordance with some embodiments of the present specification. FIG. 8C illustrates a perspective view of shaker angle brackets 800 that are used to position mixing device 320 within the system, in accordance with some embodiments of the present specification. Referring simultaneously to FIGS. 8A, 8B, and 8C, the mixing bag used to perform the mixing operation may be placed over an orbital mixer, which is fitted within the system with the help of brackets 800. In embodiments, brackets 800 are manufactured from Aluminum. In one embodiment, the Aluminum used for making brackets 800 is 0.060 inches thick. Referring simultaneously to FIGS. 8A, 8B, and 8C, brackets 800 include two parts 802 and 804, which mirror each other. In one embodiment, bracket 802 is placed on the left and bracket 804 is placed opposite to bracket 802 on the right. A mixing device, such as device 320 of FIG. 3I, is positioned on brackets 802 and 804. Holes 806 on both brackets 802 and 804 enable fixing the mixing device. In one embodiment, the mixing device provides a platform for placing the mixing bag, such as bag 700 of FIG. 7. Each bracket has two opposing sides connected by a flat surface between them. A top side 808 of each bracket is inclined at an angle for placing the mixing bag. In embodiments, the angle is in the range of 0 to 90 degrees. In one embodiment, the angle is 18.2 degrees, relative to a horizontal bottom side 810. The incline provided by top side 808 enables placing the mixing device, and therefore the mixing bag at an inclination, for an optimal mixing operation. Each edge 808 and 810 is bent in two ways to created angled brackets 802 and 804. The bent portions include holes 806 that enable fixing the mixing device with brackets 800.

In one embodiment, mixing device 320 has a capacity of 300 milliliters (ml). In one embodiment, mixing device 320 is configured to mix approximately 100 ml of plasma with the solvent during a single mixing operation. In one embodiment, solvent and plasma are mixed in a volume ratio of 2:1. For example, 100 ml of plasma is mixed with 200 ml of the solvent. In another embodiment, the solvent and plasma are mixed in a volume ratio of 1:1.

Solvent type, ratios and concentrations may vary in this step. Acceptable ratios of solvent to plasma include any combination of solvent and plasma. In some embodiments, (volume) ratios used are 2 parts plasma to 1 part solvent, 1 part plasma to 1 part solvent, or 1 part plasma to 2 parts solvent. In an embodiment, when using a solvent comprising 95 parts sevoflurane to 5 parts n-butanol, a ratio of two parts solvent per one part plasma is used. Additionally, in an embodiment employing a solvent containing n-butanol, the present specification uses a ratio of solvent to plasma that yields at least 5% n-butanol in the final solvent/plasma mixture. In an embodiment, a final concentration of n-butanol in the final solvent/plasma mixture is 3.33%. In embodiments, the final concentration of n-butanol in the resultant solvent/plasma mixture may vary and may be dependent on the solvent to plasma ratio, which may also vary. The plasma may be transported to the mixing device using a continuous or batch process. Further various sensing means may be included to monitor pressures, temperatures, flow rates, solvent levels, and the like. The solvents dissolve lipids from the plasma. In embodiments of the present specification, the solvents dissolve lipids to yield treated plasma that contains modified HDL particles with reduced lipid content. The process is designed such that HDL particles are treated to reduce their lipid levels and yield modified HDL particles without destruction of plasma proteins or substantially affecting LDL particles. It should be noted that there is no clinically significant decrease in blood constituents post-plasmapheresis.

In one embodiment, mixing device 320 is operated to mix the plasma solvent mixture for 60 seconds with an average mixing plasma batch volume of 99±7.5 ml.

In various embodiments, various energy measurements are provided as input to operate mixing device 320. Energy is introduced into the system in the form of varied mixing methods, time, and speed. A combination of the mixing parameters such as but not limited to the volume ratio of solvent to plasma, shape of the mixing device 320, and the amount of energy input used to operate mixing device 320, directly affect the success of the mixing operation to achieve delipidated HDL particles in the plasma. In one example, a solvent to plasma ratio of 2:1, for a batch of 100 ml plasma, mixed for 60 seconds, in a rectangular mixing device, using an energy input of 200 RPM does not delipidate the HDL particles from the plasma. In another example, a solvent to plasma ratio of 2:1, for a batch of 100 ml plasma, mixed for 60 seconds, in a large square mixing device, using an energy input of 400 RPM also does not delipidate the HDL particles from the plasma. Therefore, multiple parameters affect the success of delipidating HDL particles from the plasma. The effect of varying the different parameters is described in the subsequent sections, and in context of experiments illustrated in FIGS. 4, 5, and 6.

Referring back to step 218 of FIG. 2, and FIG. 3I, the plasma and the solvent interact with each other within mixing device 320 to the extent that HDL particles are delipidated, while LDL particles are not. The process is therefore termed as selective delipidation. In embodiments, the mixing is performed in order to achieve at least 80% delipidation of HDL particles.

Figure 3J:
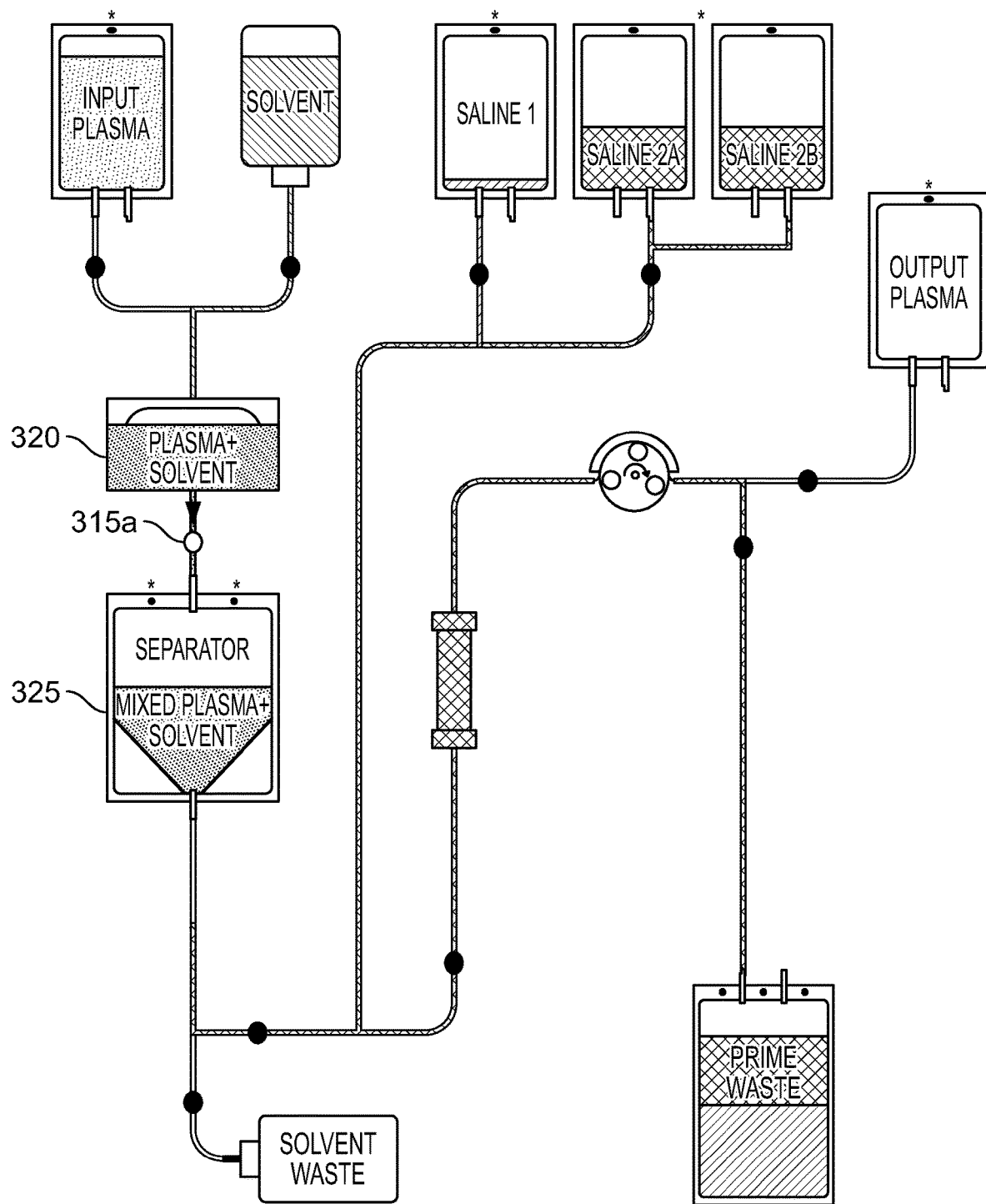
FIG. 3J is a schematic representation of the system illustrating the implementation of the process described in FIG. 2, in accordance with some embodiments of the present specification.

After the mixing, valve 315a is opened while all the other valves (315, 316, 315b, 315c, 315d, 315e, 315f, 315g, 330) remain closed, thus defining an eighth fluid flow path (FFP8) between mixing device 320 and separator 325. FFP8 is not in fluid communication with bags 305, 310, 355, 360, waste containers 335, 365, solvent extraction device 340, pump 350, and output container 345. At 220, once the mixing operation is completed, the solvent plasma mixture is transferred to a separator along FFP8, where the plasma and the solvent are separated by gravity. Referring to FIG. 3J, mixture of solvent and plasma is dropped down through a valve 315a in to a separator 325. The mixture remains in separator 325 until the solvent settles at the bottom of separator 325. The plasma is separated and remains in a layer above the solvent. The solvent employed is preferably of a higher density than plasma, and therefore settles at the bottom.

Figure 3K:
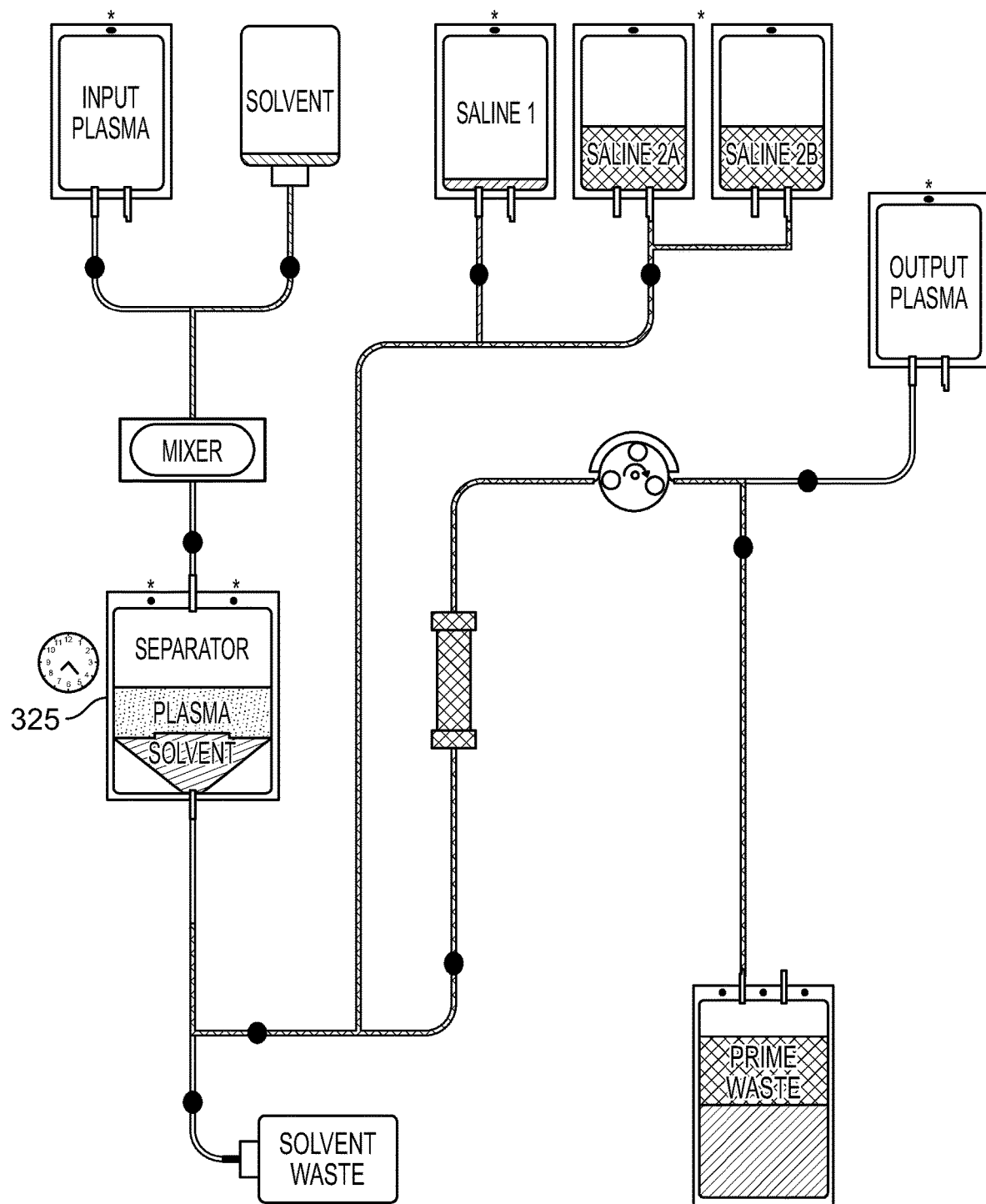
FIG. 3K is a schematic representation of the system illustrating the implementation of the process described in FIG. 2, in accordance with some embodiments of the present specification.

In embodiments, steps 216, 218, and 220 are performed iteratively, in batches, until separator 325 is filled to its capacity. Once the separator is filled to its capacity, all the valves (315, 316, 315a, 315b, 315c, 315d, 315e, 315f, 315g, 330) are closed. At 222, and referring to FIG. 3K, the collected mixture of plasma and solvent in separator 325 is allowed to stand for a period of time, until the solvent separates and settles at the bottom of separator 325. In embodiments, the period of time is dependent upon the time it takes for the solvent to fully separate without a loss or sacrifice in the amount of plasma. In one embodiment, the mixture is allowed to stand for approximately 30 minutes. In embodiments, separator 325 has a cone-shaped bottom that enables easy removal of bulk solvent in a subsequent step.

Figure 3L:
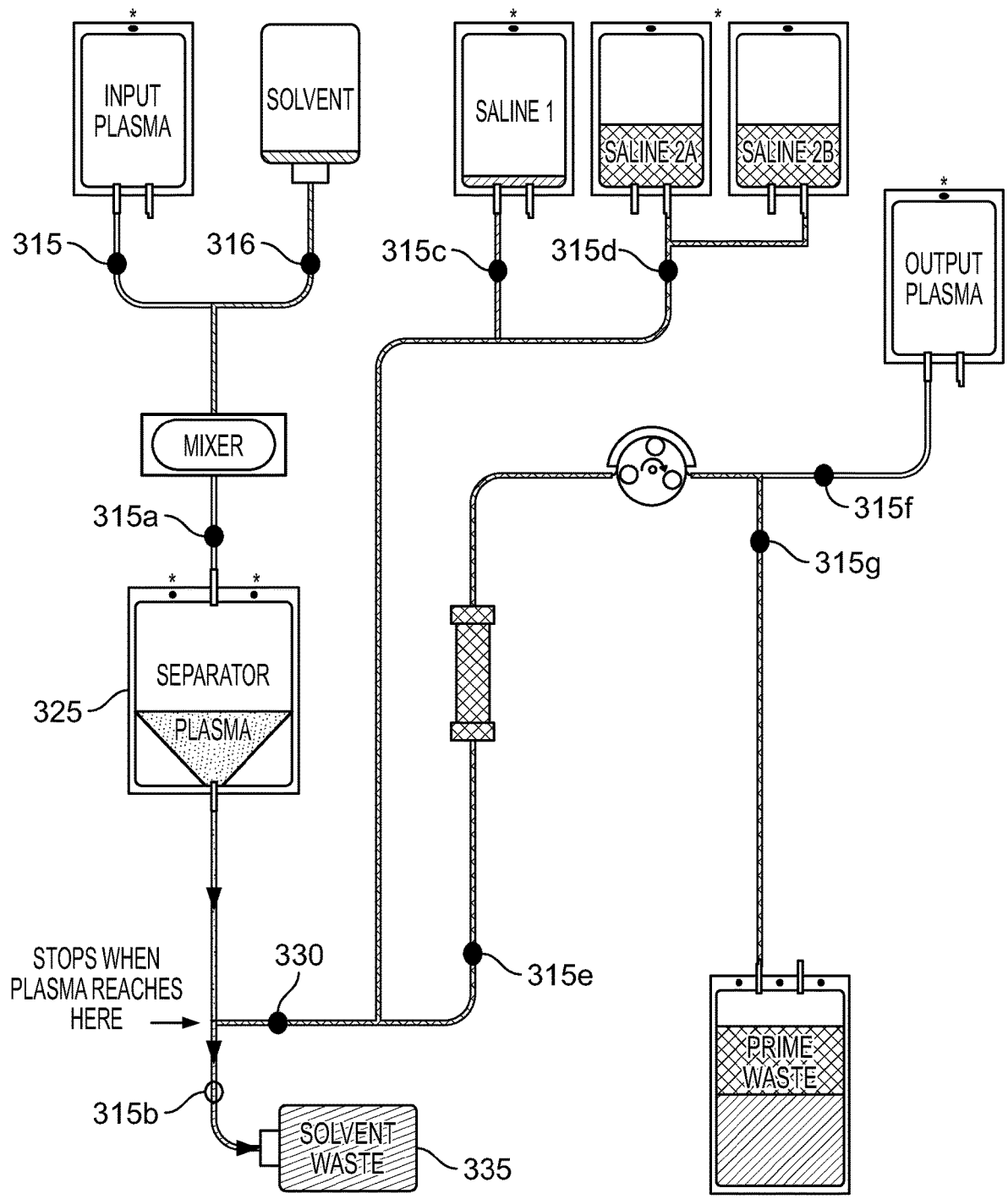
FIG. 3L is a schematic representation of the system illustrating the implementation of the process described in FIG. 2, in accordance with some embodiments of the present specification.

Following the separation, valve 315b is opened to define a ninth fluid flow path (FFP9) from separator 325 to first waste container 335. FFP9 is not in fluid communication with bags 305, 310, 355, 360, mixer 320, second waste container 365, solvent extraction device 340, pump 350, and output container 345. At 224, bulk solvent is removed from the separator 325 along FFP9. Referring to FIG. 3L, bulk solvent that has settled at the bottom portion of separator 325 flows to a first waste container 335 through a valve 315b, which, when open allows fluid to flow freely using gravity. In other embodiments, a pump may be employed to remove the solvent. Cone-shaped bottom of separator 325 aids easy removal of bulk solvent. Valve 315b is closed after bulk solvent has been moved through it and before the plasma from separator 325 reaches valve 315b.

In embodiments, a weight of separator 325 is known, in addition to weight of the plasma and of the solvent. In embodiments, the weight of the separator bag is continuously monitored. With this information, valve 315b is closed as soon as the amount of solvent removed from separator 325 corresponds to the known weight of the solvent. The weight of the solvent that flows to the first waste container 335 is, in an embodiment, indirectly monitored, because the amount of solvent that is added to the system and the amount of solvent present in the separator waste bag are known. In addition, the residual concentration of solvent that is in the plasma is based on validation of system parameters and a validated analysis of residual solvent concentrations via GC over many process runs.

Figure 3M:
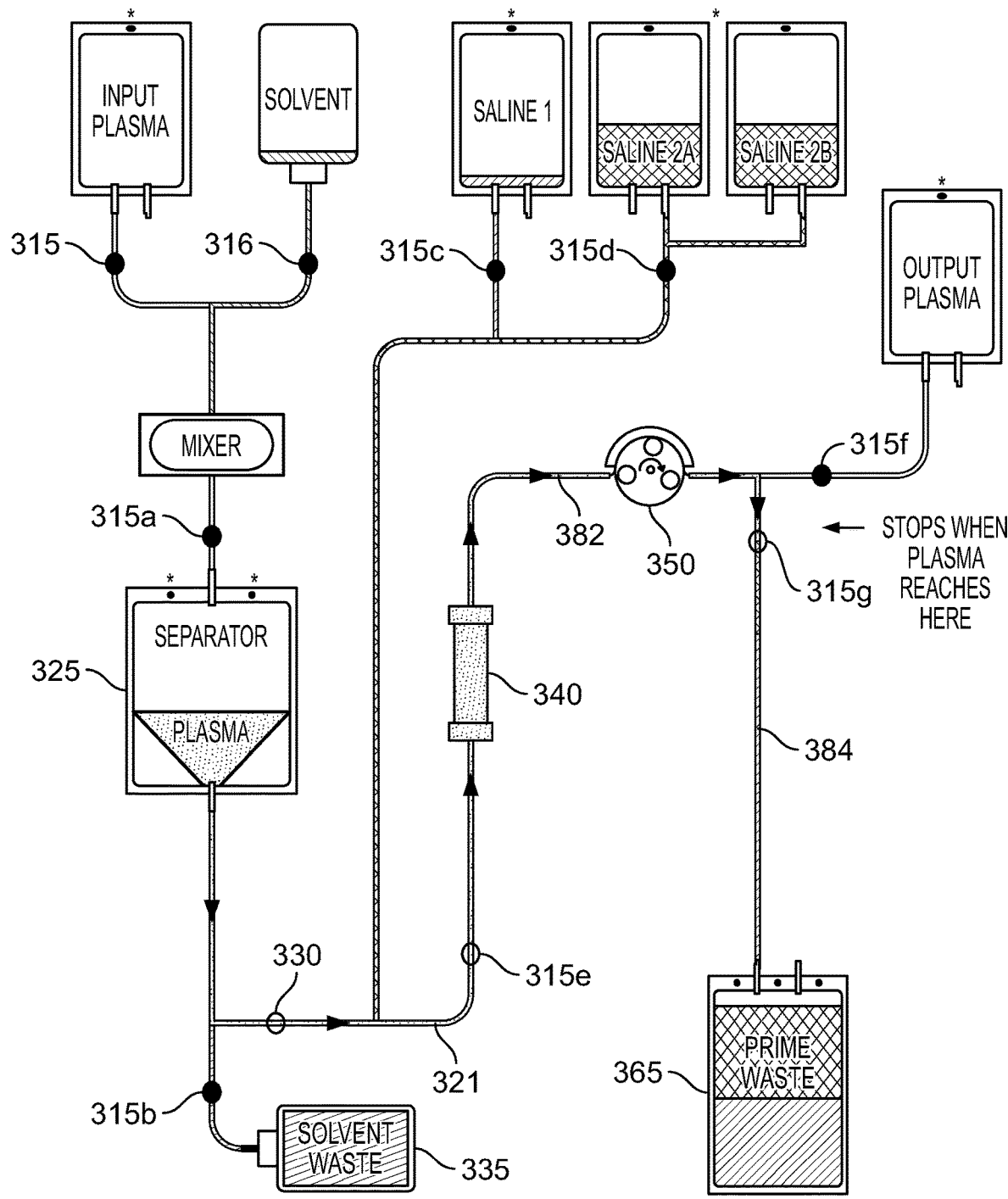
FIG. 3M is a schematic representation of the system illustrating the implementation of the process described in FIG. 2, in accordance with some embodiments of the present specification.

Once valve 315b is closed, valves 330, 315e, and 315g are opened while all other valves (315, 316, 315a, 315c, 315d, 315f, 330) remain closed, thus defining a tenth fluid flow path (FFP10). FFP10 is not in fluid communication with bags 305, 310, 355, 360, mixing device 320, first waste container 335, second waste container 365, and output device 345. At 226, and referring to FIG. 3M, a pump 350 is turned on and valves 330 and 315e are opened in order to pull plasma from separator 325 through fluid line 321 towards solvent extraction device 340, along FFP10. During this operation, initially a valve 315g is simultaneously open. Valve 315g is placed between solvent extraction device and second waste container 365. As the pump pulls the fluid present in lines 321 from separator 325 through solvent extraction device 340, priming fluid that was initially present in lines 321, 382, and 384, extending between separator 325 and second waste container 365, is pushed, or chased, further ahead in the lines by the plasma being pulled through valve 315g, towards second waste container 365 configured to contain prime waste. Once plasma (pulled by pump 350) reaches valve 315g, which is determined using both the tube length and the volume of fluid passed through the pump per revolution, the valve 315g is closed so that priming fluid is separated from plasma. This ensures that the plasma is not diluted and additional fluids are not collected along with the plasma that will subsequently be delivered back to the patient.

Figure 3N:
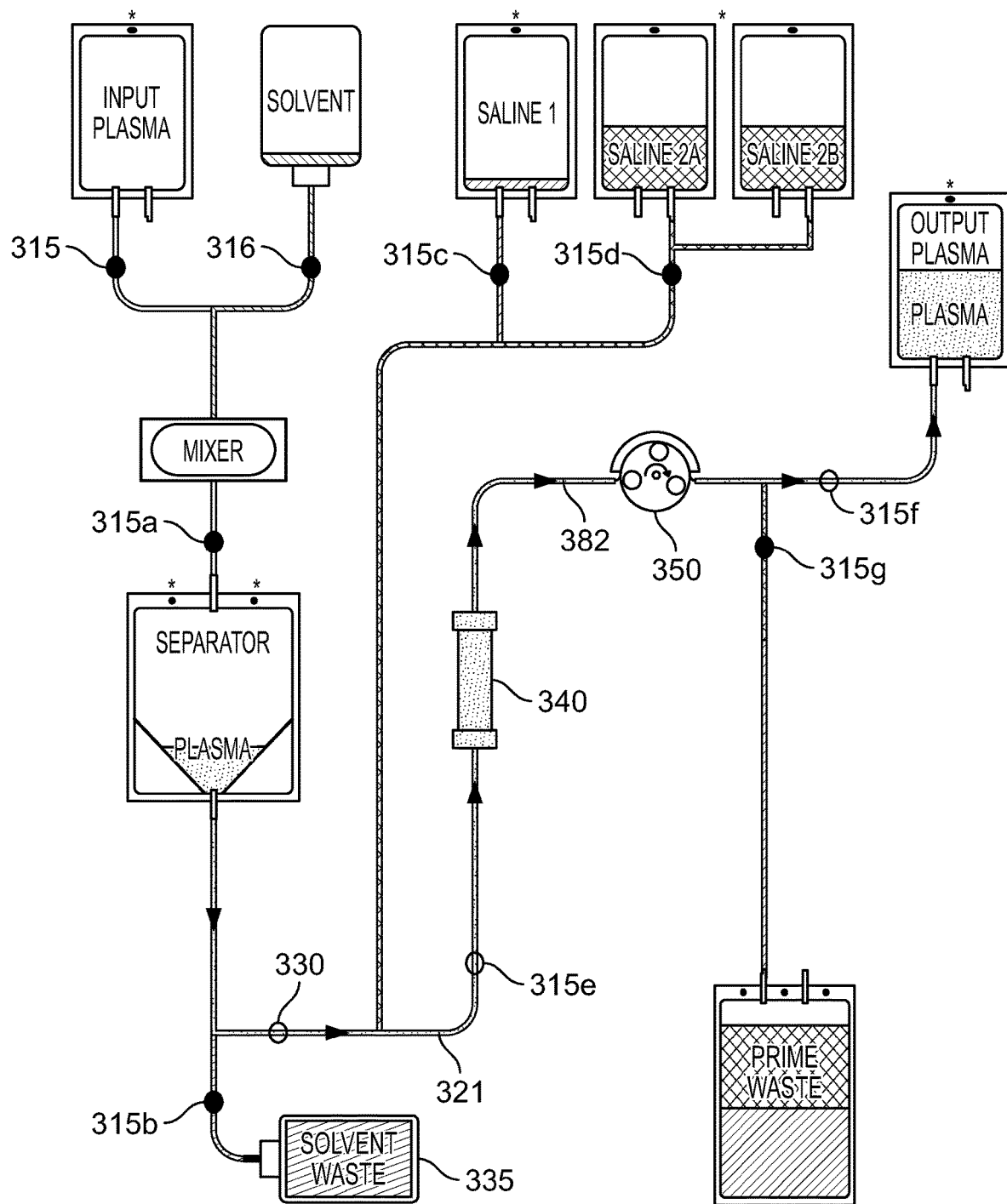
FIG. 3N is a schematic representation of the system illustrating the implementation of the process described in FIG. 2, in accordance with some embodiments of the present specification.

Subsequently, valve 315f is opened in addition to already open valves 330, 315e, while all other valves (315, 316, 315a, 315b, 315c, 315d, 315g) remain closed, thus defining another fluid flow path (FFP11) from separator 325, through solvent extraction device 340, to output device 345. At 228, and referring to FIG. 3N, pump 350 further pulls plasma along FFP11, from separator 325 through valves 330 and 315e, through solvent extraction device 340, and through a valve 315f, towards and into an output plasma container 345. As plasma moves through solvent extraction device 340, charcoal in solvent extraction device 340 absorbs and therefore extracts any remaining solvent from the plasma.

Figure 3O:
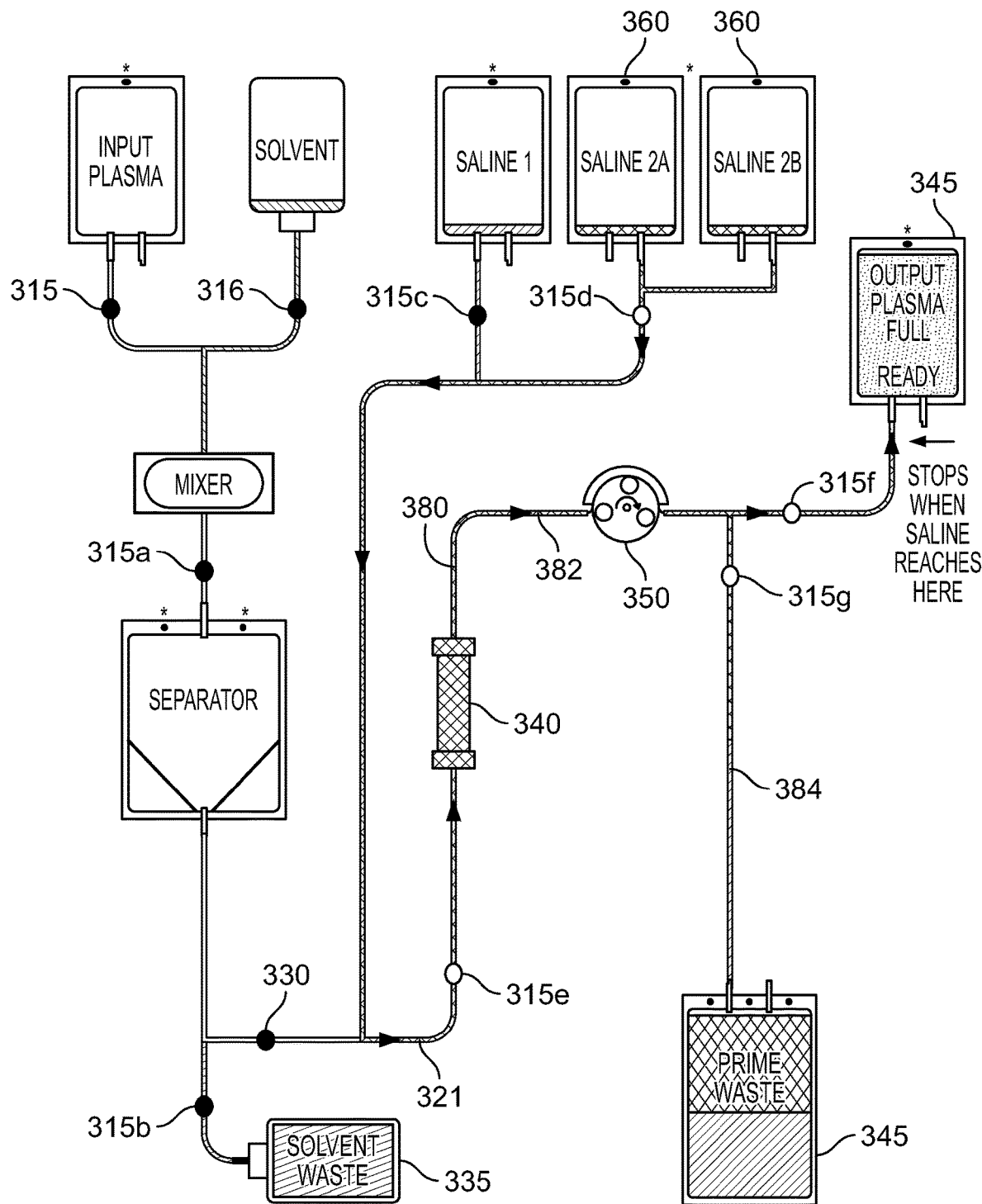
FIG. 3O is a schematic representation of the system illustrating the implementation of the process described in FIG. 2, in accordance with some embodiments of the present specification.

After extracting the delipidated plasma in to output container 345, valve 330 is closed along with valves 315, 316, 315a, 315b, 315c, 315g, and valve 315d is opened along with open valves 315e and 315f, thus defining another fluid flow path FFP12 from bags 360 through solvent extraction device 340, to output device 345. FFP 12 is not in fluid communication with bags 305, 310, 355, mixing device 320, separator 325, first waste container 335, and second waste container 365. At 230, and referring to FIG. 3O, once plasma is pulled out from separator 325 completely, pump 350 is still operated until priming fluid from bags 360 along FFP12 to follow or chase the plasma in the lines 380, 321, 382, and 384, through valve 315e, through solvent extraction device 340, and through valve 315f. Pump 350 is stopped once the priming fluid, chasing the plasma, reaches a position in the fluid line which is just before reaching output plasma container 345. In an embodiment, 150 mL of priming fluid is used to further chase the plasma into the plasma output bag 145/345 to ensure full recovery of the delipidated plasma. In an embodiment, chasing the fluid flow to the prime waste occurs to the point where pump 350 reaches a specific number of revolutions that is indicative of the plasma volume that has flowed through the system. Thus, the revolutions of the pump control how much fluid is in the prime waste or second waste container 345. Pump 350 is stopped to ensure that as much of the delipidated plasma that available in the system is collected in container 345, while the collected plasma is saved from unnecessary dilution by priming fluids. In embodiments, pump 350 is stopped automatically by the system based on the amount of plasma collected, which corresponds to the known amount of input plasma. In embodiments, the configurations of the disposable elements within the system are employed to program the system to automatically stop pump 350. In an embodiment, the tubing sets are of a known length and diameter. In addition, the volume of solvent at the bottom of separator bag 325 is also known in addition to the amount of plasma.

The extracted modified HDL plasma solution has an increased concentration of pre-beta HDL. It is estimated that the modified HDL in the delipidated plasma, has approximately 80-85% of pre-β particles, and about 15% of a HDL particles. Concentration of pre-beta HDL is greater in the modified HDL, relative to the original HDL that was present in the plasma before treating it with the solvent. Compared to the plasma solution originally separated from the blood fraction, which typically contains approximately 5% of pre-β HDL particles, the concentration of pre-β HDL particles is substantially increased.

At the end of this process, solvent waste is collected separately in first waste container 135/335, and prime waste is collected in second waste container 165/365, through their separate waste streams. This is advantageous for many reasons. Primarily, it is more expensive to dispose of certain types of waste, such as solvent waste. If solvent waste is "contaminated" with or combined with other types of waste, the additional waste will have to be disposed of in the same costly manner as solvent waste. Prime waste, for example, which consists of mostly saline and/or glucose, can be directed to a normal hospital waste stream. If mixed with solvent, the prime waste will have to be diverted into the chemical waste disposal channels, by default. By separating out waste, each waste stream can be treated and disposed of appropriately. In some embodiments, the solvent waste can be treated or scrubbed to reclaim a pure solvent so that it can be re-used.

Examples of effect of varying multiple parameters are now explained briefly. Among various methods by which plasma may be delipidated, parameters affecting the extent of delipidation may be broadly identified as chemical and mechanical parameters. Examples of chemical parameters may include, but may not be limited to, plasma type (bovine, human, lipemic), plasma volumes, solvent type (n-butanol/DiPE or n-butanol/sevoflurane, any other), percentage of n-butanol present in the solvent, and solvent to plasma ratio. Examples of some of the mechanical parameters may include, a method of mixing (rocker table, vortex, any other), mixing duration, method of separation (gravity, centrifuge, any other), separation time, and centrifuge force.

For purposes of illustrating the effect of varying these parameters on the extent of delipidation, an experimental delipidation process was performed in a laboratory setting. The results, presented in table 400 of FIG. 4, are briefly discussed herein. Referring to table 400, first column 402 lists different embodiments in separate rows. Each embodiment corresponds to a unique combination of the parameters that affect the extent of delipidation. The second column 404 lists the plasma type used for each embodiment. The plasma type was selected from the plasma of a human or that of a bovine. Column 406 lists the plasma volumes (in milliliter) used in each embodiment. Column 408 lists the type of solvent used. In most embodiments, the solvent type is either of n-Butanol and DiPe. Column 410 lists the percentage of n-Butanol used, which may also be inferred as an indication of the solvent ratio. Column 412 lists the solvent to plasma ratio used in each embodiment. Column 414 lists the type of mixing method used for each embodiment. Column 416 lists the time for which the mixing process was implemented. Column 418 lists the chosen method for separation of the plasma and the solvent. Column 420 lists the time for which the process of separation was performed for each embodiment. Column 422 lists the amount of centrifugal force applied for each embodiment. Lastly, column 424 lists the results that show the variation across each embodiment, in the percentage of lipids that remain in the treated plasma.

Embodiment 1

About 10 milliliters (ml) of plasma derived from a human was used. This plasma was mixed with n-butanol/DiPE solvent. A solvent to plasma ratio of 2:1 was used. The rocker table was used to perform the mixing operation, for about five minutes. A centrifugal force of 563×G was applied for about two minutes to separate the delipidated plasma from the solvent. The effect of varying percentage of n-butanol in the solvent within a range of 0% to 40% is that remaining lipids progressively decrease with an increase in the quantity of n-butanol in the solvent.

Embodiment 2

In another similar experiment, 10 ml of bovine plasma was mixed with n-butanol/DiPE solvent containing 25% n-butanol. The mixture was mixed using a rocker table for about five minutes. A centrifugal force of 563×G was applied for about two minutes to separate the delipidated plasma from the solvent. The effect of varying the solvent to plasma ratio in a range of 0.25 to 10 is that a lower ratio, specifically within a range of 1 to 2, results in most reduced lipid concentration in the delipidated solution.

Embodiment 3

In another similar experiment, 10 ml of human plasma was mixed with n-butanol/DiPE solvent containing 25% n-butanol, using a solvent to plasma ratio of 2:1. Different samples of the mixture were mixed using a rocker table and using a vortex. Gravity separation was used for about five minutes to separate some of the samples, as well as a centrifugal force of 563×G was applied for about two minutes to separate the delipidated plasma from the solvent for the remaining samples. The effect of different mixing methods and by varying the duration of mixing for both the methods used for separating (gravity and centrifuge) is that there is a variation on the concentration of lipids remaining in the delipidated plasma.

Embodiment 4

In yet another similar experiment, 10 ml of human plasma was mixed with n-butanol/DiPE solvent containing 25% n-butanol, using a solvent to plasma ratio of 2:1. The mixture was mixed using a rocker table for about five minutes. A range of centrifugal force was applied for about two minutes to separate the delipidated plasma from the solvent. The effect of varying the centrifugal force used for separation on the lipid concentration remaining in the delipidated plasma FIG. 5 is a table 500 that lists another exemplary set of variables that may affect the delipidation process and resultant percentage selective delipidation and is presented by way of example only to show possible combinations of variables. The ideal results from these experiments include a substantial change in HDL concentration, no change in LDL concentration, preservation of Apo-A1, preservation of Apo-B, and preservation of phospholipids, resulting in selective delipidation of plasma. Referring to the table 500, the first column 502 lists the type of solvent mix used. The constituents for the solvent solution may contain one or more of Sevoflurane (S), n-butanol (N), DiPE (D), and Isofluorane (I). The second column 504 (Solvent Ratio) lists the ratio of the constituents of the solvent that may be used in the solvent solution, corresponding to the first column. The third column 506 (Plasma:Solvent Ratio) lists the proportion of the plasma and the solvent that may be mixed together for the delipidation. The fourth column (Mix Method) 508 states the corresponding mixing method that may be used. The fifth column (Time) 510 provides the corresponding duration for which mixing can be performed. The sixth column (Sep. Method) 512 lists the method used for separation of the delipidated plasma and the solvent. The two methods commonly used for separation are gravity separation (GS) and centrifugal separation (CF), in the embodiments of the present specification.

FIG. 6 is a table 600 that provides another exemplary set of variables that may be used for normal plasma and lipemic IV plasma using different solvents and different methods of separation. A first column 602 (Plasma) lists the type of plasma (normal or lipemic IV) used in each embodiment, where each row corresponds to a different embodiment. Column 604 (solvents) lists the type of solvent or solvent mixture used corresponding to each embodiment. Column 606 (Ratio) lists the ratios of constituents in a solvent mixture for each embodiment. Column 608 (P:S) lists the plasma to solvent ratio corresponding to each embodiment. Column 610 (Volume) lists the volume of the plasma used for each embodiment. Column 612 (S Volume) lists the volume of the solvent/solvent mixture used for each embodiment. The volumes of the plasma and the solvent/solvent mixture corresponds to the ratio listed in column 608. Column 614 (Mix Method) lists the method of mixing used for each embodiment. Column 616 (Time) lists the duration for which the mixing was performed. Column 618 (Separation) lists the method used for separation (centrifugal or gravity separation) of the plasma and the solvent. Column 620 (time(min)) lists the duration (in minutes) for which the separation process was performed for each embodiment. Lastly, column 622 (Solvent Removal) lists the type of method used for solvent removal. As seen in table 600, a charcoal column was used in all the embodiments to remove the solvent.

In general, the present specification preferably comprises configurations wherein all inputs, such as input plasma and input solvents, disposable elements, such as mixing bags, separator bags, waste bags, solvent extraction devices, and solvent detection devices, and output containers are in easily accessible positions and can be readily removed and replaced by a technician.

To enable the operation of the above described embodiments of the present invention, it is preferable to supply a user of such embodiments with a packaged set of components, in kit form, comprising each component required to practice embodiments of the present specification. The kit may include an input fluid container (i.e. a high density lipoprotein source container), a lipid removing agent source container (i.e. a solvent container), disposable components of a mixer, such as a bag or other container, disposable components of a separator, such as a bag or other container, disposable components of a solvent extraction device (i.e. a charcoal column), an output container, disposable components of a waste container, such as a bag or other container, solvent detection devices, and, a plurality of tubing and a plurality of valves for controlling the flow of input fluid (high density lipoprotein) from the input container and lipid removing agent (solvent) from the solvent container to the mixer, for controlling the flow of the mixture of lipid removing agent, lipid, and particle derivative to the separator, for controlling the flow of lipid and lipid removing agent to a waste container, for controlling the flow of residual lipid removing agent, residual lipid, and particle derivative to the extraction device, and for controlling the flow of particle derivative to the output container.

In one embodiment, a kit comprises a plastic container having disposable components of a mixer, such as a bag or other container, disposable components of a separator, such as a bag or other container, disposable components of a waste container, such as a bag or other container, and, a plurality of tubing and a plurality of valves for controlling the flow of input fluid (high density lipoprotein) from the input container and lipid removing agent (solvent) from the solvent container to the mixer, for controlling the flow of the mixture of lipid removing agent, lipid, and particle derivative to the separator, for controlling the flow of lipid and lipid removing agent to a waste container, for controlling the flow of residual lipid removing agent, residual lipid, and particle derivative to the extraction device, and for controlling the flow of particle derivative to the output container. Disposable components of a solvent extraction device (i.e. a charcoal column), the input fluid, the input solvent, and solvent extraction devices may be provided separately.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of priming a plasma processing system comprising at least a first fluid flow path, the method comprising:
   using a first fluid, flushing the first fluid flow path, wherein the first fluid flow path is defined by a source of the first fluid, a first valve positioned between the source of the first fluid and a first fluid flow line, a second valve positioned between the first fluid flow line and a second fluid flow line, a first pump positioned between the second fluid flow line and a third fluid flow line, and a prime waste container in fluid communication with the third fluid flow line;
   closing the second valve, thereby preventing a flow of the second fluid to the second fluid flow line, the third fluid flow line, and the prime waste container;
   closing the first valve, thereby preventing a flow of the first fluid to the first fluid flow line from the source of the first fluid;
   opening a third valve, wherein the third valve is positioned between the first fluid flow line, and a fourth fluid flow line, wherein the third valve and the fourth fluid flow line are components of the plasma processing system;
   opening a fourth valve, wherein the fourth valve is positioned between a source of a second fluid and the first fluid flow line, thereby enabling a flow of the second fluid from the source of second fluid to the first fluid flow line and the fourth fluid flow line and wherein the fourth valve and the source of the second fluid are components of the plasma processing system; and
   closing the third valve and opening the second valve and a fifth valve, thereby enabling a flow of fluid from the source of second fluid to the first fluid flow line, the second fluid flow line, the third fluid flow line and the prime waste container, wherein the fifth valve is positioned between the second fluid flow line and the third fluid flow line.

2. The method of claim 1 wherein the first fluid is saline.

3. The method of claim 1 wherein the second fluid is saline.

4. The method of claim 1 wherein the plasma processing system comprises a source of plasma, a source of solvent, and an output plasma container and wherein the first fluid flow path is not in fluid communication with the source of plasma, the source of solvent, or the output plasma container.

5. The method of claim 1 wherein the plasma processing system further comprises a connector tube positioned along the second fluid flow line.

6. The method of claim 5 further comprising, after closing the third valve and opening the second valve, removing the connector tube.

7. The method of claim 6 further comprising, after removing the connector tube, inserting a solvent extraction device in place of the removed connector tube.

8. The method of claim 7 wherein the solvent extraction device is a charcoal column.

9. The method of claim 1 wherein the fourth fluid flow line is in fluid communication with a separator.

10. A method of priming a plasma processing system comprising at least a first fluid flow path and a second fluid flow path, the method comprising:
    flushing the first fluid flow path, wherein the first fluid flow path is defined by a source of a first fluid, a first valve positioned between the source of the first fluid and a first fluid flow line, a second valve positioned between the first fluid flow line and a second fluid flow line, a first pump positioned between the second fluid flow line and a third fluid flow line, and a prime waste container in fluid communication with the third fluid flow line, wherein the flushing of the first fluid flow path is achieved by opening the first valve and opening the second valve, thereby enabling a flow of the first fluid to the first fluid flow line, the second fluid flow line, the third fluid flow line, and the prime waste container; and
    flushing the second fluid flow path, wherein the second fluid flow path is defined by a source of a second fluid, a third valve, wherein the third valve is positioned between the first fluid flow line and a fourth fluid flow line, and a fourth valve, wherein the fourth valve is positioned between the source of the second fluid and the first fluid flow line, wherein the flushing of the second fluid flow path is achieved by closing the second valve, thereby preventing a flow of the second fluid to the second fluid flow line, the third fluid flow line, and the prime waste container, closing the first valve, thereby preventing a flow of the first fluid to the first fluid flow line from the source of the first fluid, opening the third valve, and opening the fourth valve, thereby enabling a flow of the second fluid along the second fluid flow path.

11. The method of claim 10 wherein the first fluid is saline and the second fluid is saline.

12. The method of claim 10 wherein the plasma processing system comprises a source of plasma, a source of solvent, and an output plasma container and wherein the first fluid flow path is not in fluid communication with a source of plasma, a source of solvent, or an output plasma container.

13. The method of claim 10 wherein the plasma processing system further comprises a connector tube positioned along the second fluid flow line.

14. The method of claim 13 further comprising, after closing the second valve, waiting for a period of time and then opening the second valve, thereby enabling a flow of the second fluid to the second fluid flow line, the third fluid flow line, and the prime waste container.

15. The method of claim 14 further comprising, after the opening the second valve, removing the connector tube.

16. The method of claim 15 wherein, after removing the connector tube, inserting a solvent extraction device in place of the removed connector tube.

17. The method of claim 16 wherein the solvent extraction device is a charcoal column.

18. The method of claim 10 further comprising a fifth valve positioned between the second fluid flow line and the third fluid flow line.

19. The method of claim 10 wherein the fourth fluid flow line is in fluid communication with a separator.

* * * * *